(12) United States Patent
Johnson

(10) Patent No.: US 12,226,401 B2
(45) Date of Patent: *Feb. 18, 2025

(54) MOLECULAR GENETIC APPROACH TO TREATMENT AND DIAGNOSIS OF ALCOHOL AND DRUG DEPENDENCE

(71) Applicant: University of Virginia Patent Foundation, Charlottesville, VA (US)

(72) Inventor: Bankole A. Johnson, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 94 days.

This patent is subject to a terminal disclaimer.

(21) Appl. No.: 18/164,175

(22) Filed: Feb. 3, 2023

(65) Prior Publication Data

US 2023/0241032 A1 Aug. 3, 2023

Related U.S. Application Data

(60) Continuation of application No. 17/659,641, filed on Apr. 18, 2022, which is a continuation of application No. 16/784,051, filed on Feb. 6, 2020, now Pat. No. 11,324,723, which is a continuation of application No. 15/397,076, filed on Jan. 3, 2017, now Pat. No. 10,603,307, which is a continuation of application No. 14/266,313, filed on Apr. 30, 2014, now Pat. No. 9,539,242, which is a division of application No. 13/589,603, filed on Aug. 20, 2012, now Pat. No. 8,753,815, which is a continuation of application No. PCT/US2011/042823, filed on Jul. 1, 2011.

(60) Provisional application No. 61/488,328, filed on May 20, 2011, provisional application No. 61/429,416, filed on Jan. 3, 2011, provisional application No. 61/361,203, filed on Jul. 2, 2010.

(51) Int. Cl.
| | | |
|---|---|---|
| *C12Q 1/68* | (2018.01) | |
| *A61K 31/4178* | (2006.01) | |
| *A61K 31/7048* | (2006.01) | |
| *C12Q 1/6883* | (2018.01) | |
| *C12Q 1/6888* | (2018.01) | |
| *G16B 20/00* | (2019.01) | |

(52) U.S. Cl.
CPC ...... *A61K 31/4178* (2013.01); *A61K 31/7048* (2013.01); *C12Q 1/6883* (2013.01); *C12Q 1/6888* (2013.01); *G16B 20/00* (2019.02); *C12Q 2600/106* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | |
|---|---|---|
| 5,550,021 A | 8/1996 | Blum et al. |
| 6,169,105 B1 | 1/2001 | Wong et al. |
| 6,323,236 B2 | 9/2001 | McElroy |
| 7,033,771 B2 | 4/2006 | Brooks |
| 8,697,361 B2 | 4/2014 | Johnson |
| 8,753,815 B2 | 6/2014 | Johnson |
| 9,539,242 B2 | 1/2017 | Johnson |
| 10,533,226 B2 | 1/2020 | Johnson |
| 10,603,307 B2 | 3/2020 | Johnson |
| 10,619,209 B2 | 4/2020 | Johnson |
| 10,995,374 B2 | 5/2021 | Johnson |
| 10,997,121 B1 | 5/2021 | Jones et al. |
| 11,116,753 B2 | 9/2021 | Johnson |
| 11,324,723 B2 | 5/2022 | Johnson |
| 11,351,154 B2 | 6/2022 | Johnson |
| 11,905,562 B2 | 2/2024 | Johnson |
| 11,957,664 B2 | 4/2024 | Johnson |
| 2001/0023254 A1 | 9/2001 | McElroy |
| 2002/0091320 A1 | 7/2002 | Crutchfield et al. |
| 2003/0100479 A1 | 5/2003 | Dow et al. |
| 2003/0114475 A1 | 6/2003 | Fox et al. |
| 2003/0153590 A1 | 8/2003 | Kurkela et al. |
| 2004/0167164 A1 | 8/2004 | Pozuelo |
| 2005/0089890 A1 | 4/2005 | Cubicciotti |
| 2005/0245461 A1 | 11/2005 | Ehrich et al. |
| 2006/0286594 A1 | 12/2006 | Mundo et al. |
| 2007/0072899 A1 | 3/2007 | Johnson et al. |
| 2007/0088100 A1 | 4/2007 | Ahmed et al. |
| 2007/0167423 A1 | 7/2007 | Bergauer et al. |
| 2007/0196841 A1 | 8/2007 | Ruano et al. |

(Continued)

FOREIGN PATENT DOCUMENTS

| | | |
|---|---|---|
| AT | E608888 T1 | 4/2013 |
| AU | 2011274355 B1 | 2/2017 |

(Continued)

OTHER PUBLICATIONS

Enoch et al; Molecular Psychiatry, vol. 16, 2011, pp. 1139-1146.*

(Continued)

*Primary Examiner* — Jehanne S Sitton
(74) *Attorney, Agent, or Firm* — Schwegman Lundberg & Woessner, P.A.

(57) ABSTRACT

Compositions and methods are provided that are useful for diagnosing, treating, and monitoring alcohol dependence and disorders, susceptibility to alcohol dependence disorders, as well as drug related dependence and disorders. The methods include treating patients with an antagonist of the serotonin receptor 5-HT3 for such disorders, wherein the patient's serotonin transporter gene SLC6A4 is known to have particular genotypes.

21 Claims, 14 Drawing Sheets

Specification includes a Sequence Listing.

(56) References Cited

U.S. PATENT DOCUMENTS

| | | |
|---|---|---|
| 2007/0275970 A1 | 11/2007 | Weber |
| 2007/0292880 A1 | 12/2007 | Philibert et al. |
| 2008/0004291 A1 | 1/2008 | Singh |
| 2008/0228824 A1 | 9/2008 | Kenedy et al. |
| 2009/0269773 A1 | 10/2009 | Fantl et al. |
| 2010/0041689 A1 | 2/2010 | Johnson et al. |
| 2010/0076006 A1 | 3/2010 | Johnson et al. |
| 2010/0093762 A1 | 4/2010 | Wu |
| 2011/0065628 A1 | 3/2011 | Johnson et al. |
| 2011/0112159 A1 | 5/2011 | Johnson |
| 2011/0264374 A1 | 10/2011 | Johnson et al. |
| 2012/0115149 A1 | 5/2012 | Johnson |
| 2012/0302592 A1 | 11/2012 | Johnson et al. |
| 2013/0012559 A1 | 1/2013 | Johnson |
| 2013/0096173 A1 | 4/2013 | Johnson et al. |
| 2014/0206734 A1 | 7/2014 | Johnson |
| 2014/0288139 A1 | 9/2014 | Johnson |
| 2016/0139161 A1 | 5/2016 | Johnson |
| 2016/0331728 A1 | 11/2016 | Johnson |
| 2016/0376658 A1 | 12/2016 | Johnson |
| 2017/0226585 A1 | 8/2017 | Johnson |
| 2017/0239222 A1 | 8/2017 | Johnson |
| 2018/0251840 A1 | 9/2018 | Johnson |
| 2018/0344701 A1 | 12/2018 | Johnson |
| 2019/0002984 A1 | 1/2019 | Johnson |
| 2019/0249255 A1 | 8/2019 | Johnson |
| 2020/0199679 A1 | 6/2020 | Johnson |
| 2020/0316028 A1 | 10/2020 | Johnson |
| 2021/0000797 A1 | 1/2021 | Johnson |
| 2021/0023058 A1 | 1/2021 | Johnson |
| 2021/0301346 A1 | 9/2021 | Johnson |
| 2023/0014787 A1 | 1/2023 | Johnson |
| 2023/0263776 A1 | 8/2023 | Johnson |
| 2024/0247313 A1 | 7/2024 | Johnson |

FOREIGN PATENT DOCUMENTS

| | | |
|---|---|---|
| CA | 219554 A | 6/1922 |
| CA | 2716498 C | 12/2020 |
| EA | 019200 B1 | 1/2014 |
| EA | 024450 B1 | 9/2016 |
| EA | 027743 B1 | 8/2017 |
| EP | 0945133 A1 | 9/1999 |
| EP | 1262196 A2 | 12/2002 |
| EP | 2801625 A1 | 11/2017 |
| HK | 1151091 B1 | 1/2012 |
| IL | 278149 | 11/2023 |
| JP | 2010513569 A | 4/2010 |
| JP | 2010537990 A | 12/2010 |
| RU | 2075978 C1 | 3/1997 |
| UA | 116615 C2 | 4/2018 |
| WO | WO-0050639 A2 | 8/2000 |
| WO | WO-03097873 A2 | 11/2003 |
| WO | WO-03100091 A1 | 12/2003 |
| WO | WO-2007009691 A2 | 1/2007 |
| WO | WO-2007039123 A2 | 4/2007 |
| WO | WO-2007095580 A2 | 8/2007 |
| WO | WO-2008077092 A2 | 6/2008 |
| WO | WO-2008095086 A2 | 8/2008 |
| WO | WO-2008095086 A3 | 8/2008 |
| WO | WO-2009010837 A2 | 1/2009 |
| WO | WO-2009026381 A2 | 2/2009 |
| WO | WO-2009026381 A3 | 2/2009 |
| WO | WO-2009029308 A1 | 3/2009 |
| WO | WO-2009108837 A2 | 9/2009 |
| WO | WO-2009108837 A3 | 9/2009 |
| WO | WO-2010126603 A1 | 11/2010 |
| WO | WO-2012003462 A1 | 1/2012 |
| WO | WO-2012003462 A4 | 1/2012 |
| WO | WO-2013036721 A1 | 3/2013 |

OTHER PUBLICATIONS

"U.S. Appl. No. 12/520,095, Advisory Action mailed Mar. 7, 2012", 4 pgs.

"U.S. Appl. No. 12/520,095, Final Office Action mailed Sep. 1, 2011", 25 pgs.

"U.S. Appl. No. 12/520,095, Non Final Office Action mailed Feb. 18, 2011", 25 pgs.

"U.S. Appl. No. 12/520,095, Non Final Office Action mailed Aug. 21, 2013", 23 pgs.

"U.S. Appl. No. 12/520,095, Preliminary Amendment filed Jun. 19, 2009", 11 pgs.

"U.S. Appl. No. 12/520,095, Response filed Jan. 17, 2012 to Final Office Action mailed Sep. 1, 2011", 13 pgs.

"U.S. Appl. No. 12/520,095, Response filed Feb. 29, 2012 to Final Office mailed Sep. 1, 2011", 13 pgs.

"U.S. Appl. No. 12/520,095, Response filed Jun. 20, 2011 to Non Final Office Action mailed Feb. 18, 2011", 14 pgs.

"U.S. Appl. No. 12/520,095, Response filed Dec. 6, 2010 to Restriction Requirement mailed Aug. 5, 2010", 14 pgs.

"U.S. Appl. No. 12/520,095, Restriction Requirement mailed Aug. 5, 2010", 8 pgs.

"U.S. Appl. No. 12/525,320, Non Final Office Action mailed Feb. 8, 2012", 25 pgs.

"U.S. Appl. No. 12/525,320, Preliminary Amendment filed Jul. 31, 2009", 9 pgs.

"U.S. Appl. No. 12/525,320, Response filed Jan. 17, 2012 to Restriction Requirement mailed Nov. 17, 2011", 9 pgs.

"U.S. Appl. No. 12/525,320, Restriction Requirement mailed Nov. 17, 2011", 10 pgs.

"U.S. Appl. No. 12/674,348, Final Office Action mailed Sep. 10, 2012", 17 pgs.

"U.S. Appl. No. 12/674,348, Non Final Office Action mailed Dec. 13, 2011", 16 pgs.

"U.S. Appl. No. 12/674,348, Preliminary Amendment filed Feb. 19, 2010", 3 pgs.

"U.S. Appl. No. 12/674,348, Response filed May 14, 2012 to Non Final Office Action mailed Dec. 13, 2011", 13 pgs.

"U.S. Appl. No. 12/675,486, Non Final Office Action mailed Apr. 23, 2013", 22 pgs.

"U.S. Appl. No. 12/675,486, Preliminary Amendment filed Feb. 26, 2010", 16 pgs.

"U.S. Appl. No. 12/675,486, Response filed Aug. 24, 2012 to Restriction Requirement mailed May 7, 2012", 15 pgs.

"U.S. Appl. No. 12/675,486, Restriction Requirement mailed May 7, 2012", 6 pgs.

"U.S. Appl. No. 12/919,905, Advisory Action mailed Jul. 16, 2013", 3 pgs.

"U.S. Appl. No. 12/919,905, Examiner Interview Summary mailed Jul. 15, 2013", 3 pgs.

"U.S. Appl. No. 12/919,905, Final Office Action mailed May 10, 2013", 16 pgs.

"U.S. Appl. No. 12/919,905, Non Final Office Action mailed Feb. 1, 2013", 16 pgs.

"U.S. Appl. No. 12/919,905, Notice of Allowance mailed Nov. 20, 2013", 9 pgs.

"U.S. Appl. No. 12/919,905, Preliminary Amendment mailed Aug. 27, 2010", 11 pgs.

"U.S. Appl. No. 12/919,905, PTO Response to 312 Communication mailed Feb. 26, 2014", 2 pgs.

"U.S. Appl. No. 12/919,905, Response filed Jan. 11, 2013 to Restriction Requirement mailed Dec. 12, 2012", 12 pgs.

"U.S. Appl. No. 12/919,905, Response filed May 1, 2013 to Non Final Office Action mailed Feb. 1, 2013", 10 pgs.

"U.S. Appl. No. 12/919,905, Response filed Jul. 10, 2013 to Final Office Action mailed May 10, 2013", 12 pgs.

"U.S. Appl. No. 12/919,905, Restriction Requirement mailed Dec. 12, 2012", 9 pgs.

"U.S. Appl. No. 12/919,905, Supplemental Preliminary Amendment mailed Jan. 11, 2011", 3 pgs.

"U.S. Appl. No. 12/919,905, Supplemental Preliminary Amendment mailed Mar. 17, 2011", 3 pgs.

"U.S. Appl. No. 13/318,179, Non Final Office Action mailed Apr. 29, 2013", 16 pgs.

(56) References Cited

OTHER PUBLICATIONS

"U.S. Appl. No. 13/318,179, Preliminary Amendment filed Oct. 31, 2011", 8 pgs.
"U.S. Appl. No. 13/318,179, Response filed Mar. 6, 2013 to Restriction Requirement mailed Feb. 14, 2013", 7 pgs.
"U.S. Appl. No. 13/318,179, Restriction Requirement mailed Feb. 14, 2013", 7 pgs.
"U.S. Appl. No. 13/318,179, Supplemental Preliminary Amendment filed Jan. 16, 2012", 4 pgs.
"U.S. Appl. No. 13/569,465, Preliminary Amendment filed Aug. 8, 2012", 9 pgs.
"U.S. Appl. No. 13/569,465, Restriction Requirement mailed Dec. 21, 2012", 10 pgs.
"U.S. Appl. No. 13/589,603, Examiner Interview Summary mailed Jul. 12, 2013", 3 pgs.
"U.S. Appl. No. 13/589,603, Final Office Action mailed Oct. 18, 2013", 9 pgs.
"U.S. Appl. No. 13/589,603, Non Final Office Action mailed Apr. 29, 2013", 15 pgs.
"U.S. Appl. No. 13/589,603, Notice of Allowance mailed Jan. 27, 2014", 11 pgs.
"U.S. Appl. No. 13/589,603, Preliminary Amendment filed Aug. 20, 2012", 4 pgs.
"U.S. Appl. No. 13/589,603, Response filed Jan. 7, 2013 to Restriction Requirement mailed Dec. 7, 2012", 11 pgs.
"U.S. Appl. No. 13/589,603, Response filed Jan. 7, 2014 to Final Office Action mailed Oct. 18, 2013", 14 pgs.
"U.S. Appl. No. 13/589,603, Response filed Jul. 26, 2013 to Non Final Office Action mailed Apr. 29, 2013", 12 pgs.
"U.S. Appl. No. 13/589,603, Restriction Requirement mailed Dec. 7, 2012", 8 pgs.
"U.S. Appl. No. 13/606,271, Advisory Action mailed Feb. 16, 2016", 5 pgs.
"U.S. Appl. No. 13/606,271, Advisory Action mailed Mar. 1, 2016", 8 pgs.
"U.S. Appl. No. 13/606,271, Advisory Action mailed Apr. 25, 2014", 10 pgs.
"U.S. Appl. No. 13/606,271, Advisory Action mailed Jul. 10, 2014", 3 pgs.
"U.S. Appl. No. 13/606,271, Examiner Interview Summary mailed Apr. 25, 2014", 2 pgs.
"U.S. Appl. No. 13/606,271, Final Office Action mailed Oct. 13, 2015", 18 pgs.
"U.S. Appl. No. 13/606,271, Final Office Action mailed Dec. 18, 2013", 54 pgs.
"U.S. Appl. No. 13/606,271, Non Final Office Action mailed Mar. 6, 2015", 42 pgs.
"U.S. Appl. No. 13/606,271, Non Final Office Action mailed Jun. 10, 2013", 48 pgs.
"U.S. Appl. No. 13/606,271, Pre Appeal Brief Request filed Jun. 18, 2014", 5 pgs.
"U.S. Appl. No. 13/606,271, Response filed Apr. 17, 2014 to Final Office Action mailed Dec. 18, 2013", 18 pgs.
"U.S. Appl. No. 13/606,271, Response filed May 1, 2013 to Restriction Requirement mailed Apr. 4, 2013", 11 pgs.
"U.S. Appl. No. 13/606,271, Response filed Aug. 18, 2014 to Advisory Action mailed Jul. 10, 2014", 18 pgs.
"U.S. Appl. No. 13/606,271, Response filed Sep. 8, 2015 to Non Final Office Action mailed Mar. 6, 2015", 10 pgs.
"U.S. Appl. No. 13/606,271, Response filed Nov. 11, 2013 to Non Final Office Action mailed Jun. 10, 2013", 13 pgs.
"U.S. Appl. No. 13/606,271, Restriction Requirement mailed Apr. 4, 2013", 8 pgs.
"U.S. Appl. No. 13/606,271, Supplemental Amendment filed Jun. 18, 2014", 4 pgs.
"U.S. Appl. No. 13/606,271, Response filed Feb. 16, 2016 to Final Office Action mailed Oct. 13, 2015", 12 pgs.
"U.S. Appl. No. 14/064,615, Preliminary Amendment mailed Oct. 29, 2013", 6 pgs.

"U.S. Appl. No. 14/189,746, Non Final Office Action mailed Apr. 27, 2015", 20 pgs.
"U.S. Appl. No. 14/189,746, Preliminary Amendment filed Feb. 26, 2014", 9 pgs.
"U.S. Appl. No. 14/266,313, Non Final Office Action mailed Mar. 10, 2016", 6 pgs.
"U.S. Appl. No. 14/266,313, Notice of Allowability mailed Oct. 17, 2016", 5 pgs.
"U.S. Appl. No. 14/266,313, Notice of Allowance mailed Aug. 30, 2016", 8 pgs.
"U.S. Appl. No. 14/266,313, Preliminary Amendment filed May 30, 2014", 5 pgs.
"U.S. Appl. No. 14/266,313, Response filed Aug. 10, 2016 to Non Final Office Action mailed Mar. 10, 2016", 7 pgs.
"U.S. Appl. No. 14/886,691, Non Final Office Action mailed Mar. 22, 2016", 21 pgs.
"U.S. Appl. No. 15/096,675, Non Final Office Action mailed Jun. 22, 2017", 42 pgs.
"U.S. Appl. No. 15/096,675, Preliminary Amendment Filed Jul. 28, 2016", 5 pgs.
"U.S. Appl. No. 15/096,675, Response filed May 1, 2017 to Restriction Requirement mailed Jan. 30, 2017", 6 pgs.
"U.S. Appl. No. 15/096,675, Restriction Requirement mailed Jan. 30, 2017", 7 pgs.
"U.S. Appl. No. 15/243,682, Final Office Action mailed Oct. 27, 2016", 21 pgs.
"U.S. Appl. No. 15/397,076, Final Office Action mailed Jun. 24, 2019", 8 pgs.
"U.S. Appl. No. 15/397,076, Non Final Office Action mailed Jan. 25, 2019", 12 pgs.
"U.S. Appl. No. 15/397,076, Notice of Allowance mailed Nov. 6, 2019", 10 pgs.
"U.S. Appl. No. 15/397,076, Response filed Oct. 10, 2018 to Restriction Requirement mailed Jun. 13, 2018", 8 pgs.
"U.S. Appl. No. 15/397,076, Response filed Oct. 24, 2019 to Final Office Action mailed Jun. 24, 2019", 7 pgs.
"U.S. Appl. No. 15/397,076, Response filed May 21, 2019 to Non Final Office Action mailed Jan. 25, 2019", 9 pgs.
"U.S. Appl. No. 15/397,076, Restriction Requirement mailed Jun. 13, 2018", 8 pgs.
"U.S. Appl. No. 15/417,933, Final Office Action mailed Jun. 16, 2017", 21 pgs.
"U.S. Appl. No. 15/417,933,, Examiner Interview Summary filed Oct. 13, 2017", 2 pgs.
"U.S. Appl. No. 15/783,676, Final Office Action mailed Jun. 13, 2018", 20 pgs.
"U.S. Appl. No. 15/848,079, Final Office Action mailed Apr. 20, 2020", 26 pgs.
"U.S. Appl. No. 15/848,079, Final Office Action mailed Jul. 23, 2019", 27 pgs.
"U.S. Appl. No. 15/848,079, Non Final Office Action mailed Feb. 19, 2019", 24 pgs.
"U.S. Appl. No. 15/848,079, Response Filed Nov. 25, 2019 to Final Office Action Mailed Jul. 23, 2019", 11 pgs.
"U.S. Appl. No. 15/848,079, Response filed Dec. 21, 2018 to Restriction Requirement mailed Oct. 22, 2018", 7 pgs.
"U.S. Appl. No. 15/848,079, Response filed May 21, 2019 to Non Final Office Action mailed Feb. 19, 2019", 10 pgs.
"U.S. Appl. No. 15/848,079, Restriction Requirement mailed Oct. 22, 2018", 5 pgs.
"U.S. Appl. No. 16/133,234, Final Office Action mailed Jun. 5, 2019", 11 pgs.
"U.S. Appl. No. 16/133,234, Non Final Office Action mailed Nov. 23, 2018", 16 pgs.
"U.S. Appl. No. 16/133,234, Notice of Allowance mailed Aug. 27, 2019", 9 pgs.
"U.S. Appl. No. 16/133,234, Preliminary Amendment filed Sep. 18, 2018", 9 pgs.
"U.S. Appl. No. 16/133,234, Response filed Feb. 14, 2019 to Non Final Office Action mailed Nov. 23, 2018", 7 pgs.
"U.S. Appl. No. 16/133,234, Response filed Jul. 23, 2019 to Final Office Action mailed Jun. 5, 2019", 5 pgs.

(56) References Cited

OTHER PUBLICATIONS

"U.S. Appl. No. 16/276,479, Final Office Action mailed Oct. 31, 2019", 14 pgs.
"U.S. Appl. No. 16/276,479, Non Final Office Action mailed Jun. 12, 2019", 14 pgs.
"U.S. Appl. No. 16/276,479, Notice of Allowance mailed Nov. 22, 2019", 7 pgs.
"U.S. Appl. No. 16/276,479, Preliminary Amendment Filed Feb. 15, 2019", 9 pgs.
"U.S. Appl. No. 16/276,479, Response filed Oct. 14, 2019 to Non-Final Office Action mailed Jun. 12, 2019", 7 pgs.
"U.S. Appl. No. 16/276,479, Response filed Nov. 12, 2019 to Final Office Action mailed Oct. 31, 2019", 7 pgs.
"U.S. Appl. No. 16/784,051 Preliminary Amendment filed Feb. 10, 2020", 5 pgs.
"U.S. Appl. No. 16/784,051, Non Final Office Action mailed Dec. 6, 2021", 6 pgs.
"U.S. Appl. No. 16/784,051, Notice of Allowance mailed Jan. 12, 2022", 5 pgs.
"U.S. Appl. No. 16/784,051, Response filed Dec. 14, 2021 to Non Final Office Action mailed Dec. 6, 2021", 6 pgs.
"U.S. Appl. No. 16/807,379 Preliminary Amendment filed Mar. 5, 2020", 4 pgs.
"U.S. Appl. No. 16/807,379, Non Final Office Action mailed Sep. 17, 2020", 14 pgs.
"U.S. Appl. No. 16/807,379, Notice of Allowance mailed Jan. 1, 2021", 7 pgs.
"U.S. Appl. No. 16/807,379, Response filed Dec. 16, 2020 to Non Final Office Action mailed Sep. 17, 2020", 9 pgs.
"U.S. Appl. No. 16/931,813, Examiner Interview Summary mailed Nov. 5, 2021", 2 pgs.
"U.S. Appl. No. 16/931,813, Non Final Office Action mailed Apr. 19, 2021", 23 pgs.
"U.S. Appl. No. 16/931,813, Notice of Allowance mailed Feb. 4, 2022", 8 pgs.
"U.S. Appl. No. 16/931,813, Preliminary Amendment filed Sep. 29, 2020", 5 pgs.
"U.S. Appl. No. 16/931,813, Response filed Jan. 12, 2021 to Restriction Requirement mailed Oct. 14, 2020", 7 pgs.
"U.S. Appl. No. 16/931,813, Response filed Oct. 19, 2021 to Non Final Office Action mailed Apr. 19, 2021", 7 pgs.
"U.S. Appl. No. 16/931,813, Restriction Requirement mailed Oct. 14, 2020", 6 pgs.
"U.S. Appl. No. 17/061,749, Examiner Interview Summary mailed May 7, 2021", 3 pgs.
"U.S. Appl. No. 17/061,749, Non Final Office Action mailed Feb. 8, 2021", 10 pgs.
"U.S. Appl. No. 17/061,749, Notice of Allowance mailed May 20, 2021", 7 pgs.
"U.S. Appl. No. 17/061,749, Response filed May 5, 2021 to Non Final Office Action mailed Feb. 8, 2021", 7 pgs.
"U.S. Appl. No. 17/061,749, Response filed Dec. 30, 2020 to Restriction Requirement Received—Prioritized Examination mailed Dec. 24, 2020", 6 pgs.
"U.S. Appl. No. 17/061,749, Restriction Requirement Received—Prioritized Examination mailed Dec. 24, 2020", 5 pgs.
"U.S. Appl. No. 17/061,749, Supplemental Notice of Allowability mailed Aug. 18, 2021", 2 pgs.
"U.S. Appl. No. 17/301,660, Non Final Office Action mailed Nov. 9, 2022", 19 pgs.
"U.S. Appl. No. 17/301,660, Preliminary Amendment filed Jun. 21, 2021", 5 pgs.
"Australian Application Serial No. 2007333656, Office Action mailed Jun. 21, 2012", 4 pgs.
"Australian Application Serial No. 2007333656, Office Action mailed Dec. 13, 2012", 4 pgs.
et al., "Australian Application Serial No. 2007333656, Response filed Oct. 25, 2012 to Office Action mailed Jun. 21, 2012", 27 pgs.
"Australian Application Serial No. 2009219174, First Examiner Report mailed Jan. 8, 2014", 3 pgs.
"Australian Application Serial No. 2009219174, Response filed Feb. 28, 2014 to Office Action mailed Jan. 8, 2014", 41 pgs.
"Australian Application Serial No. 2011274355, First Examiner Report mailed Nov. 6, 2015", 6 pgs.
"Australian Application Serial No. 2011274355, Response filed Jun. 1, 2016 to Office Action mailed Nov. 6, 2015", 21 pgs.
"Australian Application Serial No. 2011274355, Response filed Oct. 7, 2016 to Subsequent Examiners Report mailed Jun. 29, 2016", 13 pgs.
"Australian Application Serial No. 2011274355, Subsequent Examiners Report mailed Jun. 29, 2016", 5 pgs.
"Brazilian Application Serial No. PI 0908425-8, Office Action mailed Feb. 12, 2020", w/ English Translation, 7 pgs.
"Brazilian Application Serial No. PI 0908425-8, Response filed May 18, 2020 to Office Action mailed Feb. 12, 2020", w/ English Claims, 191 pgs.
"Canadian Application Serial No. 2,673,481, Office Action mailed Sep. 12, 2013", 5 pgs.
"Canadian Application Serial No. 2,716,498, Office Action mailed Feb. 25, 2016", 4 pgs.
"Canadian Application Serial No. 2,716,498, Office Action mailed Mar. 31, 2017", 3 pgs.
"Canadian Application Serial No. 2,716,498, Office Action mailed May 7, 2019", 3 pgs.
"Canadian Application Serial No. 2,716,498, Office Action mailed Dec. 31, 2014", 4 pgs.
"Canadian Application Serial No. 2,716,498, Response filed Jun. 30, 2015 to Office Action mailed Dec. 31, 2014", 34 pgs.
"Canadian Application Serial No. 2,716,498, Response filed Sep. 3, 2016 to Office Action mailed Feb. 25, 2016", (English Translation of Claims), 21 pgs.
"Canadian Application Serial No. 2,716,498, Response filed Oct. 2, 2017 to Office Action mailed Mar. 31, 2017", 31 pgs.
"Canadian Application Serial No. 2,716,498, Response filed Nov. 7, 2019 to Office Action mailed May 7, 2019", 22 pgs.
"Canadian Application Serial No. 2,848,211, Final Examiner's Report mailed Dec. 17, 2021", 6 pgs.
"Canadian Application Serial No. 2,848,211, Office Action mailed Jan. 4, 2021", 6 pgs.
"Canadian Application Serial No. 2,848,211, Office Action mailed Apr. 18, 2018", 5 pgs.
"Canadian Application Serial No. 2,848,211, Office Action mailed Jun. 3, 2019", 4 pgs.
"Canadian Application Serial No. 2,848,211, Response Filed Apr. 14, 2022 to Final Examiner's Report mailed Dec. 17, 2021", 7 pgs.
"Canadian Application Serial No. 2,848,211, Response filed May 3, 2021 to Office Action mailed Jan. 4, 2021", 18 pgs.
"Canadian Application Serial No. 2,848,211, Response filed Oct. 18, 2018 to Office Action mailed Apr. 18, 2018", 26 pgs.
"Canadian Application Serial No. 2,848,211, Response filed Dec. 3, 2019 to Office Action mailed Jun. 3, 2019", 24 pgs.
"Canadian Application Serial No. 2,848,211, Voluntary Amendment filed Dec. 13, 2022", 5 pgs.
"Chinese Application Serial No. 200780051498.2, Non Final Office Action mailed Apr. 13, 2011", 14 pgs.
"Chinese Application Serial No. 200780051498.2, Office Action mailed Jan. 6, 2012", 10 pgs.
"Chinese Application Serial No. 200780051498.2, Office Action mailed Jul. 30, 2012", w/ English Translation, 7 pgs.
"Chinese Application Serial No. 200780051498.2, Office Action Response filed Oct. 28, 2011", 6 pgs.
"Chinese Application Serial No. 200780051498.2, Response filed May 18, 2012 to Office Action mailed Jan. 6, 2012", 5 pgs.
"Chinese Application Serial No. 200780051498.2, Response filed Oct. 10, 2012 to Office Action mailed Jul. 30, 2012", With English Claims, 6 pgs.
"Chinese Application Serial No. 200980115220.6, Amendment filed Jul. 29, 2011", (w/ English Translation), 41 pgs.
"Chinese Application Serial No. 200980115220.6, Notice of Reexamination mailed Sep. 14, 2016", (English Translation), 7 pgs.
"Chinese Application Serial No. 200980115220.6, Office Action mailed Jan. 14, 2013", (w/ English Translation), 15 pgs.

(56) References Cited

OTHER PUBLICATIONS

"Chinese Application Serial No. 200980115220.6, Office Action mailed Aug. 2, 2013", 6 pgs.
"Chinese Application Serial No. 200980115220.6, Office Action mailed Aug. 5, 2014", (w/ English Translation), 20 pgs.
"Chinese Application Serial No. 200980115220.6, Office Action mailed Dec. 3, 2014", w/ English Claims, 47 pgs.
"Chinese Application Serial No. 200980115220.6, Office Action mailed Dec. 18, 2013", (w/ English Translation), 13 pgs.
"Chinese Application Serial No. 200980115220.6, Office Action mailed Jun. 3, 2015", w/ English Translation, 9 pgs.
"Chinese Application Serial No. 200980115220.6, Response filed Apr. 30, 2014 to Office Action mailed Dec. 18, 2013", (w/ English Translation of Amended Claims), 59 pgs.
"Chinese Application Serial No. 200980115220.6, Response filed May 29, 2013 to Office Action mailed Jan. 14, 2013", (Amendments not filed), 3 pgs.
"Chinese Application Serial No. 200980115220.6, Response filed Oct. 17, 2013 to Office Action mailed Oct. 7, 2013", (Amendments not filed), 30 pgs.
"Chinese Application Serial No. 200980115220.6, Response filed Oct. 20, 2014 to Office Action mailed Aug. 5, 2014", (w/ English Translation of Amended Claims), 66 pgs.
"Chinese Application Serial No. 200980115220.6, Response filed Apr. 20, 2015 to Office Action mailed Dec. 3, 2014", in English, 30 pgs.
"Costa Rican Application Serial No. 10938, Office Action mailed Apr. 8, 2010", 6 pgs.
"Costa Rican Application Serial No. 10938, Response to Opposition filed May 12, 2010", 6 pgs.
"DbSNP-rs1176719", Reference SNP (rs) Report, [Online]. [Archived Feb. 27, 2019]. Retrieved from the Internet: <URL: https://www.ncbi.nlm.nih.gov/snp/rs1176719>, (Released Oct. 2, 2018), 10 pgs.
"DbSNP-rs1150226", Reference SNP (rs) Report, [Online]. [Accessed Feb. 7, 2019]. Retrieved from the Internet: <URL: https://www.ncbi.nlm.nih.gov/snp/rs1150226>, (Released Oct. 2, 2018), 7 pgs.
"Definition of Sequela", Merriam-Webster, [Online]. Retrieved from Internet: <URL: http://www.merriam-webster.com/dictionary/sequelae>, (Jan. 31, 2013), 2 pgs.
"Eurasian Application Serial No. 2010001389, Office Action mailed Sep. 19, 2012", With English Translation, 2 pgs.
"Eurasian Application Serial No. 201001389, Response filed Feb. 12, 2013 to Office Action mailed Sep. 19, 2012", 51 pgs.
"Eurasian Application Serial No. 201390017, Office Action mailed Nov. 13, 2014", w/ English Translation, 3 pgs.
"Eurasian Application Serial No. 201390017, Response filed May 15, 2015 to Office Action mailed Nov. 13, 2014", w/ English Claims, 24 pgs.
"Eurasian Application Serial No. 201490548, Notice of Allowance mailed Jan. 19, 2017", w/English Claims, 8 pgs.
"Eurasian Application Serial No. 201490548, Office Action mailed Mar. 10, 2016", W/ English Translation, 2 pgs.
"Eurasian Application Serial No. 201490548, Office Action mailed May 15, 2014", w/ English Translation, 2 pgs.
"Eurasian Application Serial No. 201490548, Response filed Aug. 4, 2016 to Office Action mailed Mar. 10, 2016", w/English Claims, 89 pgs.
"Eurasian Application Serial No. 201490548, Response filed Sep. 15, 2014 to Office Action mailed May 15, 2014", not in English, 1 pg.
"European Application Serial No. 09714591.6, Response filed Sep. 21, 2012 to Office Action mailed Jun. 28, 2012", 14 pgs.
"European Application Serial No. 07869501.2, Office Action Filed Mar. 24, 2011", 3 pgs.
"European Application Serial No. 07869501.2, Office Action mailed May 31, 2010", 1 pg.
"European Application Serial No. 07869501.2, Response filed Mar. 15, 2011 to Noting of Loss of Rights mailed Jan. 18, 2011", 5 pgs.
"European Application Serial No. 07869501.2, Response filed Aug. 31, 2009 to Communication dated Aug. 11, 2009", 5 pgs.
"European Application Serial No. 07869501.2, Supplemental European Search Report mailed Feb. 25, 2010", 15 pgs.
"European Application Serial No. 09714591.6, Office Action mailed Oct. 5, 2010", 2 pgs.
"European Application Serial No. 09714591.6, Office Action mailed Jun. 28, 2012", 6 pgs.
"European Application Serial No. 09714591.6, Response filed Jan. 5, 2012 to Extended Search Report mailed Aug. 25, 2011", 15 pgs.
"European Application Serial No. 09714591.6, Response filed Nov. 2, 2010 to Office Action mailed Oct. 5, 2010", 8 pgs.
"European Application Serial No. 10717322.1, Office Action mailed Aug. 29, 2012", 5 pgs.
"European Application Serial No. 11801503.1, Extended European Search Report mailed Nov. 27, 2013", 11 pgs.
"European Application Serial No. 12170027.2, Extended European Search Report mailed Jan. 14, 2013", 6 pgs.
"European Application Serial No. 12830779.0, Extended European Search Report mailed May 6, 2015", 13 pgs.
"European Application Serial No. 12830779.0, Office Action mailed Apr. 9, 2014", 3 pgs.
"European Application Serial No. 12830779.0, Response filed Sep. 25, 2014 to Office Action mailed Apr. 9, 2014", 9 pgs.
"European Application Serial No. 14173142.2, Communication Pursuant to Article 94(3) EPC mailed May 13, 2016", 3 pgs.
"European Application Serial No. 14173142.2, Communication pursuant to Rule 69 EPC mailed Nov. 17, 2014", 4 pgs.
"European Application Serial No. 14173142.2, Extended European Search Report mailed Oct. 10, 2014", 9 pgs.
"European Application Serial No. 14173142.2, Response filed May 11, 2015 to Communication pursuant to Rule 69 EPC mailed Nov. 17, 2014", 10 pgs.
"European Application Serial No. 15197075.3, Extended European Search Report mailed Aug. 12, 2016", 15 pgs.
"European Application Serial No. 09714591.6, Extended European Search Report mailed Jul. 28, 2011", 10 pgs.
"Friday Abstracts ED—Sanacora Gerard; Duman Ronald S", Biological Psychiatry, Elsevier Science, New York vol. 65, No. 8, (Apr. 15, 2009), 82S-162S.
"Hypnotic cure for Drunkards in Clinic", New York Times, (Dec. 1908), 1 pg.
"Indian Application Serial No. 4727/DELNP/2009, Office Action mailed Sep. 29, 2014", 2 pgs.
"Indian Application Serial No. 6807/DELNP/2010, First Examiner Report mailed Dec. 22, 2016", 14 pgs.
"International Application Serial No. PCT.US2011/0223481, Written Opinion mailed Jul. 27, 2011", 5 pgs.
"International Application Serial No. PCT/US07/88100, International Search Report mailed May 16, 2008", 1 pg.
"International Application Serial No. PCT/US07/88100, Written Opinion mailed May 16, 2008", 11 pgs.
"International Application Serial No. PCT/US08/52628, International Search Report mailed Aug. 19, 2008", 3 pgs.
"International Application Serial No. PCT/US08/52628, Written Opinion mailed Aug. 19, 2008", 5 pgs.
"International Application Serial No. PCT/US09/35420, International Search Report mailed Oct. 5, 2009", 5 pgs.
"International Application Serial No. PCT/US09/35420, Written Opinion mailed Oct. 5, 2009", 20 pgs.
"International Application Serial No. PCT/US2008/052628, International Preliminary Report on Patentability mailed Aug. 4, 2009", 6 pgs.
"International Application Serial No. PCT/US2008/064232, International Search Report mailed Aug. 15, 2008", 1 pg.
"International Application Serial No. PCT/US2008/064232, Written Opinion mailed Aug. 15, 2008", 8 pgs.
"International Application Serial No. PCT/US2008/073738, International Preliminary Report on Patentability mailed Feb. 24, 2010", 6 pgs.
"International Application Serial No. PCT/US2008/073738, Written Opinion mailed Nov. 12, 2008", 5 pgs.
"International Application Serial No. PCT/US2009/035420, International Preliminary Report on Patentability mailed Sep. 10, 2010", 21 pgs.

(56) References Cited

OTHER PUBLICATIONS

"International Application Serial No. PCT/US2010/001273, International Preliminary Report on Patentability mailed Jan. 4, 2011", 16 pgs.
"International Application Serial No. PCT/US2010/001273, Search Report mailed Aug. 24, 2010", 10 pgs.
"International Application Serial No. PCT/US2010/001273, Written Opinion mailed Aug. 24, 2010", 13 pgs.
"International Application Serial No. PCT/US2011/023481, International Preliminary Report on Patentability mailed Jul. 27, 2011", 10 pgs.
"International Application Serial No. PCT/US2011/023481, International Search Report mailed Jul. 27, 2011", 3 pgs.
"International Application Serial No. PCT/US2011/042823, International Preliminary Report on Patentability mailed Jan. 17, 2013", 7 pgs.
"International Application Serial No. PCT/US2011/042823, International Search Report mailed Dec. 6, 2011", 4 pgs.
"International Application Serial No. PCT/US2011/042823, Written Opinion mailed Dec. 6, 2011", 5 pgs.
"International Application Serial No. PCT/US2012/054090, International Preliminary Report on Patentability mailed Mar. 20, 2014", 7 pgs.
"International Application Serial No. PCT/US2012/054090, International Search Report mailed Feb. 5, 2013", 5 pgs.
"International Application Serial No. PCT/US2012/054090, Invitation to Pay Additional Fees mailed Nov. 15, 2012", 2 pgs.
"International Application Serial No. PCT/US2012/054090, Written Opinion mailed Feb. 5, 2013", 5 pgs.
"Israel Application Serial No. 223996, Office Action mailed May 4, 2017", English Translation, 3 pgs.
"Israel Application Serial No. 223996, Office Action mailed Jun. 7, 2018", w/ English translation, 5 pgs.
"Israel Application Serial No. 223996, Response filed Oct. 2, 2017 to Office Action mailed May 4, 2017", 5 pgs.
"Israel Application Serial No. 223996, Response filed Oct. 4, 2028 to Office Action mailed Jun. 7, 2018", w/o Translation, 6 pgs.
"Israel Application Serial No. 262874, Office Action mailed Mar. 14, 2019", w/ English translation, 9 pgs.
"Israel Application Serial No. 262874, Office Action mailed Jun. 3, 2020", w/o English Translation, 3 pgs.
"Israel Application Serial No. 278149, Office Action mailed Jun. 20, 2021", w/ English translation, 8 pgs.
"Israel Application Serial No. 278149, Office Action mailed Jul. 28, 2022", w/ English translation, 7 pgs.
"Israel Application Serial No. 278149, Response filed Nov. 21, 2021 to Office Action mailed Jun. 20, 2021", w/English Claims, 8 pgs.
"Israeli Application Serial No. 207822, Non Final Office Action dated Aug. 25, 2011", 3 pgs.
"Israeli Application Serial No. 207822, Office Action mailed Jan. 20, 2014", 1 pg.
"Israeli Application Serial No. 207822, Office Action mailed Jul. 9, 2013", English Translation, 2 pgs.
"Israeli Application Serial No. 207822, Office Action mailed Sep. 21, 2014", 2 pg.
"Israeli Application Serial No. 207822, Office Action mailed Nov. 13, 2012", 2 pgs.
"Israeli Application Serial No. 207822, Response filed Mar. 19, 2015 to Office Action mailed Sep. 21, 2014", 2 pgs.
"Israeli Application Serial No. 207822, Response filed Apr. 7, 2013 to Office Action mailed Nov. 13, 2012", English Translation, 9 pgs.
"Israeli Application Serial No. 207822, Response filed Jun. 19, 2014 to Office Action mailed Jan. 20, 2014", 9 pgs.
"Israeli Application Serial No. 207822, Response filed Oct. 29, 2013 to Office Action mailed Jul. 9, 2013", English Translation, 5 pgs.
"Israeli Application Serial No. 223996, Notification Prior to Examination mailed Dec. 15, 2014", w/ English Translation, 3 pgs.
"Israeli Application Serial No. 223996, Office Action mailed Oct. 13, 2015", 3 pgs.

"Israeli Application Serial No. 223996, Response filed Apr. 13, 2016 to Office Action mailed Oct. 13, 2015", 15 pgs.
"Israeli Application Serial No. 262874, Response filed Jul. 14, 2019 to Office Action mailed Mar. 14, 2019", w/English Claims, 4 pgs.
"Israeli Application Serial No. 278149, Response filed Nov. 20, 2022 to Office Action mailed Jul. 28, 2022", w/ English claims, 8 pgs.
"Japanese Application Serial No. 2009-543177, Amendment filed Dec. 1, 2011", 2 pgs.
"Japanese Application Serial No. 2009-543177, Office Action mailed Dec. 10, 2012", 5 pgs.
"Japanese Application Serial No. 2010-522982, Amendment filed May 10, 2011", 8 pgs.
"Japanese Application Serial No. 2010-548893, Amendment filed Feb. 21, 2012", 61 pgs.
"Japanese Application Serial No. 2010-548893, Examiners Decision of Final Refusal mailed Apr. 8, 2014", 3 pgs.
"Japanese Application Serial No. 2010-548893, Office Action mailed Nov. 27, 2013", w/English Translation, 9 pgs.
"Japanese Application Serial No. 2010-548893, Response filed Feb. 21, 2014 to Office Action mailed Nov. 27, 2013", w/English Claims, 28 pgs.
"Korean Application Serial No. 10-2010-7021452, Office Action mailed Feb. 22, 2016", 7 pgs.
"Korean Application Serial No. 10-2010-7021452, Response filed Apr. 22, 2016 to Office Action mailed Feb. 22, 2016", w/English Claims, 18 pgs.
"Mexican Application Serial No. MX/a/2009/006672, Office Action mailed Apr. 12, 2012", 3 pgs.
"Mexican Application Serial No. MX/a/2009/006672, Office Action mailed Sep. 6, 2011", 2 pgs.
"Mexican Application Serial No. MX/a/2009/006672, Office Action mailed Dec. 17, 2012", 3 pgs.
"Mexican Application Serial No. MX/a/2009/006672, Response filed Jan. 31, 2012 to Office Action mailed Sep. 6, 2011", 3 pgs.
"Mexican Application Serial No. MX/a/2009/006672, Response filed Aug. 15, 2012 to Non Final Office Action dated Apr. 16, 2012", w/ English Claims, 4 pgs.
"Mexican Application Serial No. MX/a/2010/009509, Office Action mailed Mar. 13, 2013", 3 pgs.
"Mexican Application Serial No. MX/a/2010/009509, Response filed May 17, 2013 to Office Action mailed Mar. 13, 2013", 12 pgs.
"NCBI Reference Cluster Report 17614942", Retrieved Nov. 28, 2011, [Online]. Retrieved from the Internet: <URL: http://ncbi.nlm.nih.gov>, (Aug. 2004), 2 pgs.
"NCBI Reference SNP Cluster Report 10160548", Retrieved Nov. 28, 2011, [Online]. Retrieved from the Internet: <URL: http://ncbi.nlm.nih.gov>, (Nov. 2003), 3 pgs.
"NCBI Reference SNP Cluster Report 1176746", Retrieved Nov. 28, 2011, [Online]. Retrieved from the Internet: <URL: http://www.ncbi.nlm.nih.gov>, (Oct. 2000), 3 pgs.
"NCBI Reference SNP Cluster Report 12270070", Retrieved Nov. 28, 2011, [Online]. Retrieved from the Internet: <URL: http://www.ncbi.nlm.nih.gov>, (Feb. 2004), 2 pgs.
"New Zealand Application Serial No. 588037, Office Action Response Filed May 28, 2012", 41 Pgs.
"New Zealand Application Serial No. 588037, Response filed Jul. 16, 2012 to Examiner Report mailed Jun. 22, 2012", 40 pgs.
"New Zealand Application Serial No. 588037, Second Examination Report mailed Jun. 22, 2012", 12 pgs.
"New Zealand Application Serial No. 605709, First Examiner Report mailed Sep. 12, 2013", 2 pgs.
"New Zealand Application Serial No. 605709, Office Action mailed Feb. 21, 2014", 1 pg.
"New Zealand Application Serial No. 605709, Response filed Feb. 18, 2014 to First Examiner Report mailed Sep. 12, 2013", 158 pgs.
"New Zealand Application Serial No. 605709, Response filed Feb. 18, 2014 to Office Action", 158 pgs.
"New Zealand Application Serial No. 621352, First Examiner's Report mailed Feb. 21, 2014", 2 pgs.
"New Zealand Application Serial No. 621352, Response filed Apr. 10, 2015 to First Examiner's Report mailed Feb. 21, 2014", 155 pgs.

(56) References Cited

OTHER PUBLICATIONS

"New Zealand Application Serial No. 621356, First Examiner's Report mailed Feb. 21, 2014", 2 pgs.
"New Zealand Application Serial No. 621356, Response filed Apr. 10, 2015 to First Examiner's Report mailed Feb. 21, 2014", 157 pgs.
"New Zealand Application Serial No. 588037, First Examiner Report mailed Mar. 21, 2011", 2 Pgs.
"Nicaragua Application Serial No. 2009-000124, Office Action mailed Jun. 25, 2012", 5 pgs.
"SLC6A4 gene", Genetics Home Reference, [Online]. [Accessed Feb. 7, 2019]. Retrieved from the Internet: <URL: https://ghr.nlm.nih.gov/gene/SLC6A4>, (Feb. 5, 2019), 3 pgs.
"South African Application Serial No. 2010/06485, Amendment filed Nov. 10, 2013", 33 pgs.
"SS23605662", (for rsl 150226,NCBI, dbSNP), [Online]. Retrieved from the Internet: <URL: http://www.ncbi.nlm.nih.gov/projects/SNP/snp_ss.cgi?subsnp_id=23605662>, (2004), 2 pgs.
"Ukraine Application Serial No. A201300520, Office Action mailed Jan. 3, 2017", 12 pgs.
"Ukraine Application Serial No. A201300520, Office Action mailed Oct. 21, 2015", 14 pgs.
"Ukraine Application Serial No. A201300520, Response filed Jun. 15, 2016 to Office Action mailed Oct. 22, 2015", w/English Claims, 9 pgs.
"Ukraine Application Serial No. A201300520, Response filed Sep. 5, 2017 to Office Action mailed Jan. 3, 2017", W/English Claims, 9 pgs.
"Ukrainian Application Serial No. 201011545, Office Action mailed May 30, 2013", English Translation, 7 pgs.
"Ukrainian Application Serial No. 201011545, Response filed Jul. 11, 2013 to Office Action mailed May 30, 2013", w/English Claims, 35 pgs.
"Ukrainian Application Serial No. A201300520, Voluntary Amendment mailed Jul. 17, 2014", w/ English Claims, 7 pgs.
Ait-Daoud, Nassima, et al., "Combining ondansetron and naltrexone reduces craving among biologically predisposed alcoholics: preliminary clinical evidence", Psychopharmacology, 154(1), (Feb. 2001), 23-27.
Anton, R. F., et al., "Structured Psychosocial Interventions Focused on Adherence Combined with Naltrexone Make Drinking Relapse Less Likely", Annals of Internal Medicine, 134(5), (2001), 388-389.
Balldin, J, et al., "A 6-Month Controlled Naltrexone Study: Combined Effect With Cognitive Behavioral Therapy in Outpatient Treatment of Alcohol Dependence", Alcoholism: Clinical and Experimental Research, vol. 27(7) Abstract only, (2003), 1142-1149.
Bankole, Johnson A, et al., "Determination of genotype combinations that can predict the outcome of the treatment of alcohol dependence using the 5-HT(3) antagonist ondansetron", The American Journal of Psychiatry, 170, (Sep. 1, 2013), 1020-1031.
Basu, A., et al., "Effect of Type 2 Diabetes on Meal Glucose Fluxes and Insulin Secretion", Diabetes, 53(suppl. 2), (2004), A579.
Benner, et al., "Evolution, language and analogy in functional genomics", Trends in Genetics, vol. 17, (2001), 414-418.
Bergman, R. N, et al., "Assessment of insulin sensitivity in vivo", Endocr Rev., 6(1), (Winter, 1985), 45-86.
Bergman, R. N, "The minimal model of glucose regulation: a biography", Adv Exp Med Biol., 537, (2003), 1-19.
Bergman, Richard, et al., "Minimal Model-Based Insulin Sensitivity Has Greater Heritability and a Different Genetic Basis Than Homeostasis Model Assessment or Fasting Insulin", Diabetes 52, (2003), 2168-2174.
Bergman, Richard, et al., "Quantitative estimation of insulin sensitivity", Am J Physiol., 236, (Jun. 1979), E667-E677.
Breda, E, et al., "Oral glucose tolerance test minimal model indexes of beta-cell function and insulin sensitivity", Diabetes 50, (2001), 150-158.
Castro, L. A, et al., "The pharmacologic treatment of the alcohol dependence", Rev Bras Psiquiatr., 26(Suppl 1), (May 2004), S43-6.

Caumo, Andrea, et al., "Insulin sensitivity from meal tolerance tests in normal subjects: A Minimal Model Index", Journal of Clinical Endocrinology & Metabolism 85, (2000), 4396-4402.
Chan, Eric, et al., "Integrating Transcriptomics and Proteomics", G&P magazine vol. 6 No. 3, (2006), 20-26.
Chen, G., et al., "Discordant Protein and mRNA Expression in Lung Adenocarcinomas", Molecular & Cellular Proteomics 1(4), (2002), 304-313.
Cheung, V. G., et al., "Natural variation in human gene expression assessed in lymphoblastoid cells", Nature Genetics, 33(3), (Mar. 2003), 422-425.
Chorbov, V. M, et al., "Relationship of 5-HTTLPR Genotypes and Depression Risk in the Presence of Trauma in a Female Twin Sample", American Journal of Medical Genetics, Part B: Neuropsychiatric Genetics, vol. 144B, (2007), 830-832.
Clausen, Jesper O, "Insulin Sensitivity Index, Acute Insulin Response, and Glucose Effectiveness in a Population-based Sample of 380 Young Healthy Caucasians", Journal of Clinical Investigation 98, (1996), 1195-1209.
Cobb, J P, et al., "Sepsis gene expression profiling: Murine splenic compared with hepatic responses determined by using complementary DNA microarrays", Crit Care Med, 30(12), (2002), 2711-2721.
Corley, R P, et al., "Association of candidate genes with antisocial drug dependence in adolescents", Drug and Alcohol Dependence, Elsevier Scientific Publisher vol. 96, No. 1-2, (Jul. 1, 2008), 90-98.
Corrao, et al., "A meta-analysis of alcohol consumption and the risk of 15 diseases", Preventive Medicine, vol. 38, (2004), 613-619.
Cortot, A., et al., "Gastric emptying and gastrointestinal absorption of alcohol ingested with a meal", Dig Dis Sci., 31(4), (Apr. 1986), 343-8.
Dahmen, Norbert, et al., "Tyrosine hydroxylase Val-81-Met polymorphism associated with early-onset alcoholism", Psychiatric Genetics, vol. 15, (2005), 13-16.
Dalla, Man C, et al., "Measurement of selective effect of insulin on glucose disposal from labeled glucose oral test minimal model", Am J Physiol Endocrinol Metab. 289(5), (2005), E909-14.
Dalla, Man C, et al., "Minimal Model Estimation of Glucose Absorption and Insulin Sensitivity from Oral Test: Validation with a Tracer Method", Am. J. Physiol. Endocrinol. Metab. 287, (2004), E637-E643.
Dalla Man, C., et al., "The oral glucose minimal model: estimation of insulin sensitivity from a meal test", IEEE Trans Biomed Eng., 49(5), (May 2002), 419-29.
Dawes, M, et al., "Drinking histories in alcohol-use-disordered youth: preliminary findings on relationships to platelet serotonin transporter expression with genotypes of the serotonin transporter", Journal of Studies on Alcohol and Drugs vol. 70, No. 6, (Nov. 2009), 899-907.
Dawes, M. A., et al., "A prospective, open-label trial of ondansetron in adolescents with alcohol dependence", Addictive Behaviors, 30, (2005), 1077-1085.
Defronzo, RA, "Glucose clamp technique: a method for quantifying insulin secretion and resistance", Am J Physiol. 237(3), (1979), E214-23.
Dick, D, et al., "Association analyses of the serotonin transporter gene with lifetime depression and alcohol dependence in the Collaborative Study on the Genetics of Alcoholism (COGA) sample", Psychiatric Genetics, vol. 17, No. 1, (Feb. 2007), 35-38.
Ducci, F, et al., "HTR3B is associated with alcoholism with antisocial behavior and alpha EEG power—an intermediate phenotype for alcoholism and co-morbid behaviors", Alcohol, Pergamon Press London GB, vol. 43, No. 1, (Feb. 1, 2009), 73-84.
Elahi, D, "In praise of the hyperglycemic clamp: A method for assessment of beta-cell sensitivity and insulin resistance", Diabetes Care 19, (1996), 278-286.
Enard, Wolfgang, et al., "Intra- and Interspecific Variation in Primate Gene Expression Patterns", Science, vol. 296, (2002), 340-343.
Enoch, et al., "Functional genetic variants that increase synaptic serotonin and 5-HT3 receptor sensitivity predict alcohol and drug dependence", Molecular Psychiatry, vol. 16, (Sep. 14, 2010), 1139-1146.

(56) References Cited

OTHER PUBLICATIONS

Enoch, et al., "Variation in genes encoding 5-HT3 receptors influences alcoholism vulnerability in diverse populations", Alcoholism: Clinical and Experimental Research, vol. 33, (Abstract Only), (2009), 295A.

Enoch, M. A, et al., "Genetics of Alcoholism Using Intermediate Phenotypes", Alcohol Clin Exp Res., 27(2), (Feb. 2003), 169-176.

Enoch, Mary-Anne, "Pharmacogenomics of Alcohol Response and Addiction", Am J Pharmacogenomics 2003; 3 (4): 217-232, (2003), 16 pgs.

Feinn, R, et al., "Meta-analysis of the association of a functional serotonin transporter promoter polymorphism with alcohol dependence", American Journal of Medical Genetics. Part B, Neuropsychiatric Genetics, vol. 133B, No. 1, (Feb. 5, 2005), 79-84.

Flier, Jeffrey S, "Chapter 140—Syndromes of Insulin Resistance", Principles and practice of endocrinology and metabolism, editor, Kenneth L. Becker; Published Philadelphia : J.B. Lippincott Co., (1995), 1249-1259.

Fraser, A G, et al., "Inter-individual and intra-individual variability of ethanol concentration-time profiles: comparison of ethanol ingestion before or after an evening meal", Br J Clin Pharmacol. 40(4), (1995), 387-392.

Grant, S A, et al., "Blood Alcohol Concentration and Psychomotor Effects", British Journal of Anesthesia, 85(3), (2000), 401-406.

Gu, Bo, et al., "Association between a polymorphism of the HTR3A gene and therapeutic response to risperidone treatment in drug-naive Chinese schizophrenia patients", Pharmacogenetics and Genomics, vol. 88(8), (2008), 721-727.

Hartman, B. J, "Hypnotherapeutic approaches to the treatment of alcoholism", J Natl Med Assoc., 68(2), (Mar. 1976), 101-3, 147.

Hegele, Robert A, "SNP Judgments and Freedom of Association", Arterioscler Thromb Vase Biology, vol. 22, (2002), 1058-1061.

Herman, Aryeh I, et al., "Serotonin Transporter Promoter Polymorphism and Differences in Alcohol Consumption Behavior in a College Student Population", Alcohol and Alcoholism, vol. 38, No. 5, (2003), 446-449.

Hirschhorn, J. N, et al., "A Comprehensive review of genetic association studies", Genetics in Medicine, 4 (2), (Mar. 2002), 45-61.

Hoshikawa, Y., et al., "Hypoxia induces different genes in the lungs of rats compared with mice", Physiol Genomics, 12(3), (2003), 209-219.

Ioannidis, John P.A, et al., "Replication validity of genetic association studies", Nature Genetics, vol. 29; 306-309, (Nov. 2001), 4 pgs.

Ji, Xiaofei, et al., "An Association between serotonin receptor 3B Gene (HTR3B) and Treatment-Resistant Schizophrenia (TRS) in a Japanese Population", Nagoya J Med Sci, vol. 70, (2008), 11-17.

Johnson, et al., "Oral Topiramate for Treatment of Alcohol Dependence: A Randomised Controlled Trial", The Lancet, vol. 361, (May 2003), 1677-1685.

Johnson, B A, et al., "Understanding and treating alcohol dependence", Alcohol Clin Exp Res., 30(3), (Mar. 2006), 567-84.

Johnson, B., "An Overview of the Development of Medications Including Novel Anticonvulsants for the Treatment of Alcohol Dependence", Expert Opinion, Pharmacother: 5(9), (2004), 1943-1955.

Johnson, B. A., et al., "Can serotonin transporter genotype predict serotonergic function, chronicity, and severity of drinking?", Progress In Neuro-Psychopharmacology & Biological Psychiatry, 32, (2008), 209-216.

Johnson, B. A, "Effects of GR 68755 on d-amphetamine-induced changes in mood, cognitive performance, appetite, food preference, and caloric and macronutrient intake in humans", Behav. Pharmacol., 7(3), (May 1996), 216-227.

Johnson, B. A, et al., "Pharmacogenetic approach at the serotonin transporter gene as a method of reducing the severity of alcohol drinking", Am J Psychiatry, 168(3), (Mar. 2011), 265-75.

Johnson, Bankole A, et al., "Age of onset as a discriminator between alcoholic subtypes in a treatment-seeking outpatient population", Am J Addict., 9(1), (Winter, 2000), 17-27.

Johnson, Bankole A., et al., "Combining Ondansetron and Naltrexone Effectively Treats Biologically Predisposed Alcoholics: From Hypotheses to Preliminary Clinical Evidence", Alcoholism: Clinical and Experimental Research, 24(5), (May 2000), 737-742.

Johnson, Bankole A, et al., "Determination of Genotype Combinations That Can Predict the Outcome of the Treatment of Alcohol Dependence using the 5-HT3 Antagonist Ondansetron", Am J Psychiatry, 170(9), (2013), 20 pgs.

Johnson, Bankole A, et al., "Development of novel pharmacotherapies for the treatment of alcohol dependence: focus on antiepileptics", Alcohol Clin Exp Res., 28(2), (Feb. 2004), 295-301.

Johnson, Bankole A, et al., "Improvement of physical health and quality of life of alcohol-dependent individuals with topiramate treatment: US multisite randomized controlled trial", Arch Intern Med., 168(11), (Jun. 9, 2008), 1188-99.

Johnson, Bankole A, et al., "Neuropharmacological treatments for alcoholism: scientific basis and clinical findings", Psychopharmacology (Berl), 149(4), (May 2000), 327-44.

Johnson, Bankole A., et al., "Ondansetron for Reduction of Drinking Among Biologically Predisposed Alcoholic Patients: A Randomized Controlled Trial", JAMA, vol. 284, No. 8, (Aug. 2000), 963-971.

Johnson, Bankole, "Progress in the Development of Topiramate for Treating Alcohol Dependence: From a Hypothesis to a Proof-of-Concept Study", Alcoholism: Clinical and Experimental Research vol. 28, Issue 8, (Aug. 2004), 1137-1144.

Johnson, Bankole A, "Serotonergic agents and alcoholism treatment: rebirth of the subtype concept—an hypothesis", Alcohol Clin Exp Res., 24(10), (Oct. 2000), 1597-601.

Johnson, Bankole A, et al., "Topiramate for Treating Alcohol Dependence: A Randomized Controlled Trial", JAMA, 298(14), (Oct. 10, 2007), 1641-51.

Kaysen, D., et al., "Domestic Violence and Alcohol Use: Trauma-related Symptoms and Motives for Drinking", Addict Behav., vol. 32(6), (2007), 1272-1283.

Kenna, G, "A within-group design of nontreatment seeking 5-HT-TLPR genotyped alcohol-dependent subjects receiving ondansetron and sertraline", Alcoholism, Clinical and Experimental Research vol. 33, No. 2, (Feb. 2009), 315-323.

Kenna, G. A., et al., "Pharmacotherapy, pharmacogenomics, and the future of alcohol dependence treatment, part 1", Am. J. Health-Syst. Pharm., 61, (Nov. 1, 2004), 2272- 2279.

Kenna, G. A., et al., "Pharmacotherapy, pharmacogenomics, and the future of alcohol dependence treatment, part 2", Am. J. Health-Syst. Pharm., 61, (Nov. 15, 2004), 2380-2390.

Kenna, George A., "Pharmacotherapy of Alcohol Dependence: Targeting a Complex Disorder", Drug Discovery Today: Therapeutic Strategies, vol. 2, No. 1, XP004991436., (2005), 71-78.

Kenna, George A, et al., "Pharmacotherapy of Dual Substance Abuse and Dependence", CNS drugs, 21(3), (2007), 213-237.

Kjems, L L, et al., "Quantification of beta-cell function during IVGTT in Type II and non-diabetic subjects: assessment of insulin secretion by mathematical methods", Diabetologia 44, (2001), 1339-1348.

Konishi, T., et al., "ADH1B*1, ADH1C*2, DRD2 (-141C Ins), and 5-HTTLPR are associated with alcoholism in Mexican American men living in Los Angeles", Alcohol Clin Exp Res., vol. 28(8), (2004), 1145-52.

Kranzler, H. R, et al., "Effects of Ondansetron in Early- Versus Late-onset Alcoholics: A Prospective, Open-Label Study", Alcoholism: Clinical and Experimental Research, 27(7), (Jul. 2003), 1150-1155.

Liang, De-Yong, et al., "5-Hydroxytryptamine Type 3 Receptor Modulates Opioidinduced Hyperalgesia and Tolerance in Mice", Anesthesiology; 114(5): 1180-1189. doi:10.1097/ALN.0b013e31820efb19., (May 2011), 21 pgs.

Liefmann, R, "Endocrine Imbalance in Rheumatoid Arthritis and Rheumatoid Spondylitis: Hyperglycemia Unresponsiveness, Insulin Resistance, Increased Gluconeogenesis and Mesenchymal Tissue Degeneration", Acta Medica Scandinavica, 136(3), (1950), 226-232.

(56) References Cited

OTHER PUBLICATIONS

Liu, Y., et al., "Association of habitual smoking and drinking with single nucleotide polymorphism (SNP) in 40 candidate genes: data from random population-based Japanese samples", J Hum Genet., 50(2), (2005), 62-68.

Lucentini, J., "Gene Association Studies Typically Wrong", The Scientist, vol. 18 No. 24, (Dec. 20, 2004), 20 pgs.

Mahesh, et al., "Antidepressant-like activity of (4-phenylpiperazin-1-yl) (quinoxalin-2-yl) methanone (4a), a novel 5-HT3 receptor antagonist: An investigation in behavior-based rodent models of depression", Indian Journal Pharmacology, vol. 44, (2012), 560.

Mannelli, P, et al., "Polymorphism in the serotonin transporter gene and response to treatment in African American cocaine and alcohol-abusing individuals", Addict Biol., 10(3), (Sep. 2005), 261-268.

Mannelli, P., et al., "Polymorphism in the serotonin transporter gene and moderators of prolactin response to meta-chlorophenylpiperazine in African-American cocaine abusers and controls", Psychiatry Research, 144, (2006), 99-108.

Martin, J., et al., "Mapping regulatory variant for the serotonin transporter gene based on allelic expression imbalance", Molecular Psychiatry, vol. 12, (2007), 421-422.

Matsumoto, H., et al., "Pharmacokinetics of ethanol: a review of the methodology", Addiction Biology, 7(1), (2002), 5-14.

Moak, D. H, "Assessing the efficacy of medical treatments for alcohol use disorders", Expert Opin Pharmacother., 5(10), (Oct. 2004), 2075-89.

Moner, S. E., "Acupuncture and Addiction Treatment", Journal of Addictive Diseases, 15(3), (1996), 79-100.

Mumenthaler, M S, et al., "Ethanol pharmacokinetics in white women: nonlinear model fitting versus zero-order elimination analyses", Alcohol Clin Exp Res., 24(9), (Sep. 2000), 1353-62.

Ni, T C, et al., "Reassessment of glucose effectiveness and insulin sensitivity from minimal model analysis: a theoretical evaluation of the single-compartment glucose distribution assumption", Diabetes, 46(11), (1997), 1813-21.

Ni, Xingqun, et al., "Serotonin genes and gene-gene interactions in borderline personality disorder in a matched case-control study", Progress in Neuro-Psychopharmacology and Biological Psychiatry, vol. 33, (Nov. 12, 2009), 128-133.

Norberg, A, et al., "Role of variability in explaining ethanol pharmacokinetics: research and forensic applications", Clin. Pharmacokinet. 42(1), (2003), 1-31.

Norberg, A., et al., "Within- and between-subject variations in pharmacokinetic parameters of ethanol by analysis of breath, venous blood and urine", Br J Clin Pharmacol., 49(5), (2000), 399-408.

Oneta, C M, "First pass metabolism of ethanol is strikingly influenced by the speed of gastric emptying", Gut, 43(5), (1998), 612-619.

Pettinati, Helen, et al., "Recent advances in the treatment of alcoholism", Clinical Neuroscience Research, 5(2-4), (Nov. 2005), 151-159.

Philibert, "Transcriptional Profiling of Subjects From the Iowa Adoption Studies", Am J Med Genet Part B 144B, (Jul. 2007), 683-690.

Philibert, R A, et al., "The relationship of 5HTT (SLC6A4) methylation and genotype on mRNA expression and liability to major depression and alcohol dependence in subjects from the Iowa Adoption Studies", American Journal of Medical Genetics. Part B, Neuropsychiatric Genetics, vol. 147B, No. 5, (Jul. 5, 2008), 543-549.

Reaven, G M, "Pathophysiology of insulin resistance in human disease", Physiol Rev., 75(3), (1995), 473-86.

Reist, C., et al., "Serotonin Transporter Promoter Polymorphism Is Associated With Attenuated Prolactin Response to Fenfluramine", American Journal of Medicla Genetics (Neuropsychiatric Genetics), 105, (2001), 363-368.

Samochowiec, J., et al., "Family-based and case-control study of DRD2, DAT, 5HTT, COMT genes polymorphisms in alcohol dependence", Neurosci Lett., 410(1), (Dec. 13, 2006), 1-5.

Sander, Thomas, et al., "Serotonin Transporter Gene Variants in Alcohol-Dependent Subjects with Dissocial Disorder", Biol. Psychiatry, 43, (1998), 908-912.

Sellers, E. M, et al., "Clinical efficacy of the 5-HT3 antagonist ondansetron in alcohol abuse and dependence", Alcohol Clin Exp Res., 18(4), (Aug. 1994), 879-85.

Seneviratne, C, et al., "Characterization of a functional polymorphism in the 3' UTR of SLC6A4 and its association with drinking intensity", vol. 33, No. 2, (Feb. 1, 2009), 332-339.

Seneviratne, C, et al., "Characterization of a functional polymorphism in the 3' UTR of SLC6A4 and its association with drinking intensity", Alcoholism, Clinical and Experimental Research, vol. 33, No. 2, (Feb. 2009), 332-339.

Silverstone, P H, et al., "Ondansetron, a 5-HT3 receptor antagonist, partially attenuates the effects of amphetamine: a pilot study in healthy volunteers", Int Clin Psychopharmacol. 7(1), (1992), 37-43.

Sookoian, S, et al., "Contribution of the functional 5-HTTLPR variant of the SLC6A4 gene to obesity risk in male adults", Obesity, vol. 16, No. 2, (Feb. 2008), 488-491.

Souza, et al., "Are serotonin 3A and 3B receptor genes associated with suicidal behavior in schizophrenia subjects?", Neuroscience Letters, vol. 489, (Dec. 22, 2010), 137-141.

Souza, RP, et al., "Influence of serotonin 3A and 3B receptor genes on clozapine treatment response in schizophrenia", Pharmacognetics and Genomics, vol. 20(4), (Apr. 2010), 274-276.

Steil, Garry M, et al., "Evaluation of insulin sensitivity and beta-cell function indexes obtained from minimal model analysis of a meal tolerance test", Diabetes, 53(5), (2004), 1201-7.

Stoltenberg, S. F., et al., "Serotonergic Agents and Alcoholism Treatment: A Simulation", Alcoholism: Clinical and Experimental Research, 27(12), (Dec. 2003), 1853-1859.

Swift, R., "Topiramate for the Treatment of Alcohol Dependence: Initiating Abstinence", The Lancet, vol. 361, (May 2003), 1666-1667.

Szilagyi, A., et al., "Combined effect of promoter polymorphisms in the dopamine D4 receptor and the serotonin transporter genes in heroin dependence", Neuropsychopharmacol Hung., 7(1), (2005), 28-33.

Toffolo, G, et al., "Beta-cell function during insulin-modified intravenous glucose tolerance test successfully assessed by the C-peptide minimal model", Metabolism, 48(9), (1999), 1162-1166.

Toffolo, G, et al., "Estimation of beta-cell sensitivity from intravenous glucose tolerance test C-peptide data. Knowledge of the kinetics avoids errors in modeling the secretion", Diabetes, 44(7), (1995), 845-854.

Toffolo, Gianna, et al., "Quantitative indexes of ß-cell function during graded up&down glucose infusion from C-peptide minimal models", Am J Physiol Endocrinol Metab., 280(1), (2001), E2-E10.

Umulis, D M, et al., "A physiologically based model for ethanol and acetaldehyde metabolism in human beings", Alcohol, 35(1), (2005), 3-12.

Walstab, Jutta, et al., "5-HT3 receptors: Role in disease and target of drugs", Pharmacology & Therapeutics 128 (2010) 146-169, (Jul. 16, 2010), 146-169.

Ward, R J, et al., "Women and alcohol susceptibility: could differences in alcohol metabolism predispose women to alcohol-related diseases?", Arch Womens Ment Health., 6(4), (2003), 231-8.

Welch, S, et al., "Minimal model analysis of intravenous glucose tolerance test-derived insulin sensitivity in diabetic subjects", J Clin Endocrinol Metab., 71(6), (1990), 1508-1518.

Whitehead, Douglas, et al., "Variation in tissue-specific gene expression among natural populations", Genome Biology vol. 6 Issue 2 Article R13, (2005), R13.1-R13.14.

Williams, S., "Medications for Treating Alcohol Dependence", American Family Physician, vol. 72, No. 9, (Nov. 2005), 1775-1780.

Willms, B, et al., "Gastric emptying, glucose responses, and insulin secretion after a liquid test meal: effects of exogenous glucagon-like peptide-1 (GLP-1)-(7-36) amide in type 2 (noninsulin-dependent) diabetic patients", J Clin Endocrinol Metab., 81(1), (1996), 327-32.

Wise, Roy A, et al., "A Psychomotor stimulant theory of addiction", Psychological Review 94, (1987), 469-492.

(56) References Cited

OTHER PUBLICATIONS

Wolff, Manfred E, "Burgers Medicinal Chemistry", 5th ed. Part 1. John Wiley & Sons, (1995), 975-977.

Xu, Li-Ping, "Analysis on the relationship between the polymorphism of serotonin transporter promoter gene and conduct disorder", (w/ English Abstract), Chinese Journal of Behavioral Medical Science, vol. 15, No. 7, (Jul. 2006), 588-590.

"U.S. Appl. No. 17/301,660, Response filed Feb. 9, 2023 to Non Final Office Action mailed Nov. 9, 2022", 7 pgs.

"U.S. Appl. No. 17/301,660, Non Final Office Action mailed Mar. 9, 2023", 18 pgs.

"U.S. Appl. No. 17/301,660, Response filed Jun. 6, 2023 to Non Final Office Action mailed Mar. 9, 2023", 7 pgs.

"U.S. Appl. No. 18/188,755, Restriction Requirement mailed Jul. 5, 2023", 5 pgs.

"U.S. Appl. No. 18/188,755, Response filed Sep. 5, 2023 to Restriction Requirement mailed Jul. 5, 2023", 7 pgs.

"U.S. Appl. No. 17/301,660, Notice of Allowance mailed Sep. 22, 2023", 9 pgs.

"U.S. Appl. No. 18/188,755, Non Final Office Action mailed Oct. 4, 2023", 6 pgs.

"U.S. Appl. No. 17/301,660, Notice of Allowability mailed Oct. 5, 2023", 2 pgs.

"Canadian Application Serial No. 2,848,211, Examiners Rule 86(2) Requisition mailed Oct. 3, 2023", 3 pgs.

"U.S. Appl. No. 17/301,660, PTO Response to Rule 312 Communication mailed Dec. 22, 2023", 2 pgs.

"U.S. Appl. No. 18/188,755, Response filed Jan. 3, 2024 to Non Final Office Action mailed Oct. 4, 2023", 7 pgs.

"U.S. Appl. No. 18/188,755, Notice of Allowance mailed Jan. 18, 2024", 7 pgs.

"Canadian Application Serial No. 2,848,211, Response filed Feb. 1, 2024 to Examiners Rule 86(2) Requisition mailed Oct. 3, 2023", 6 pgs.

"U.S. Appl. No. 17/659,641, Non Final Office Action mailed May 7, 2024", 6 pgs.

"U.S. Appl. No. 18/394,729, Non Final Office Action mailed Aug. 7, 2024", 15 pgs.

"U.S. Appl. No. 17/659,641, Response filed Aug. 7, 2024 to Non Final Office Action mailed May 7, 2024", 7 pgs.

U.S. Appl. No. 18/394,729, filed Dec. 22, 2023, Serotonin Transporter Gene and Treatment of Opioid-Related Disorders.

U.S. Appl. No. 18/188,755 U.S. Pat. No. 11,957,664, filed Mar. 23, 2023, Molecular Genetic Approach to Treatment and Diagnosis of Alcohol And Drug Dependence.

U.S. Appl. No. 18/622,489, filed Mar. 29, 2024, Molecular Genetic Approach to Treatment and Diagnosis of Alcohol And Drug Dependence.

\* cited by examiner

MEAN DIFFERENCE BETWEEN TREATMENT AND PLACEBO AND ITS 95% CONFIDENCE INTERVALS

LL/T+ CARRIES VS. OTHERS IN THE LINEAR MIXED
EFFECT MODEL: PERCENT HEAVY DRINKING DAYS

| EFFECT | ESTIMATED MEAN DIFFERENCE | LOWER 95% C.I. | UPPER 95% C.I. | P-VALUE | EFFECT SIZE |
|---|---|---|---|---|---|
| AMONG LL/T+ CARRIERS: OND VS. PLACEBO | -13.15 | -22.02 | -0.28 | 0.04 | 0.43 |
| AMONG OND: LL/T+ CARRIERS VS. OTHERS | -9.11 | -18.25 | 0.03 | 0.05 | 0.35 |

Fig. 11A

MEAN DIFFERENCE BETWEEN TREATMENT AND PLACEBO AND ITS 95% CONFIDENCE INTERVALS

LL/T+ CARRIERS VS. OTHERS IN LINEAR MIXED EFFECTS MODEL: DRINKS/DRINKING DAY

| EFFECT | ESTIMATED MEAN DIFFERENCE | LOWER 95% C.I. | UPPER 95% C.I. | P-VALUE | EFFECT SIZE |
|---|---|---|---|---|---|
| AMONG LL/T+ CARRIERS: OND VS. PLACEBO | -1.65 | -2.88 | -0.42 | 0.009 | 0.57 |
| AMONG OND: LL/T+ CARRIERS VS. OTHERS | -1.68 | -2.71 | -0.64 | 0.002 | 0.56 |

Fig. 11B

LL/T+ CARRIERS VS. OTHERS IN LINEAR MIXED EFFECTS MODEL: PERCENT DAYS ABSTINENT

MEAN DIFFERENCE BETWEEN TREATMENT AND PLACEBO AND ITS 95% CONFIDENCE INTERVALS

| EFFECT | ESTIMATED MEAN DIFFERENCE | LOWER 95% C.I. | UPPER 95% C.I. | P-VALUE | EFFECT SIZE |
|---|---|---|---|---|---|
| OND VS. PLACEBO AMONG LL/T+ CARRIERS: | 6.22 | 0.11 | 12.33 | 0.046 | 0.21 |
| OND VS. PLACEBO AMONG OND: | 12.53 | 2.28 | 22.78 | 0.017 | 0.50 |
| LL/T+ CARRIERS VS. OTHERS | 10.33 | 1.72 | 18.94 | 0.019 | 0.40 |

Fig. 11C

PERCENTAGE OF PATIENTS WITH LESS THAN 3(1/MONTH) HEAVY DRINKING DAYS IN ALL 12 WEEKS BY LOGISTIC REGRESSION

TABLE 1: ANOVA

| VARIABLE | CHI-SQUARE | P-VALUE |
|---|---|---|
| COMBINED 4-CELL | 12.04 | 0.007 |
| AGE | 16.32 | <0.0001 |
| GENDER | 0.31 | 0.579 |
| RACE | 4.41 | 0.036 |
| CENTER | 14.38 | 0.0001 |
| BASELINE | 15.40 | <0.0001 |
| OVERALL | 37.14 | <0.0001 |

COMBINED 4-CELL: OND + LL/T+ CARRIERS, OND + OTHERS, PLACEBO + LL/T+ CARRIERS, AND PLACEBO +

TABLE 2: P-VALUES

| EFFECT | P-VALUE |
|---|---|
| LL/T+ CARRIERS GENOTYPES: OND VS. PLACEBO | 0.05 |
| AMONG OND: LL/T+ CARRIERS VS. OTHERS | <0.01 |
| OND + LL/T+ CARRIERS VS. PLACEBO +OTHERS | <0.01 |

Fig. 12

SEQUENCE LISTING

```
Sequence total quantity: 2
SEQ ID NO: 1              moltype = DNA   length = 23
FEATURE                   Location/Qualifiers
source                    1..23
                          mol_type = other DNA
                          organism = synthetic construct
SEQUENCE: 1
tcctccgctt tggcgcctct tcc                                              23

SEQ ID NO: 2              moltype = DNA   length = 23
FEATURE                   Location/Qualifiers
source                    1..23
                          mol_type = other DNA
                          organism = synthetic construct
SEQUENCE: 2
tgggggttgc aggggagatc ctg                                              23
```

MOLECULAR GENETIC APPROACH TO TREATMENT AND DIAGNOSIS OF ALCOHOL AND DRUG DEPENDENCE

CROSS REFERENCE TO RELATED APPLICATIONS

This application is a continuation of U.S. patent application Ser. No. 17/659,641, filed on Apr. 18, 2022, which is a continuation of U.S. patent application Ser. No. 16/784,051, filed on Feb. 6, 2020, which is a continuation of U.S. patent application Ser. No. 15/397,076, filed on Jan. 3, 2017, which is a continuation of U.S. patent application Ser. No. 14/266,313, filed on Apr. 30, 2014, which is a divisional of U.S. patent application Ser. No. 13/589,603, filed on Aug. 20, 2012, which is a continuation under 35 U.S.C. § 111(a) of and claims the benefit of priority to International Patent Application Serial No. PCT/US2011/042823, filed on Jul. 1, 2011, and published on Jan. 5, 2012 as WO 2012/003462 and republished on Mar. 22, 2012, which is entitled to priority pursuant to 35 U.S.C. § 119(e) to U.S. provisional patent application nos. 61/361,203, filed on Jul. 2, 2010; 61/429,416, filed on Jan. 3, 2011; and 61/488,328, filed on May 20, 2011. The entire disclosures of the afore-mentioned patent applications are incorporated herein by reference.

STATEMENT REGARDING FEDERALLY SPONSORED RESEARCH OR DEVELOPMENT

This invention was made with government support under Grant Nos. AA001016, AA012964, AA010522, and AA032903 awarded by the National Institutes of Health. The government has certain rights in the invention.

INCORPORATION BY REFERENCE BF SEQUENCE LISTING

A Sequence Listing is provided herewith as an xml file, "2306985.xml" created on Feb. 3, 2023 and having a size of 2,912 bytes. The content of the xml file is incorporated by reference herein in its entirety.

BACKGROUND

Alcohol abuse and dependence are widespread and it is estimated that 14 million American adults abused alcohol or were dependent on it in 1992 and that approximately 10% of Americans will be affected by alcohol dependence sometime during their lives. Alcohol dependence, characterized by the preoccupation with alcohol use, tolerance, and withdrawal, is a chronic disorder with genetic, psychosocial, and environmental factors influencing its development and manifestations. Studies have demonstrated the significance of opioids (i.e., beta-endorphin), dopamine (DA), serotonin (5-HT), γ-amino-butyric acid (GABA) and glutamate for the development and maintenance of alcohol dependence.

Various medications and behavioral therapy have been used to treat alcohol dependence. The neuronal targets of alcohol include many neurotransmitter systems and the molecules participating in or regulating the systems, including GABA, glutamate, DA, opioids, and serotonin (for a review see Johnson, 2004, Expert Opin. Pharmacother., 5:9:1943-1955).

Despite the number of studies performed in this area, few drugs for alcohol dependence are approved in the U.S. The approved drugs are disulfiram, naltrexone, Vivitrex®/Vivitrol® (a long-acting depot formulation of naltrexone), and acamprosate. Disulfiram is an irreversible inhibitor of aldehyde dehydrogenase leading to increased levels of acetaldehyde, a toxic intermediate in alcohol metabolism. Patients who take disulfiram and drink alcohol experience an increased dilation of arterial and capillary tone producing hypotension, nausea, vomiting, flushing, headache and possibly in some, worse symptoms. Therefore, the concept behind the use of disulfiram is that the alcohol-dependent individual associates drinking with unpleasant adverse events and, as a result, avoids further alcohol consumption. Nevertheless, recent research shows that disulfiram has limited utility because compliance is low unless it is administered by a partner or spouse.

Serotonin (5-HT) dysfunction probably contributes to the development of alcoholism. Serotonin's receptors contribute to alcohol use in animals, as alcohol increases basal levels of 5-HT affecting receptors. Of the seven distinct families of 5-HT receptors, three are known to contribute to alcohol dependence: $5\text{-}HT_{1A}$ receptors might be associated with alcohol consumption and the development of tolerance; $5\text{-}HT_2$ receptors with reward; and $5\text{-}HT_3$ receptors with the development of reinforcement. Based on such evidence, several serotonergic drugs have been examined, but with inconsistent results. Presently only sertraline and ondansetron (a serotonin-3 ($5\text{-}HT_3$) antagonist) appear to show any promise with certain subtypes of alcoholic patients and fluoxetine with depressed alcoholics (see Kenna, 2005, Drug Discovery Today: Therapeutic Strategies, 2:1:71-78 and Johnson, 2000, Alcohol. Clin. Exp. Res., 24:1597-1601).

The $5\text{-}HT_3$ receptor is involved in the expression of alcohol's rewarding effects. Behavioral pharmacological studies show that many of alcohol's rewarding effects are mediated by interactions between DA and 5-HT receptors in the midbrain and cortex. 5-HT receptors are densely distributed in the terminals of mesocorticolimbic DA containing neurons, where they regulate DA release in these brain regions. These DA pathways, particularly those in the NAc, are involved in mediating the rewarding effects of abused substances including alcohol. Demonstration that $5\text{-}HT_3$ receptor blockade reduces DA activity, and therefore the rewarding effects of abused drugs (including alcohol), comes from at least three different animal paradigms. $5\text{-}HT_3$ receptor antagonists: 1) attenuate hyperlocomotion in the rat induced by DA or ethanol injection into the nucleus accumbens; 2) inhibit DiMe-C7 (a neurokinin)-induced hyperlocomotion, which is also attenuated by the DA antagonist, fluphenazine; and 3) decrease alcohol consumption in several animal models and across different species.

Animal studies demonstrated that the $5\text{-}HT_3$ receptor facilitates some of the biochemical and behavioral effects of alcohol through midbrain DA release. $5\text{-}HT_3$ antagonists are consistently shown to suppress alcohol preference in animal studies, with recent evidence suggesting the $5\text{-}HT_{3A}$ receptor subunit requisite for $5\text{-}HT_3$ antagonist-induced reductions in alcohol consumption.

Ondansetron, a $5\text{-}HT_3$ receptor antagonist, has functionally opposite effects to SSRIs and blocks serotonin agonism at the $5\text{-}HT_3$ receptor. According to studies, ondansetron can be effective for early-onset alcoholics (EOA) but not late-onset alcoholics (*LOA*), where age of onset of alcoholism (younger versus older than 25 years old) is the basis for subtyping alcoholics (Johnson, 2000, Alcohol. Clin. Exp. Res., 24:1597-1601). In a placebo-controlled trial, 271 participants were stratified into EOA and LOA subtypes by 1, 4, and 16 μg/kg twice-daily doses of ondansetron compared with placebo (Johnson, 2000, J. Am. Med. Assoc., 284:963-971). Patients with EOA who received ondansetron showed significant reductions in drinking (particularly those receiving 4 μg/kg twice daily) compared with LOA across all groups. In another study, it was shown that ondansetron treatment is more likely to be associated with improved drinking outcomes among EOA compared with LOA (Kranzler et al., (2003, Alcohol. Clin. Exp. Res., 27:1150-1155). Ondansetron continues to be examined for individuals with early-onset alcoholism.

The reasons for these differential effects are unknown; however, one hypothesis suggests that alcoholics with a biological predisposition have a dysregulation of serotonergic function primarily associated with serotonin transporter (SERT) function (Johnson, 2000, Alcohol. Clin. Exp. Res. 24:1597-1601). The polymorphic variation of the SERT (the 5'-HTTLPR) is hypothesized to be involved with the effectiveness of ondansetron and sertraline in EOA and LOA alcohol-dependent individuals, respectively. Given that epidemiologic studies demonstrate that alcohol dependence has an approximately 50-60% heritability, the prospect for positive outcomes to drug therapy at least partly dependent on genetic predisposition in some alcoholics is strong. Recent studies have, therefore, attempted to delineate the genetic components associated with alcohol dependence. These findings highlight the role that 5-HT plays in alcohol consumption, although drug trials using serotonergics have had difficulty delineating responders from non-responders.

Vulnerability to alcohol dependence is heritable, with a rate ranging from 0.52 to 0.64 (Kendler, 2001). Despite this high heritability rate, only one marker allele (alcohol-metabolizing aldehyde dehydrogenase genes) has been identified consistently to be associated with alcoholism (Kranzler et al, 2002). Of the various neurotransmitter systems through which alcohol mediates its effects, the serotonergic system has been shown to play a role in alcohol preference and consumption (Johnson, 2004). Synaptic serotonergic neurotransmission is terminated when serotonin (5-HT) is transported back into pre-synaptic neurons by 5-HT transporters (5-HTTs) (Talvenheimo and Rudnick, 1980). Therefore, a major part of the functional capacity of the serotonergic system is regulated by the 5-HTT. Heavy episodic drinking is associated with numerous psychiatric and general medical conditions causing a major public health burden (Cargiulo, 2007). Several studies have reported a dose-response relationship between the extent of heavy drinking and the risk of alcohol related morbidity and mortality among heavy drinkers (Makela and Mustonen, 2007; Gastfriend et al., 2007). Consequently, reduction of heavy drinking is used as an indicator of treatment response in clinical trials aimed at treating alcohol dependence.

There is a long felt need in the art for compositions and methods useful for diagnosing, treating, and monitoring alcohol disorders and susceptibility to alcohol disorders.

SUMMARY OF THE INVENTION

The present invention relates to molecular genetics techniques to predict which alcohol or drug dependent subjects are amenable to specific treatments and to predict those subjects for which such treatment might produce an adverse event.

The present invention also relates to methods and assays useful for determining whether a subject has a predisposition to developing an addictive disease or disorder, determining whether a subject will be responsive to particular treatments, and compositions and methods useful for treating a subject in need of treatment.

The present invention also relates to compositions and methods useful for treating subjects having an addictive disease or disorder (or who are predisposed thereto) based on identification of genetic markers indicative of a subject being predisposed to such disease or disorder or being predisposed to responding to treatment thereof.

The present invention also relates to molecular genetics techniques and/or other ways to subtype groups by biological or psychological measures or variables to determine which subjects will respond best to treatment for an addictive disease or disorder.

These and other aspects that will become apparent are based on the discovery that molecular genetics techniques can be used to predict which alcohol or drug dependent subjects are amenable to specific treatments and to predict those subjects for which such treatment might produce an adverse event. Various aspects of the invention are described in further detail below.

BRIEF DESCRIPTION OF THE DRAWINGS

FIGS. 11A-11C provide data demonstrating that LL/t+ carriers show an effect on PHDD, DDD and PDA and are responsive to ondansetron treatment.

FIG. 12 depicts data regarding patients with less than 3 (1/month) heavy drinking days ("safe drinking") during 12 weeks.

DETAILED DESCRIPTION

Abbreviations, Generic Names, and Acronyms

Figure 1:
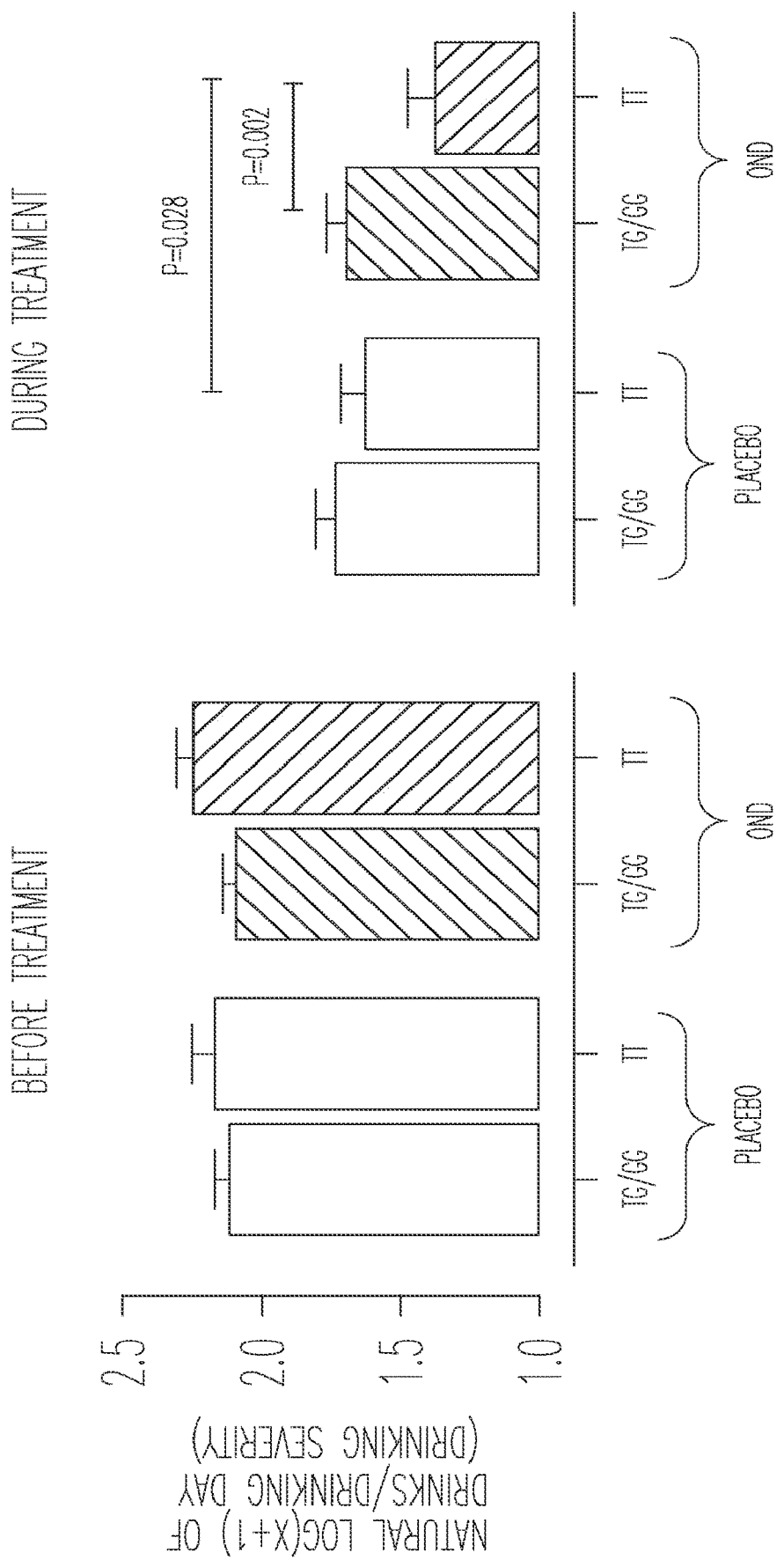
FIG. 1 provides data showing Log Drinks/Drinking Day in rs1042173 SNPs (i.e., TT vs TG/GG) among 278 alcoholics who received either ondansetron or placebo. Footnote: The mean numbers of Drinks/drinking day values (DDD) represented by "Natural log (X+1)" on the Y axis are as follows: 1=1.718; 1.5=3.482; 2=6.389; 2.5=11.182: X=Number of Drinks/drinking day. Mean DDD in ondansetron (OND) recipients are represented in closed bars, and mean DDD in placebo recipients are represented in open bars; blue and black bars represent TG/GG and TT genotypes respectively. Numbers of subjects in each rs1042173 genotypic group are as follows: TG/GGplacebo-92, TTplacebo-47, TG/GG ond-94 and TTond-45.

5-HT—serotonin
5-HT$_3$—a subtype of serotonin receptor, the serotonin-3 receptor
5-HTOL—5-hydroxytryptophol
5-HTT—serotonin transporter (also referred to as SERT, 5HTT, HTT, and OCD1)
5-HTTLPR—serotonin transporter-linked polymorphic region
ADE—alcohol deprivation effect
ADI—adolescence diagnostic interview
ASPD—antisocial personality disorder
AUD—alcohol use disorder
BBCET—Brief Behavioral Compliance Enhancement Treatment
BED—binge eating disorder
b.i.d.—twice a day
B$_{max}$—maximum specific paroxetine binding density
BRENDA—Biopsychosocial, Report, Empathy, Needs, Direct advice, and Assessment
CBI—combined behavioral intervention
CBT—Cognitive Behavioral Coping Skills Therapy, also referred to as cognitive behavioral therapy
CDT—carbohydrate-deficient transferrin
ChIPS—children's interview for psychiatric syndrome
CMDA—cortico-mesolimbic dopamine
DA—dopamine
DDD—drinks/drinking day
DSM—Diagnostic and Statistical Manual of Mental Disorders
EOA—early-onset alcoholic(s)
G2651T—a site within a putative polyadenylation signal for a commonly used 3' polyadenylation site of the SLC6A4 gene; also has reference identification number rs1042173 at the GenBank website of the National Center for Biotechnology Information
GABA—γ-amino-butyric acid (also referred to as γ-amino butyric acid and γ-aminobutyric acid)
GGT—γ-glutamyl transferase
ICD—impulse control disorder
IP—intraperitoneal
K$_d$—affinity constant
K$_m$—equilibrium constant
L—long
LOA—late-onset alcoholic(s)
MET—Motivational Enhancement Therapy
miRNA—micro RNA
MINI—Medical Management
NAc—nucleus accumbens
Naltrexone—a μ opioid receptor antagonist
ncRNA—non-coding RNA
NMDA—N-methyl-D-aspartate
NOS—not otherwise specified
Ondansetron (Zofran®)—a serotonin receptor antagonist
P—alcohol-preferring rats
S—short
SERT—serotonin transporter (also referred to as 5-HTT)
SLC6A4—human 5-HT transporter gene.
SNP—single nucleotide polymorphism
SSRI—selective serotonin re-uptake inhibitor
Topiramate (Topamax®)—an anticonvulsant
TSF—Twelve-Step Facilitation Therapy (e.g., Alcoholics Anonymous)
V.—maximum serotonin uptake velocity
VTA—ventral tegmental area Definitions In describing and claiming the invention, the following terminology will be used in accordance with the definitions set forth below. Unless defined otherwise, all technical and scientific terms used herein have the same meaning as commonly understood by one of ordinary skill in the art to which this invention belongs. Any methods and materials similar or equivalent to those described herein can be used in the practice or testing of the present invention. As used herein, each of the following terms has the meaning associated with it in this section. Specific values listed below for radicals, substituents, and ranges are for illustration only; they do not exclude other defined values or other values within defined ranges for the radicals and substituents.

As used herein, the articles "a" and "an" refer to one or to more than one, i.e., to at least one, of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

One of ordinary skill in the art will appreciate that addictive disorders such as those related to alcohol or drugs, does mean that a subject is dependent unless specifically defined as such.

The term "additional therapeutically active compound," in the context of the present invention, refers to the use or administration of a compound for an additional therapeutic use other than just the particular disorder being treated. Such a compound, for example, could include one being used to treat an unrelated disease or disorder, or a disease or disorder which may not be responsive to the primary treatment for the addictive disease or disorder being treated. Disease and disorders being treated by the additional therapeutically active agent include, for example, hypertension and diabetes.

As used herein, the term "aerosol" refers to suspension in the air. In particular, aerosol refers to the particlization or atomization of a formulation of the invention and its suspension in the air.

Cells or tissue are "affected" by a disease or disorder if the cells or tissue have an altered phenotype relative to the same cells or tissue in a subject not afflicted with a disease, condition, or disorder.

As used herein, an "agonist" is a composition of matter that, when administered to a mammal, such as a human, enhances or extends a biological activity of interest. Such effect may be direct or indirect.

The term "alcohol abuser," as used herein, refers to a subject who meets DSM IV criteria for alcohol abuse (i.e., "repeated use despite recurrent adverse consequences") but is not dependent on alcohol.

As used herein, an "analog" of a chemical compound is a compound that, by way of example, resembles another in structure but is not necessarily an isomer (e.g., 5-fluorouracil is an analog of thymine).

An "antagonist" is a composition of matter that when administered to a mammal, such as a human, inhibits or impedes a biological activity attributable to the level or presence of an endogenous compound in the mammal. Such effect may be direct or indirect.

As used herein, the term "anti-alcohol agent" refers to any active drug, formulation, or method that exhibits activity to treat or prevent one or more symptom(s) of alcohol addiction, alcohol abuse, alcohol intoxication, and/or alcohol withdrawal, including drugs, formulations and methods that significantly reduce, limit, or prevent alcohol consumption in mammalian subjects.

The term "appetite suppression," as used herein, is a reduction, a decrease or, in cases of excessive food consumption, an amelioration in appetite. This suppression reduces the desire or craving for food. Appetite suppression can result in weight loss or weight control as desired.

The term "average drinking," as used herein, refers to the mean number of drinks consumed during a one week period. The term "average drinking" is used interchangeably herein with the term "average level of drinking."

A "biomarker" is a specific biochemical in the body which has a particular molecular feature that makes it useful for measuring the progress of disease or the effects of treatment, or for measuring a process of interest.

A "compound," as used herein, refers to any type of substance or agent that is commonly considered a drug, or a candidate for use as a drug, as well as combinations and mixtures of the above.

A "control" subject is a subject having the same characteristics as a test subject, such as a similar type of dependence, etc. The control subject may, for example, be examined at precisely or nearly the same time the test subject is being treated or examined. The control subject may also, for example, be examined at a time distant from the time at which the test subject is examined, and the results of the examination of the control subject may be recorded so that the recorded results may be compared with results obtained by examination of a test subject.

A "test" subject is a subject being treated.

As used herein, a "derivative" of a compound refers to a chemical compound that may be produced from another compound of similar structure in one or more steps, as in replacement of H by an alkyl, acyl, or amino group.

As used herein, the term "diagnosis" refers to detecting a risk or propensity to an addictive related disease or disorder. In any method of diagnosis exist false positives and false negatives. Any one method of diagnosis does not provide 100% accuracy.

A "disease" is a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. However, the definitions of "disease" and "disorder" as described above are not meant to supersede the definitions or common usage related to specific addictive diseases or disorders.

A disease, condition, or disorder is "alleviated" if the severity of a symptom of the disease or disorder, the frequency with which such a symptom is experienced by a patient, or both, are reduced.

As used herein, an "effective amount" means an amount sufficient to produce a selected effect, such as alleviating symptoms of a disease or disorder. In the context of administering two or more compounds, the amount of each compound, when administered in combination with another compound(s), may be different from when that compound is administered alone. The term "more effective" means that the selected effect is alleviated to a greater extent by one treatment relative to the second treatment to which it is being compared.

The term "elixir," as used herein, refers in general to a clear, sweetened, alcohol-containing, usually hydroalcoholic liquid containing flavoring substances and sometimes active medicinal agents.

The term "excessive drinker," as used herein, refers to men who drink more than 21 alcohol units per week and women who consume more than 14 alcohol units per week. One standard drink is 0.5 oz of absolute alcohol, equivalent to 10 oz of beer, 4 oz of wine, or 1 oz of 100-proof liquor. These individuals are not dependent on alcohol but may or may not meet DSM IV criteria for alcohol abuse.

As used herein, a "functional" molecule is a molecule in a form in which it exhibits a property or activity by which it is characterized. A functional enzyme, for example, is one that exhibits the characteristic catalytic activity by which the enzyme is characterized.

The term "heavy drinker," as used herein, refers to men who drink more than 14 alcohol units per week and women who consume more than 7 alcohol units per week. One standard drink is 0.5 oz of absolute alcohol, equivalent to 10 oz of beer, 4 oz of wine, or 1 oz of 100-proof liquor. These individuals are not dependent on alcohol but may or may not meet DSM IV criteria for alcohol abuse.

The term "heavy drinking", as used with respect to the alcohol-dependent population of Example 1, refers to drinking at least about 21 standard drinks/week for women and at least 30 drinks/week for men during the 90 days prior to enrollment in the study and is more fully described therein.

A "heavy drinking day," as used herein, refers to the consumption by a man or woman of more than about five or four standard drinks per drinking day, respectively.

The term "heavy drug use," as used herein, refers to the use of any drug of abuse, including, but not limited to, cocaine, methamphetamine, other stimulants, phencyclidine, other hallucinogens, marijuana, sedatives, tranquilizers, hypnotics, opiates at intervals or in quantities greater than the norm. The intervals of use include intervals such as at least once a month, at least once a week, and at least once a day. "Heavy drug use" is defined as testing "positive" for the use of that drug on at least 2 occasions in any given week with at least 2 days between testing occasions.

As used herein, the term "inhaler" refers both to devices for nasal and pulmonary administration of a drug, e.g., in solution, powder and the like. For example, the term "inhaler" is intended to encompass a propellant driven inhaler, such as is used to administer antihistamine for acute asthma attacks, and plastic spray bottles, such as are used to administer decongestants.

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

As used herein, an "instructional material" includes a publication, a recording, a diagram, or any other medium of expression which can be used to communicate the usefulness of a compound of the invention in the kit for effecting alleviation of the various diseases or disorders recited herein. Optionally, or alternately, the instructional material may describe one or more methods of alleviating the diseases or disorders in a subject. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

"Intensity of drinking" refers to the number of drinks, which can be equated with values such as drinks/day, drinks/drinking day, etc. Therefore, greater intensity of drinking means more drinks/day, or drinks/drinking day, etc.

As used herein, a "ligand" is a compound that specifically binds to a target compound or molecule. A ligand "specifically binds to" or "is specifically reactive with" a compound when the ligand functions in a binding reaction which is determinative of the presence of the compound in a sample of heterogeneous compounds.

A "receptor" is a compound or molecule that specifically binds to a ligand.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present.

The term "nasal administration" in all its grammatical forms refers to administration of at least one compound of the invention through the nasal mucous membrane to the bloodstream for systemic delivery of at least one compound of the invention. The advantages of nasal administration for delivery are that it does not require injection using a syringe and needle, it avoids necrosis that can accompany intramuscular administration of drugs, and trans-mucosal administration of a drug is highly amenable to self administration.

"Obesity" is commonly referred to as a condition of increased body weight due to excessive fat. Drugs to treat obesity are generally divided into three groups: (1) those that decrease food intake, such as drugs that interfere with monoamine receptors, such as noradrenergic receptors, serotonin receptors, dopamine receptors, and histamine receptors; (2) those that increase metabolism; and (3) those that increase thermogenesis or decrease fat absorption by inhibiting pancreatic lipase (Bray, 2000, Nutrition, 16:953-960 and Leonhardt et al., 1999, Eur. J. Nutr., 38:1-13). Obesity has been defined in terms of body mass index (BMI). BMI is calculated as weight (kg)/[height (m)]$^2$, according to the guidelines of the U.S. Centers for Disease Control and Prevention (CDC), and the World Health Organization (WHO). Physical status: The use and interpretation of anthropometry. Geneva, Switzerland: World Health Organization 1995. WHO Technical Report Series), for adults over 20 years old, BMI falls into one of these categories: below 18.5 is considered underweight, 18.5-24.9 is considered normal, 25.0-29.9 is considered overweight, and 30.0 and above is considered obese.

The term "per application" as used herein refers to administration of a drug or compound to a subject.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "physiologically acceptable" ester or salt means an ester or salt form of the active ingredient which is compatible with any other ingredients of the pharmaceutical composition, and which is not deleterious to the subject to which the composition is to be administered.

A "predisposition" to an addictive disease or disorder refers to situations in which a subject has an increased chance of abusing a substance such as alcohol or a drug or becoming addicted to alcohol or a drug or other addictive diseases or disorders.

The term "prevent," as used herein, means to stop something from happening, or taking advance measures against something possible or probable from happening. In the context of medicine, "prevention" generally refers to action taken to decrease the chance of getting a disease or condition.

The term "problem drinker," as used herein, encompasses individuals who drink excessively and who report that their alcohol consumption is causing them problems. Such problems include, for example, driving while intoxicated, problems at work caused by excessive drinking, and relationship problems caused by excessive drinking by the subject.

The term "psychosocial management program," as used herein, relates to the use of various types of counseling and management techniques used to supplement the combination pharmacotherapy treatment of addictive and alcohol-related diseases and disorders.

"Reduce"—see "inhibit".

The term "reduction in drinking", as used herein, refers to a decrease in drinking according to one or more of the measurements of drinking such as heavy drinking, number of drinks/day, number of drinks/drinking day, etc.

The term "regulate" refers to either stimulating or inhibiting a function or activity of interest.

A "sample," as used herein, refers to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest as interpreted in the context of the claim and the type of assay to be performed using that sample.

By "small interfering RNAs (siRNAs)" is meant, inter alia, an isolated dsRNA molecule comprising both a sense and an anti-sense strand. In one aspect, it is greater than 10 nucleotides in length. siRNA also refers to a single transcript that has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

By the term "specifically binds," as used herein, is meant a molecule which recognizes and binds a specific molecule, but does not substantially recognize or bind other molecules in a sample, or it means binding between two or more molecules as in part of a cellular regulatory process, where the molecules do not substantially recognize or bind other molecules in a sample.

The term "standard," as used herein, refers to something used for comparison. For example, it can be a known standard agent or compound which is administered or added and used for comparing results when adding a test compound, or it can be a standard parameter or function which is measured to obtain a control value when measuring an effect of an agent or compound on a parameter or function. Standard can also refer to an "internal standard," such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

The term "one standard drink," as used herein, is 0.5 oz of absolute alcohol, equivalent to 10 oz of beer, 4 oz of wine, or 1 oz of 100-proof liquor.

A "subject" of diagnosis or treatment is a mammal, including a human.

The term "subject comprises a predisposition to the early onset of alcoholism," as used herein, refers to a subject who has, or is characterized by, a predisposition to the early onset of alcoholism.

The term "symptom," as used herein, refers to any morbid phenomenon or departure from the normal in structure, function, or sensation, experienced by the patient and indicative of disease. In contrast, a sign is objective evidence of disease. For example, a bloody nose is a sign. It is evident to the patient, doctor, nurse and other observers.

As used herein, the term "treating" may include prophylaxis of the specific disease, disorder, or condition, or alleviation of the symptoms associated with a specific disease, disorder or condition and/or preventing or eliminating the symptoms. A "prophylactic" treatment is a treatment administered to a subject who does not exhibit signs of a disease or exhibits only early signs of the disease for the purpose of decreasing the risk of developing pathology associated with the disease. "Treating" is used interchangeably with "treatment" herein.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term "pharmaceutically-acceptable salt" refers to salts which retain the biological effectiveness and properties of the compounds of the present invention and which are not biologically or otherwise undesirable. In many cases, the compounds of the present invention are capable of forming acid and/or base salts by virtue of the presence of amino and/or carboxyl groups or groups similar thereto.

Embodiments

In an aspect, the present invention provides a method of identifying addictive disease or disorder patients with favorable prognosis for pharmacological treatment, comprising: identifying genetic patterns favorable to treatment response.

Another aspect provides a method of identifying addictive disease or disorder patients with favorable prognosis for pharmacological treatment (the patient can be treated/can respond favorably to treatment), comprising: a) obtaining genetic patterns (genetic variations) of two or more genetic regions (for example, genetic regions in genes that govern serotonin function, including genes that are associated with changes in serotonin transporter function and expression) of the patients, wherein the genetic patterns are predictive of addictive diseases or disorders; b) standardizing, with a processor (such as a CPU (central processing unit)/processor in a computer), the genetic patterns for each of the genetic regions, wherein the standardizing, comprises: mapping the possible range of genetic patterns to a range of conditional probabilities ranging from about 0 to about 1; and, c) operating, with a processor, upon the standardized genetic patterns using a computational procedure to transform the standardized genetic patterns into a composite result that has a diagnostic or predictive error for identifying addictive disease or disorder patients with favorable prognosis for pharmacological treatment lower than any of the individual genetic regions alone.

The polymorphisms identified herein also include their related miRNA, mRNA, ncRNA, or protein expression, levels, or states of function, or other biochemical products or chemical associations, which may serve as biomarkers.

In another aspect, the present invention provides a method of treating an addictive disease or disorder, comprising: administering to a patient in need thereof a therapeutically effective amount of an antagonist of the serotonin receptor 5-HT$_3$, wherein the patient's serotonin transporter gene SLC6A4 is known to have:
  (a) 3 or fewer of the genotypes selected from (Set (a)):
    i. the LS or SS genotype of the functional polymorphism serotonin transporter-linked polymorphic region 5-HTTLPR;
    ii. the TG or GG genotype of the single nucleotide polymorphism (SNP) rs1042173;
    iii. the GG genotype of the SNP rs1176713;
    iv. the AA genotype of the SNP rs1176719; and,
    v. the GG genotype of the SNP rs1672717;
  (b) 3 or more of the genotypes selected from (Set (b)):
    i. the LL genotype of the functional polymorphism serotonin transporter-linked polymorphic region 5-HTTLPR;
    ii. the AG or GG genotype of SNP rs1176719;
    iii. the GG or AG genotype of SNP rs1672717 (HTR3B); and,
    iv. the AA genotype of SNP rs2276307 (HTR3B);
  (c) 3 or more of the genotypes selected from (Set (c)):
    i. the LL genotype of the functional polymorphism serotonin transporter-linked polymorphic region 5-HTTLPR;
    ii. the TT genotype of rs1042173 (SERT);
    iii. the GT or GG genotype of rs10160548 (HTR3A);
    iv. the GA or GG genotype of rs1176746 (HTR3B); and,
    v. the GG genotype of rs12270070 (HTR3B).
  (d) a genotype selected from (Set (d)):
    i. the AG genotype of rs1150226;
    ii. the AG genotype of rs1150226 and the AC genotype of rs17614942;
    iii. the AG genotype of rs1150226, the LL genotype of 5-HTTLPR, and the TT genotype of rs1042173;
    iv. the AG genotype of rs1150226, the AC genotype of rs17614942, the LL genotype of 5-HTTLPR, and the TT genotype of rs1042173;
    v. the AC genotype of rs17614942; or
    vi. the AC genotype of rs17614942, the LL genotype of 5-HTTLPR, and the TT genotype of rs1042173;
  (e) the AA genotype of rs1176719;
  (f) the GG genotype of rs1176713;

(g) the AC genotype of rs17614942 and the LL genotype of 5-HTTLPR;
(h) the AG genotype of rs1150226 and at least one genotype selected from:
  i. the AC genotype of rs17614942; and
  ii. the LL genotype of 5-HTTLPR;
(i) the AA genotype of rs1176719 and at least one genotype selected from:
  i. the AC genotype of rs17614942;
  ii. the LL genotype of 5-HTTLPR; and,
  iii. the TT genotype of rs1042173;
(j) the AC genotype of rs17614942 and at least one genotype selected from:
  i. the AA genotype of rs1176719;
  ii. the LL genotype of 5-HTTLPR; and,
  iii. the TT genotype of rs1042173;
(k) the GG genotype of rs1176713 and at least one genotype selected from:
  i. the LL genotype of 5-HTTLPR; and,
  ii. the TT genotype of rs1042173;
(l) the GG genotype of rs1176713 and at least one genotype selected from:
  i. the AC genotype of rs17614942; and,
  ii. the LL genotype of 5-HTTLPR;
(m) the GG genotype of rs1176713 and at least one genotype selected from:
  i. the AC genotype of rs17614942; and,
  ii. the TT genotype of rs1042173;
(n) the GG genotype of rs1176713 and at least one genotype selected from:
  i. the AG genotype of rs1150226; and,
  ii. the TT genotype of rs1042173;
(o) the TT genotype of rs3758987 and at least one genotype selected from genotype sets (i)-(iv);
  i. the TT genotype of rs1042173;
  ii. the AA genotype of rs2276307 and the LL genotype of 5-HTTLPR;
  iii. the TT genotype of rs1042173 and the LL genotype of 5-HTTLPR; or
  iv. the TT genotype of rs1042173, the AA genotype of rs2276307, and the LL genotype of 5-HTTLPR; or
(p) the TC genotype of rs3758987 and at least one genotype selected from genotype sets (i)-(iv);
  i. the TT genotype of rs1042173;
  ii. the AA genotype of rs2276307 and the LL genotype of 5-HTTLPR;
  iii. the TT genotype of rs1042173 and the LL genotype of 5-HTTLPR; or
  iv. the TT genotype of rs1042173, the AA genotype of rs2276307, and the LL genotype of 5-HTTLPR.

In another aspect, the patient is known to have 2 or fewer genotypes (i)-(v) of Set (a).

In another aspect, the patient is known to have 1 or 0 genotypes (i)-(v) of Set (a).

In another aspect, the patient is known to have 0 genotypes (i)-(v) of Set (a).

In another aspect, the patient is known to have at least three of genotypes (i)-(iv) of Set (b).

In another aspect, the patient is known to have all 4 genotypes (i)-(iv) of Set (b).

In another aspect, the patient is known to have at least three of genotypes (i)-(v) of Set (c).

In another aspect, the patient is known to have 4 or 5 genotypes (i)-(v) of Set (c).

In another aspect, the patient is known to have 4 genotypes (i)-(v) of Set (c).

In another aspect, the patient is known to have all 5 genotypes (i)-(v) of Set (c).

In another aspect, the patient is known to have a genotype of Set (d).

In another aspect, the patient is known to have genotype (i) of Set (d).

In another aspect, the patient is known to have genotype (ii) of Set (d).

In another aspect, the patient is known to have genotype (iii) of Set (d).

In another aspect, the patient is known to have genotype (iv) of Set (d).

In another aspect, the patient is known to have genotype (v) of Set (d).

In another aspect, the patient is known to have genotype (vi) of Set (d).

In another aspect, the patient is known to have genotype Set (e).

In another aspect, the patient is known to have genotype Set (f).

In another aspect, the patient is known to have genotype Set (g).

In another aspect, the patient is known to satisfy genotype Set (h).

In another aspect, the patient is known to have genotype (i) of Set (h).

In another aspect, the patient is known to have genotype (ii) of Set (h).

In another aspect, the patient is known to have genotypes (i)-(ii) of Set (h).

In another aspect, the patient is known to satisfy genotype Set (i).

In another aspect, the patient is known to have at least two of genotypes (i)-(iii) of Set (i).

In another aspect, the patient is known to have all three genotypes (i)-(iii) of Set (i).

In another aspect, the patient is known to have genotype (i) of Set (i).

In another aspect, the patient is known to have genotype (ii) of Set (i).

In another aspect, the patient is known to have genotype (iii) of Set (i).

In another aspect, the patient is known to satisfy genotype Set (j).

In another aspect, the patient is known to have at least two of genotypes (i)-(iii) of Set (j).

In another aspect, the patient is known to have all three genotypes (i)-(iii) of Set (j).

In another aspect, the patient is known to have genotype (i) of Set (j).

In another aspect, the patient is known to have genotype (ii) of Set (j).

In another aspect, the patient is known to have genotype (iii) of Set (j).

In another aspect, the patient is known to satisfy genotype Set (k).

In another aspect, the patient is known to have genotype (i) of Set (k).

In another aspect, the patient is known to have genotype (ii) of Set (k).

In another aspect, the patient is known to have genotypes (i)-(ii) of Set (k).

In another aspect, the patient is known to satisfy genotype Set (l).

In another aspect, the patient is known to have genotype (i) of Set (l).

In another aspect, the patient is known to have genotype (ii) of Set (l).

In another aspect, the patient is known to have genotypes (i)-(ii) of Set (l).

In another aspect, the patient is known to satisfy genotype Set (m).

In another aspect, the patient is known to have genotype (i) of Set (m).

In another aspect, the patient is known to have genotype (ii) of Set (m).

In another aspect, the patient is known to have genotypes (i)-(ii) of Set (m).

In another aspect, the patient is known to satisfy genotype Set (n).

In another aspect, the patient is known to have genotype (i) of Set (n).

In another aspect, the patient is known to have genotype (ii) of Set (n).

In another aspect, the patient is known to have genotypes (i)-(ii) of Set (n).

The method of claim 1, wherein the patient is known to satisfy genotype set (o).

In another aspect, the patient is known to have at least two of genotypes (i)-(iv) of Set (o).

In another aspect, the patient is known to have at least three of genotypes (i)-(iv) of Set (o).

In another aspect, the patient is known to have all four of genotypes (i)-(iv) of Set (o).

In another aspect, the patient is known to satisfy genotype Set (p).

In another aspect, the patient is known to have at least two of genotypes (i)-(iv) of Set (p).

In another aspect, the patient is known to have at least three of genotypes (i)-(iv) of Set (p).

In another aspect, the patient is known to have all four of genotypes (i)-(iv) of Set (p).

In another aspect, the patient is known to have the LL and TT genotypes, and/or the AG genotype of rs1150226 and/or the AC genotype of rs17614942.

In another aspect, the patient is known to have the LL and TT genotypes, and/or the AG genotype of rs1150226, and/or the AC genotype of rs17614942, but not the GG genotype of rs1150226.

In another aspect, the patient is known to have the LL and TT genotypes, and/or the AG genotype of rs1150226, and/or the AC genotype of rs17614942, but not the TG genotype of rs1042173.

In another aspect, the patient is known to have the LL and TT genotypes, and/or the AG genotype of rs1150226, and/or the AC genotype of rs17614942, but not the GG genotype of rs1150226 or the TG genotype of rs1042173.

In another aspect, the patient is known to have the LL and TT genotypes, and/or the A+ genotype of rs1150226, and/or the AC genotype of rs17614942.

In another aspect, the patient is known to have the LL and TT genotypes, and/or the A+ genotype of rs1150226, and/or the AC genotype of rs17614942, but not the GG genotype of rs1150226.

In another aspect, the patient is known to have the LL and TT genotypes, and/or the A+ genotype of rs1150226, and/or the AC genotype of rs17614942, but not the TG genotype of rs1042173.

In another aspect, the patient is known to have the LL and TT genotypes, and/or the A+ genotype of rs1150226, and/or the AC genotype of rs17614942, but not the GG genotype of rs1150226 or the TG genotype of rs1042173.

In another aspect, the patient is known to have the LL and TT genotypes and/or the AC genotype of rs17614942.

In another aspect, the patient is known to have the LL and TT genotypes and/or the AG genotype of rs1150226 and the AC genotype of rs17614942.

In another aspect, the patient is known to have the the AG genotype of rs1150226 and/or the AC genotype of rs17614942.

Examples of the antagonist of the serotonin receptor 5-$HT_3$ include ondansetron, tropisetron, granisetron, palonosetron, dolasetron, and metocclopromide.

In another aspect, the antagonist of the serotonin receptor 5-$HT_3$ is ondansetron.

Examples of the dosage of the antagonist of the serotonin receptor 5-$HT_3$ (e.g., ondansetron) include: (a) about 0.1-1000 µg/kg per application; (b) about 1 µg/kg; (c) about 2 µg/kg; (d) about 3 µg/kg; (e) about 4 µg/kg; (f) about 5 µg/kg; (g) about 6 µg/kg; (h) about 7 µg/kg; (i) about 8 µg/kg; (j) about 9 µg/kg; (k) about 10, about 11, about 12, about 13, about 14, about 15, about 16, about 17, about 18, about 19, about 20, about 21, about 22, about 23, about 24, about 25, about 26, about 27, about 28, about 29, about 30, about 35, about 40, about 45, about 50, about 55, about 60, about 65, about 70, about 75, about 80, about 90, to about 100 µg/kg; and, (l) about 100, about 200, about 300, about 400, about 500, about 600, about 700, about 800, about 900, to about 1000 µg/kg.

Examples of the timing of administration include administering: (a) once a day, (b) twice a day, (c) once a week, (d) twice a week, (e) once a month, (f) twice a month, (g) once every 3 months, and (h) once every 6 months.

In another aspect, the addictive disease or disorder is selected from the group consisting of alcohol-related diseases and disorders, obesity-related diseases and disorders, eating disorders, impulse control disorders, nicotine-related disorders, amphetamine-related disorders, methamphetamine-related disorders, *Cannabis*-related disorders, cocaine-related disorders, hallucinogen use disorders, inhalant-related disorders, benzodiazepine abuse or dependence related disorders, opioid-related disorders, gambling, sexual disorders, computer use related disorders, and electronic use related disorders.

In another aspect, the addictive disease or disorder is an alcohol-related disease or disorder.

In another aspect, the alcohol-related disease or disorder is selected from the group consisting of early onset alcoholism, late onset alcoholism, alcohol-induced psychotic disorder with delusions, alcohol abuse, heavy drinking, excessive drinking, problem drinking, alcohol intoxication, alcohol withdrawal, alcohol intoxication delirium, alcohol withdrawal delirium, alcohol-induced persisting dementia, alcohol-induced persisting amnestic disorder, alcohol dependence, alcohol-induced psychotic disorder with hallucinations, alcohol-induced mood disorder, alcohol-induced or associated bipolar disorder, alcohol-induced or associated post traumatic stress disorder, alcohol-induced anxiety disorder, alcohol-induced sexual dysfunction, alcohol-induced sleep disorder, alcohol-induced or associated gambling disorder, alcohol-induced or associated sexual disorder, alcohol-related disorder not otherwise specified, alcohol intoxication, and alcohol withdrawal.

In another aspect, the alcohol-related disease or disorder is early onset alcoholism. In another aspect, the alcohol-related disease or disorder is late onset alcoholism.

In another aspect, the response from the treatment, comprises: a reduction in drinking. Examples of reduction in drinking include, but are not limited to reduction of (a)

heavy drinking, (b) excessive drinking, (c) drinks/day, (d) percentage of subjects not drinking heavily, (e) drinks/drinking day, (f) percentage of subjects with no heavy drinking, and (g) percentage of subjects who are abstinent.

In another aspect, the method reduces the quantity of alcohol consumed compared with the amount of alcohol consumed before said treatment or compared with a control subject not receiving said treatment. In another aspect, the alcohol consumption comprises heavy drinking or excessive drinking.

In another aspect, the method improves the physical or psychological sequelae associated with alcohol consumption compared with a control subject not receiving said treatment.

In another aspect, the method increases the abstinence rate of said subject compared with a control subject not receiving said treatment.

In another aspect, the method reduces the average level of alcohol consumption compared with the level before said treatment or compared with a control subject not receiving said treatment.

In another aspect, the method reduces alcohol consumption and increases abstinence compared with the alcohol consumption and abstinence before said treatment or compared with a control subject not receiving said treatment.

In another aspect, the subject is submitted to a psychosocial management program.

In another aspect, the psychosocial management program is selected from the group consisting of Brief Behavioral Compliance Enhancement Treatment; Cognitive Behavioral Coping Skills Therapy; Motivational Enhancement Therapy; Twelve-Step Facilitation Therapy; Combined Behavioral Intervention; Medical Management; psychoanalysis; psychodynamic treatment; Biopsychosocial, Report, Empathy, Needs, Direct Advice and Assessment; and, computer-delivered education or treatment.

In another aspect, the subject is further subjected to hypnosis or acupuncture.

In another aspect, effective amounts of at least two antagonists are administered.

In another aspect, effective amounts of at least three antagonists are administered.

In another aspect, the present invention provides a method of selecting patients with an addictive disease or disorder who will be responsive to treatment with an antagonist of the serotonin receptor 5-HT$_3$, comprising: determining whether he patient's serotonin transporter gene SLC6A4 has:
  (a) 3 or fewer of the genotypes selected from (Set (a)):
    i. the LS or SS genotype of the functional polymorphism serotonin transporter-linked polymorphic region 5-HTTLPR;
    ii. the TG or GG genotype of the single nucleotide polymorphism (SNP) rs1042173;
    iii. the GG genotype of the SNP rs1176713;
    iv. the AA genotype of the SNP rs1176719; and,
    v. the GG genotype of the SNP rs1672717;
  (b) 3 or more of the genotypes selected from (Set (b)):
    v. the LL genotype of the functional polymorphism serotonin transporter-linked polymorphic region 5-HTTLPR;
    vi. the AG or GG genotype of SNP rs1176719;
    vii. the GG or AG genotype of SNP rs1672717 (HTR3B); and,
    viii. the AA genotype of SNP rs2276307 (HTR3B);
  (c) 3 or more of the genotypes selected from (Set (c)):
    i. the LL genotype of the functional polymorphism serotonin transporter-linked polymorphic region 5-HTTLPR;
    ii. the TT genotype of rs1042173 (SERT);
    iii. the GT or GG genotype of rs10160548 (HTR3A);
    iv. the GA or GG genotype of rs1176746 (HTR3B); and,
    v. the GG genotype of rs12270070 (HTR3B).
  (d) a genotype selected from (Set (d)):
    i. the AG genotype of rs1150226;
    ii. the AG genotype of rs1150226 and the AC genotype of rs17614942;
    iii. the AG genotype of rs1150226, the LL genotype of 5-HTTLPR, and the TT genotype of rs1042173;
    iv. the AG genotype of rs1150226, the AC genotype of rs17614942, the LL genotype of 5-HTTLPR, and the TT genotype of rs1042173;
    v. the AC genotype of rs17614942; or
    vi. the AC genotype of rs17614942, the LL genotype of 5-HTTLPR, and the TT genotype of rs1042173;
  (e) the AA genotype of rs1176719;
  (f) the GG genotype of rs1176713;
  (g) the AC genotype of rs17614942 and the LL genotype of 5-HTTLPR;
  (h) the AG genotype of rs1150226 and at least one genotype selected from:
    iii. the AC genotype of rs17614942; and
    iv. the LL genotype of 5-HTTLPR;
  (i) the AA genotype of rs1176719 and at least one genotype selected from:
    iv. the AC genotype of rs17614942;
    v. the LL genotype of 5-HTTLPR; and,
    vi. the TT genotype of rs1042173;
  (j) the AC genotype of rs17614942 and at least one genotype selected from:
    iv. the AA genotype of rs1176719;
    v. the LL genotype of 5-HTTLPR; and,
    vi. the TT genotype of rs1042173;
  (k) the GG genotype of rs1176713 and at least one genotype selected from:
    iii. the LL genotype of 5-HTTLPR; and,
    iv. the TT genotype of rs1042173;
  (l) the GG genotype of rs1176713 and at least one genotype selected from:
    iii. the AC genotype of rs17614942; and,
    iv. the LL genotype of 5-HTTLPR;
  (m) the GG genotype of rs1176713 and at least one genotype selected from:
    iii. the AC genotype of rs17614942; and,
    iv. the TT genotype of rs1042173;
  (n) the GG genotype of rs1176713 and at least one genotype selected from:
    iii. the AG genotype of rs1150226; and,
    iv. the TT genotype of rs1042173;
  (o) the TT genotype of rs3758987 and at least one genotype selected from genotype sets (i)-(iv);
    v. the TT genotype of rs1042173;
    vi. the AA genotype of rs2276307 and the LL genotype of 5-HTTLPR;
    vii. the TT genotype of rs1042173 and the LL genotype of 5-HTTLPR; or
    viii. the TT genotype of rs1042173, the AA genotype of rs2276307, and the LL genotype of 5-HTTLPR; or
  (p) the TC genotype of rs3758987 and at least one genotype selected from genotype sets (i)-(iv);
    v. the TT genotype of rs1042173;

vi. the AA genotype of rs2276307 and the LL genotype of 5-HTTLPR;
vii. the TT genotype of rs1042173 and the LL genotype of 5-HTTLPR; or
viii. the TT genotype of rs1042173, the AA genotype of rs2276307, and the LL genotype of 5-HTTLPR.

In another aspect, the method of selecting, further comprises:
administering an antagonist of the serotonin receptor 5-HT$_3$ to the patient, if the patient satisfies one of the (a)-(p) criteria.

In another aspect, the present invention provides a method of treating a patient with an addictive disease or disorder, comprising:
a. determining whether the patient, in the patient's serotonin transporter gene SLC6A4, satisfies one of the (a)-(p) criteria; and,
b. administering an antagonist of the serotonin receptor 5-HT$_3$ to the patient, if the patient satisfies one of the (I)-(IV) criteria.

In another aspect, the present invention provides a method of predicting a response to treatment for an addictive disease or disorder in a subject comprising: determining whether the patient, in the patient's serotonin transporter gene SLC6A4, satisfies one of the (a)-(p) criteria.

In another aspect, the present invention further comprises: administering to a patient in need thereof a therapeutically effective amount of a second therapeutic agent (e.g., topiramate and/or naltrexone). The present invention further encompasses the use of adjunctive treatments and therapy such as psychosocial management regimes, hypnosis, and acupuncture.

In another aspect, the present invention provides compositions and methods for treating an addictive disease or disorder using pharmaceutical compositions, comprising: effective amounts of ondansetron, topiramate and/or naltrexone.

In another aspect, the present invention provides a method of treating an addictive disease or disorder, comprising: administering to a patient in need thereof a therapeutically effective amount of an antagonist of the serotonin receptor 5-HT$_3$, wherein the patient, in the patient's serotonin transporter gene SLC6A4, is known to have the TG genotype of the single nucleotide polymorphism rs1042173. In another aspect, the patient further is known to have the LL genotype of the functional polymorphism serotonin transporter-linked polymorphic region 5-HTTLPR of the serotonin transporter gene SLC6A4.

In another aspect, the present invention provides a method of predicting a response to treatment for an addictive disease or disorder in a patient comprising: determining whether the patient has the TG genotype of the single nucleotide polymorphism rs1042173 of the serotonin transporter gene SLC6A4. The presence of the TG genotype is an indication that the patient will respond to treatment for an addictive disease or disorder. In another aspect, the invention further comprises: determining if the patient further has the LL genotype of the functional polymorphism serotonin transporter-linked polymorphic region 5-HTTLPR of the serotonin transporter gene SLC6A4.

In another aspect, the method predicts the response to treatment with at least one antagonist of the serotonin receptor 5-HT$_3$ (e.g., ondansetron).

In another aspect, the present invention provides a method of selecting patients with an addictive disease or disorder who will be responsive to treatment with an antagonist of the serotonin receptor 5-HT$_3$, comprising: determining whether the patient has the TG genotype of the single nucleotide polymorphism rs1042173 of the serotonin transporter gene SLC6A4. In another aspect, the invention further comprises: determining if the patient further has the LL genotype of the functional polymorphism serotonin transporter-linked polymorphic region 5-HTTLPR of the serotonin transporter gene SLC6A4.

In another aspect, the present invention provides a method of treating a patient with an addictive disease or disorder, comprising:
a) determining whether the patient has the TG genotype of the single nucleotide polymorphism rs1042173 of the serotonin transporter gene SLC6A4; and
b) administering at least one antagonist of the serotonin receptor 5-HT$_3$ to the patient having the TG genotype.

In another aspect, the invention further comprises: determining if the patient further has the LL genotype of the functional polymorphism serotonin transporter-linked polymorphic region 5-HTTLPR of the serotonin transporter gene SLC6A4.

In another aspect, the present invention provides a method of treating an addictive disease or disorder, comprising: administering to a patient in need thereof a therapeutically effective amount of an antagonist of the serotonin receptor 5-HT$_3$, wherein the patient, in the patient's serotonin transporter gene SLC6A4, is known to have the the AA or AC genotype of the single nucleotide polymorphism rs17614942 (5HT$_3$b). In another aspect, the patient further is known to have the LL genotype of the functional polymorphism serotonin transporter-linked polymorphic region 5-HTTLPR of the serotonin transporter gene SLC6A4.

In another aspect, the present invention provides a method of predicting a response to treatment for an addictive disease or disorder in a patient comprising: determining whether the patient has the AA or AC genotype of the single nucleotide polymorphism rs17614942 (5HT$_3$b) of the serotonin transporter gene SLC6A4. In another aspect, the invention further comprises: determining if the patient further has the LL genotype of the functional polymorphism serotonin transporter-linked polymorphic region 5-HTTLPR of the serotonin transporter gene SLC6A4.

In another aspect, the method predicts the response to treatment with at least one antagonist of the serotonin receptor 5-HT$_3$ (e.g., ondansetron).

In another aspect, the present invention provides a method of selecting patients with an addictive disease or disorder who will be responsive to treatment with an antagonist of the serotonin receptor 5-HT$_3$, comprising: determining whether the patient has the AA or AC genotype of the single nucleotide polymorphism rs17614942 (5HT$_3$b) of the serotonin transporter gene SLC6A4. In another aspect, the invention further comprises: determining if the patient further has the LL genotype of the functional polymorphism serotonin transporter-linked polymorphic region 5-HTTLPR of the serotonin transporter gene SLC6A4.

In another aspect, the present invention provides a method of treating a patient with an addictive disease or disorder, comprising:
a) determining whether the patient has the AA or AC genotype of the single nucleotide polymorphism rs17614942 (5HT$_3$b) of the serotonin transporter gene SLC6A4; and
b) administering at least one antagonist of the serotonin receptor 5-HT$_3$ to the patient having the TG genotype.

In another aspect, the invention further comprises: determining if the patient further has the LL genotype of the functional polymorphism serotonin transporter-linked polymorphic region 5-HTTLPR of the serotonin transporter gene SLC6A4.

In another aspect, the present invention provides a method of treating an addictive disease or disorder, comprising: administering to a patient in need thereof a therapeutically effective amount of an antagonist of the serotonin receptor 5-HT$_3$, wherein the patient, in the patient's serotonin transporter gene SLC6A4, is known to have the the AA or AC genotype of the single nucleotide polymorphism rs4938056 (5HT$_3$b). In another aspect, the patient further is known to have the LL genotype of the functional polymorphism serotonin transporter-linked polymorphic region 5-HTTLPR of the serotonin transporter gene SLC6A4.

In another aspect, the present invention provides a method of predicting a response to treatment for an addictive disease or disorder in a patient comprising: determining whether the patient has the AA or AC genotype of the single nucleotide polymorphism rs4938056 (5HT$_3$b) of the serotonin transporter gene SLC6A4. In another aspect, the invention further comprises: determining if the patient further has the LL genotype of the functional polymorphism serotonin transporter-linked polymorphic region 5-HTTLPR of the serotonin transporter gene SLC6A4.

In another aspect, the method predicts the response to treatment with at least one antagonist of the serotonin receptor 5-HT$_3$ (e.g., ondansetron).

In another aspect, the present invention provides a method of selecting patients with an addictive disease or disorder who will be responsive to treatment with an antagonist of the serotonin receptor 5-HT$_3$, comprising: determining whether the patient has the AA or AC genotype of the single nucleotide polymorphism rs4938056 (5HT$_3$b) of the serotonin transporter gene SLC6A4. In another aspect, the invention further comprises: determining if the patient further has the LL genotype of the functional polymorphism serotonin transporter-linked polymorphic region 5-HTTLPR of the serotonin transporter gene SLC6A4.

In another aspect, the present invention provides a method of treating a patient with an addictive disease or disorder, comprising:
 a) determining whether the patient has the AA or AC genotype of the single nucleotide polymorphism rs4938056 (5HT$_3$b) of the serotonin transporter gene SLC6A4; and
 b) administering at least one antagonist of the serotonin receptor 5-HT$_3$ to the patient having the TG genotype.

In another aspect, the invention further comprises: determining if the patient further has the LL genotype of the functional polymorphism serotonin transporter-linked polymorphic region 5-HTTLPR of the serotonin transporter gene SLC6A4.

One of ordinary skill in the art will appreciate that in some instances a patient being treated for an addictive disorder is not necessarily dependent. Such patients include, for example, patients who abuse alcohol, drink heavily, drink excessively, are problem drinkers, or are heavy drug users. The present invention provides compositions and methods for treating or preventing these behaviors in non-dependent patients.

In another aspect, the present invention provides compositions and methods for improving the physical or psychological sequelae associated with alcohol consumption compared with a control subject not receiving the treatment.

In another aspect, the present invention provides compositions and methods for increasing the abstinence rate of a subject compared with a control subject not receiving the treatment.

In another aspect, the present invention provides compositions and methods for reducing the average level of alcohol consumption in a subject compared with the level of alcohol consumption before the treatment or compared with the level of alcohol consumption by a control subject not receiving the treatment.

In another aspect, the present invention provides compositions and methods for reducing alcohol consumption and for increasing abstinence compared with the alcohol consumption by the subject before treatment or with a control subject not receiving the treatment.

In another aspect, the present invention provides compositions and methods for treating a subject with a predisposition to early-onset alcoholism.

In another aspect, the present invention provides compositions and methods for treating a subject with a predisposition to late-onset alcoholism.

One of ordinary skill in the art will appreciate that there are multiple parameters or characteristics of alcohol consumption which may characterize a subject afflicted with an alcohol-related disease or disorder. It will also be appreciated that combination therapies may be effective in treating more than one parameter, and that there are multiple ways to analyze the effectiveness of treatment. The parameters analyzed when measuring alcohol consumption or frequency of alcohol consumption include, but are not limited to, heavy drinking days, number of heavy drinking days, average drinking days, number of drinks per day, days of abstinence, number of individuals not drinking heavily or abstinent over a given time period, and craving. Both subjective and objective measures can be used to analyze the effectiveness of treatment. For example, a subject can self-report according to guidelines and procedures established for such reporting. The procedures can be performed at various times before, during, and after treatment. Additionally, assays are available for measuring alcohol consumption. These assays include breath alcohol meter readings, measuring serum CDT and GGT levels, and measuring 5-HTOL urine levels.

When combination therapy is used, the timing of administration of the combination can vary. First example, the first compound and a second compound can be administered nearly simultaneously. Other examples include (a) the first compound being administered prior to the second compound, (b) the first compound being administered subsequent to the second compound, and (c) if three or more compounds are administered, one of ordinary skill in the art will appreciate that the three or more compounds can be administered simultaneously or in varying order.

In another aspect, the present invention provides a method of treating, comprising administering at least two compounds selected from the group consisting of topiramate, ondansetron, and naltrexone. In one aspect, topiramate and ondansetron are used.

Because the serotonin system has intimate connections and is modulated in the brain by other neurotransmitters, particularly dopamine, GABA, glutamate, opioids, and cannabinoid, the present invention also encompasses the use of medications and drugs that affect the structure and function of these other neurotransmitters when combined with any serotonergic agent (including ondansetron). In one aspect, the combination is efficacious for individuals with the polymorphisms described herein. In another aspect, the present invention provides compositions, compounds and methods that are associated with these co-modulating neurotransmitters (i.e., dopamine, GABA, glutamate, opioids, and cannabinoid), including, but not limited to, topiramate, baclofen, gabapentin, naltrexone, nalmefene, and rimonabant-in combination with any serotonergic agent (including but not limited to ondansetron, selective serotonin re-uptake blockers, and other agonists or antagonists of other serotonin receptors or moieties) can produce a therapeutic effect to improve the clinical outcomes for individuals who use, abuse, misuse, or are dependent on alcohol. Because abused drugs are predicted to work through similar mechanisms, the present invention further provides combinations of these co-modulating drugs with any other serotonergic agent to be used to treat individuals with any substance use, abuse, misuse, dependence, or habit-forming behavior with the polymorphisms described herein or anywhere else in the serotonergic or co-modulating neurotransmitter systems (i.e., dopamine, GABA, glutamate, opioids, and cannabinoid), either alone or in combination.

In a further aspect, the combination pharmacotherapy treatment is used in conjunction with behavioral modification or therapy.

The dosage of the active compound(s) being administered will depend on the condition being treated, the particular compound, and other clinical factors such as age, sex, weight, and health of the subject being treated, the route of administration of the compound(s), and the type of composition being administered (tablet, gel cap, capsule, solution, suspension, inhaler, aerosol, elixir, lozenge, injection, patch, ointment, cream, etc.). It is to be understood that the present invention has application for both human and veterinary use.

The drugs can be administered in formulations that contain all drugs being used, or the drugs can be administered separately. In some cases, it is anticipated that multiple doses/times of administration will be useful. The present invention further provides for varying the length of time of treatment.

In another aspect, the present invention provides a composition comprising: an antagonist of the serotonin receptor 5-$HT_3$. In another aspect, the composition further comprises a second therapeutic agent. In another aspect, the composition further comprises a third therapeutic agent.

Topiramate ($C_{12}H_{21}NO_8S$; IUPAC name: 2,3:4,5-Bis-O-(1-methylethylidene)-beta-D-fructopyranose sulfamate; CAS Registry No. 97240-79-4) is disclosed herein as a drug useful in combination drug therapy. Examples of topiramate dosages include: (a) about 15, about 25, about 35, about 35, about 55, about 65, about 75, about 85, about 95, about 100, about 200, about 300, about 400, about 500, about 600, about 700, about 800, about 900, about 1000, about 1100, about 1200, about 1300, about 1400, about 1500, about 1600, about 1700, about 1800, about 1900, about 2000, about 2100, about 2200, about 2300, about 2400, to about 2500 mg/day, (b) about 25-1000 mg/day, (c) about 50, about 60, about 70, about 80, about 90, about 100, about 200, about 300, about 400, to about 500 mg/day, (f) about 275 mg/day, (g) about 1 mg/day, (h) about 1 mg/kg, (i) about 10 mg/kg, (j) about 100 mg/kg, and (k) about 0.1, about 0.2, about 0.3, about 0.4, about 0.5, about 0.6, about 0.7, about 0.8, about 0.9, about 1.0, about 2, about 3, about 4, about 5, about 6, about 7, about 8, about 9, about 10, about 20, about 30, about 40, about 50, about 60, about 70, about 80, about 90 to about 100 mg/kg/day.

An aspect of psychotropic drugs is to produce weight gain. These increases in weight gain can induce a range of metabolic problems including abnormal sugar, fat, and carbohydrate metabolism. Because topiramate can cause weight loss and improve endocrine function, it is proposed herein that topiramate may be used to ameliorate weight gain caused by other psychotropic drugs with which it is combined as well as alcohol and any other abused drugs.

An adverse event of topiramate is cognitive impairment. In the general population, this is reported by 2.4% of individuals who take topiramate (Johnson & Johnson Pharmaceutical Research & Development. Investigator's Brochure: Topiramate (RWJ-17021-000), 10th ed.; December 2005). In the substance abuse field, the occurrence rate of cognitive impairment is about 18.7% (Johnson B A, Ait-Daoud N, Bowden C L et al. Oral topiramate for treatment of alcohol dependence: a randomized controlled trial. Lancet 2003, 361:1677-1685). Topiramate-associated cognitive effects are due to its anti-glutaminergic properties. It is, therefore, not obvious that ondansetron, a serotonin-3 receptor antagonist, will alleviate these complaints of cognitive impairment. Ondansetron appears to have cholinergic effects, perhaps through interactions with the GABA system that seem to ameliorate topiramate-associated cognitive impairment. Hence, the rate of cognitive impairment reported by this triple combination would be less than that for topiramate on its own.

Ondansetron ($C_{18}H_{19}N_3O$; CAS Registry No. 99614-02-5; IUPAC name: 9-methyl-3-[(2-methyl-1H-imidazol-1-yl)methyl]-1,2,3,9-tetrahydrocarbazol-4-one) is disclosed herein as a drug useful alone or as part of combination drug therapy. Ondansetron is a 5-$HT_3$ receptor antagonist and has functionally opposite effects to SSRIs and blocks serotonin agonism at the 5-$HT_3$ receptor. The dosage and treatment regimen for administering ondansetron when it is being used as one compound of a combination therapy can be varied based on the other drug or drugs with which it is being administered, or based on other criteria such as the age, sex, health, and weight of the subject.

The present invention further provides for the use of other drugs such as naltrexone ($C_{20}H_{23}NO_4$; 17-(Cyclopropylmethyl)-4,5a-epoxy-3,14-dihydroxymorphinan-6-one hydrochloride; CAS Registry No. 16590-41-3) as part of the drug combination therapy disclosed herein. Examples of naltrexone dosages include: (a) 10 mg/day, (b) 50 mg/day, (c) 100 mg/day, (d) 1, 2, 3, 4, 5, 6, 7, 8, 9, 10, 20, 30, 40, 50, 60, 70, 80, 90, 100, 150, 200, 250, to 300 mg per application, (e) 10-50 mg per application, and (f) 25 mg per application.

Naltrexone also has adverse events—nausea and vomiting—that reduce compliance to it. Indeed, about 15% of individuals in alcohol trials are unable to tolerate a naltrexone dose of 50 mg/day. This has led to the development of depot formulations that release naltrexone slowly to reduce the incidence of nausea and vomiting. Nevertheless, these depot formulation(s) appear to have similar compliance rates to the oral form of the medication. Ondansetron reduces nausea and decreases vomiting by slowing gut motility. Therefore, a combination that adds ondansetron to naltrexone will diminish the nausea and vomiting caused by naltrexone. This is a therapeutic advance because many more people will be able to tolerate the treatment due to increased compliance, and higher doses than the typically administered naltrexone dose of 50 mg/day can be given to improve the therapeutic response.

The present invention provides for multiple methods for delivering the compounds of the invention. The compounds may be provided, for example, as pharmaceutical compositions in multiple formats as well, including, but not limited to, tablets, capsules, pills, lozenges, syrups, ointments, creams, elixirs, suppositories, suspensions, inhalants, injections (including depot preparations), and liquids.

The invention further encompasses treating and preventing obesity, i.e., for affecting weight loss and preventing weight gain. Obesity is a disorder characterized by the accumulation of excess fat in the body. Obesity has been recognized as one of the leading causes of disease and is emerging as a global problem. Increased instances of complications such as hypertension, non-insulin-dependent diabetes mellitus, arteriosclerosis, dyslipidemia, certain forms of cancer, sleep apnea, and osteoarthritis have been related to increased instances of obesity in the general population In one aspect, the invention encompasses administering to a subject in need thereof a combination therapy to induce weight loss. For example, subjects having a BMI of greater than about 25 (25.0-29.9 is considered overweight) are identified for treatment. In one aspect, the individuals have a BMI of greater than 30 (30 and above is considered obese). In another aspect, a subject may be targeted for treatment to prevent weight gain. In one embodiment, an individual is instructed to take at least one compound of the invention at least once daily and at least a second compound of the invention at least once daily. The compound may be in the form of, for example, a tablet, a lozenge, a liquid, etc. In one aspect, a third compound is also taken daily. In one embodiment, compounds may be taken more than once daily. In another embodiment, compounds are taken less than once daily. The dosages can be determined based on what is known in the art or what is determined to be best for a subject of that age, sex, health, weight, etc. Compounds useful for treating obesity according to the methods of the invention, include, but are not limited to, topiramate, naltrexone, and ondansetron. See Weber (U.S. Pat. Pub. No. 20070275970) and McElroy (U.S. Pat. No. 6,323,236) for additional information and techniques for administering drugs useful for treating obesity, addictive disorders, and impulse control disorders, and for determining dosage schemes.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amines, trisubstituted cycloalkyl amines, cycloalkenyl amines, di(cycloalkenyl) amines, tri(cycloalkenyl) amines, substituted cycloalkenyl amines, disubstituted cycloalkenyl amines, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Psychosocial Intervention and Management

The drug combination treatments of the present invention can be further supplemented by providing to subjects a form of psychosocial intervention and/or management, such as Brief Behavioral Compliance Enhancement Treatment (BBCET). BBCET, a standardized, manual-guided, brief (i.e., delivered in about 15 minutes), psychosocial adherence enhancement procedure, emphasizes that medication compliance is crucial to changing participants' drinking behavior (Johnson et al., Brief Behavioral Compliance Enhancement Treatment (BBCET) manual. In: Johnson B A, Ruiz P, Galanter M, eds. Handbook of clinical alcoholism treatment. Baltimore, Md.: Lippincott Williams & Wilkins; 2003, 282-301). Brief interventions (Edwards et al., J. Stud. Alcohol. 1977, 38:1004-1031) such as BBCET, have been shown to benefit treatment of alcohol dependence. BBCET was modeled on the clinical management condition in the National Institute of Mental Health collaborative depression trial, which was used as an adjunct to the medication condition for that study (Fawcett et al. Psychopharmacol Bull. 1987, 23:309-324). BBCET has been used successfully as the psychosocial treatment platform in the single-site and multisite efficacy trials of topiramate for treating alcohol dependence (Johnson et al., Lancet. 2003, 361:1677-1685; Johnson et al., JAMA, 2007, 298:1641-1651). It is delivered by trained clinicians, including nurse practitioners and other non-specialists. Uniformity and consistency of BBCET delivery are ensured by ongoing training and supervision. BBCET is copyrighted material (Johnson et al., Brief Behavioral Compliance Enhancement Treatment (BBCET) manual. In: Johnson B A, Ruiz P, Galanter M, eds. Handbook of clinical alcoholism treatment. Baltimore, Md.: Lippincott Williams & Wilkins; 2003, 282-301).

The present invention further encompasses the use of psychosocial management regimens other than BBCET, including, but not limited to, Cognitive Behavioral Coping Skills Therapy (CBT) (Project MATCH Research Group. Matching Alcoholism Treatments to Client Heterogeneity: Project MATCH posttreatment drinking outcomes. J Stud Alcohol. 1997; 58:7-29), Motivational Enhancement Therapy (MET) (Project MATCH Research Group. Matching Alcoholism Treatments to Client Heterogeneity: Project MATCH posttreatment drinking outcomes. J. Stud. Alcohol. 1997, 58:7-29), Twelve-Step Facilitation Therapy (TSF) (Project MATCH Research Group. Matching Alcoholism Treatments to Client Heterogeneity: Project MATCH posttreatment drinking outcomes. J. Stud. Alcohol. 1997, 58:7-29), Combined Behavioral Intervention (CBI), (Anton et al., JAMA, 2006, 295:2003-2017) Medical Management (MM)

(Anton et al., JAMA, 2006, 295:2003-2017), or the Biopsychosocial, Report, Empathy, Needs, Direct advice, and Assessment (BRENDA) model (Garbutt et al., JAMA, 2005, 293:1617-1625). The present invention further encompasses the use of alternative interventions such as hypnosis or acupuncture to assist in treating an addictive disease or disorder.

The psychosocial management programs can be used before, during, and after treating the subject with the combination drug therapy of the invention.

One of ordinary skill in the art will recognize that psychosocial management procedures, as well as alternative interventions such as hypnosis or acupuncture, can also be used in conjunction with combination drug therapy to treat addictive and impulse-related disorders other than alcohol-related diseases and disorders.

The present invention further encompasses the use of combination pharmacotherapy and behavioral (psychosocial) intervention or training to treat other addictive and/or impulse control disorders.

For example, binge eating disorder (BED) is characterized by discrete periods of binge eating during which large amounts of food are consumed in a discrete period of time and a sense of control over eating is absent. Persons with bulimia nervosa have been reported to have electroencephalographic abnormalities and to display reduced binge eating in response to the anti-epileptic drug phenytoin. In addition, in controlled trials in patients with epilepsy, topiramate was associated with suppression of appetite and weight loss unrelated to binge eating. Ondansetron has been shown to reduce binge eating.

BED is a subset of a larger classification of mental disorders broadly defined as Impulse Control Disorders (ICDs) characterized by harmful behaviors performed in response to irresistible impulses. It has been suggested that ICDs may be related to obsessive-compulsive disorder or similarly, maybe forms of obsessive-compulsive disorders. It has also been hypothesized that ICDs may be related to mood disorder or may be forms of affective spectrum disorder, a hypothesized family of disorders sharing at least one common physiologic abnormality with major depression. In the Diagnostic and Statistical Manual of Mental Disorders (DSM-IV), the essential feature of an ICD is the failure to resist an impulse, drive, or temptation to perform an act that is harmful to the person or to others. For most ICDs, the individual feels an increasing sense of tension or arousal before committing the act, and then experiences pleasure, gratification, or release at the time of committing the act. After the act is performed, there may or may not be regret or guilt. ICDs are listed in a residual category, the ICDs Not Elsewhere Classified, which includes intermittent explosive disorder (IED), kleptomania, pathological gambling, pyromania, trichotillomania, and ICDs not otherwise specified (NOS). Examples of ICDs NOS are compulsive buying or shopping, repetitive self-mutilation, nonparaphilic sexual addictions, severe nail biting, compulsive skin picking, personality disorders with impulsive features, attention deficit/hyperactivity disorder, eating disorders characterized by binge eating, and substance use disorders.

Many drugs can cause physical and/or psychological addiction. Those most well known drugs include opiates, such as heroin, opium and morphine; sympathomimetics, including cocaine and amphetamines; sedative-hypnotics, including alcohol, benzodiazepines, and barbiturates; and nicotine, which has effects similar to opioids and sympathomimetics. Drug addiction is characterized by a craving or compulsion for taking the drug and an inability to limit its intake. Additionally, drug dependence is associated with drug tolerance, the loss of effect of the drug following repeated administration, and withdrawal, the appearance of physical and behavioral symptoms when the drug is not consumed. Sensitization occurs if repeated administration of a drug leads to an increased response to each dose. Tolerance, sensitization, and withdrawal are phenomena evidencing a change in the central nervous system resulting from continued use of the drug. This change motivates the addicted individual to continue consuming the drug despite serious social, legal, physical, and/or professional consequences.

Attention-deficit disorders include, but are not limited to, Attention-Deficit/Hyperactivity Disorder, Predominately Inattentive Type; Attention-Deficit/Hyperactivity Disorder, Predominately Hyperactivity-Impulsive Type; Attention-Deficit/Hyperactivity Disorder, Combined Type; Attention-Deficit/Hyperactivity Disorder not otherwise specified (NOS); Conduct Disorder; Oppositional Defiant Disorder; and Disruptive Behavior Disorder not otherwise specified (NOS).

Depressive disorders include, but are not limited to, Major Depressive Disorder, Recurrent; Dysthymic Disorder; Depressive Disorder not otherwise specified (NOS); and Major Depressive Disorder, Single Episode.

Parkinson's disease includes, but is not limited to, neuroleptic-induced parkinsonism.

Addictive disorders include, but are not limited to, eating disorders, impulse control disorders, alcohol-related disorders, nicotine-related disorders, amphetamine-related disorders, *Cannabis*-related disorders, cocaine-related disorders, gambling, sexual disorders, hallucinogen use disorders, inhalant-related disorders, and opioid-related disorders, all of which are further subclassified as listed below.

Eating disorders include, but are not limited to, Bulimia Nervosa, Nonpurging Type; Bulimia Nervosa, Purging Type; and Eating Disorder not otherwise specified (NOS).

Impulse control disorders include, but are not limited to, Intermittent Explosive Disorder, Kleptomania, Pyromania, Pathological Gambling, Trichotillomania, and Impulse Control Disorder not otherwise specified (NOS).

Nicotine-related disorders include, but are not limited to, Nicotine Dependence, Nicotine Withdrawal, and Nicotine-Related Disorder not otherwise specified (NOS).

Amphetamine-related disorders include, but are not limited to, Amphetamine Dependence, Amphetamine Abuse, Amphetamine Intoxication, Amphetamine Withdrawal, Amphetamine Intoxication Delirium, Amphetamine-Induced Psychotic Disorder with delusions, Amphetamine-Induced Psychotic Disorders with hallucinations, Amphetamine-Induced Mood Disorder, Amphetamine-Induced Anxiety Disorder, Amphetamine-Induced Sexual Dysfunction, Amphetamine-Induced Sleep Disorder, Amphetamine Related Disorder not otherwise specified (NOS), Amphetamine Intoxication, and Amphetamine Withdrawal.

*Cannabis*-related disorders include, but are not limited to, *Cannabis* Dependence; *Cannabis* Abuse; *Cannabis* Intoxication; *Cannabis* Intoxication Delirium; *Cannabis*-Induced Psychotic Disorder, with delusions; *Cannabis*-Induced Psychotic Disorder with hallucinations; *Cannabis*-Induced Anxiety Disorder; *Cannabis*-Related Disorder not otherwise specified (NOS); and *Cannabis* Intoxication.

Cocaine-related disorders include, but are not limited to, Cocaine Dependence, Cocaine Abuse, Cocaine Intoxication, Cocaine Withdrawal, Cocaine Intoxication Delirium, Cocaine-Induced Psychotic Disorder with delusions, Cocaine-Induced Psychotic Disorders with hallucinations, Cocaine-Induced Mood Disorder, Cocaine-Induced Anxiety Disorder, Cocaine-Induced Sexual Dysfunction, Cocaine-Induced Sleep Disorder, Cocaine-Related Disorder not otherwise specified (NOS), Cocaine Intoxication, and Cocaine Withdrawal.

Hallucinogen-use disorders include, but are not limited to, Hallucinogen Dependence, Hallucinogen Abuse, Hallucinogen Intoxication, Hallucinogen Withdrawal, Hallucinogen Intoxication Delirium, Hallucinogen-Induced Psychotic Disorder with delusions, Hallucinogen-Induced Psychotic Disorder with hallucinations, Hallucinogen-Induced Mood Disorder, Hallucinogen-Induced Anxiety Disorder, Hallucinogen-Induced Sexual Dysfunction, Hallucinogen-Induced Sleep Disorder, Hallucinogen Related Disorder not otherwise specified (NOS), Hallucinogen Intoxication, and Hallucinogen Persisting Perception Disorder (Flashbacks).

Inhalant-related disorders include, but are not limited to, Inhalant Dependence; Inhalant Abuse; Inhalant Intoxication; Inhalant Intoxication Delirium; Inhalant-Induced Psychotic Disorder, with delusions; Inhalant-Induced Psychotic Disorder with hallucinations; Inhalant-Induced Anxiety Disorder; Inhalant-Related Disorder not otherwise specified (NOS); and Inhalant Intoxication.

Opioid-related disorders include, but are not limited to, Opioid Dependence, Opioid Abuse, Opioid Intoxication, Opioid Intoxication Delirium, Opioid-Induced Psychotic Disorder, with delusions, Opioid-Induced Psychotic Disorder with hallucinations, Opioid-Induced Anxiety Disorder, Opioid-Related Disorder not otherwise specified (NOS), Opioid Intoxication, and Opioid Withdrawal.

Tic disorders include, but are not limited to, Tourette's Disorder, Chronic Motor or Vocal Tic Disorder, Transient Tic Disorder, Tic Disorder not otherwise specified (NOS), Stuttering, Autistic Disorder, and Somatization Disorder.

The present invention further encompasses the treatment of at least two addictive diseases or disorders or impulse control disorders simultaneously. For example, the present invention provides for the simultaneous treatment of alcohol related disorders and weight control (see Examples).

The present invention also encompasses the use of the compounds and combination therapies of the invention in circumstances where mandatory treatment may be applicable. For example, a court may require that a subject be treated or take part in a treatment program using compounds or combination therapies of the invention as part of a mandated therapy related to alcohol abuse, excessive drinking, drug use, etc. More particularly, the invention encompasses forensic uses where a court would require a subject who has been convicted of driving under the influence to be subjected to the methods of the invention as part of a condition of bail, probation, treatment, etc.

The invention also encompasses the use of pharmaceutical compositions comprising compounds of the invention to practice the methods of the invention, the compositions comprising at least one appropriate compound and a pharmaceutically-acceptable carrier.

Other methods useful for the practice of the invention can be found, for example, in U.S. Pat. Pub. No. 2006/0173064 (Lippa et al.), U.S. Pat. No. 6,323,236 (McElroy), U.S. Pat. Pub. No. 2007/0275970, PCT application PCT/US/2008/052628 (Johnson et al.) filed Jan. 31, 2008, and PCT application PCT/US/2007/088100 (Johnson and Tiouririne), filed Dec. 19, 2007.

The pharmaceutical compositions useful for practicing the invention may be, for example, administered to deliver a dose of between 1 ng/kg/day and 100 mg/kg/day.

Pharmaceutical compositions that are useful in the methods of the invention may be administered, for example, systemically in oral solid formulations, or as ophthalmic, suppository, aerosol, topical or other similar formulations. In addition to the appropriate compounds, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an appropriate compound, or an analog, modification, or derivative thereof according to the methods of the invention.

Compounds which are identified using any of the methods described herein may be formulated and administered to a subject for treatment of the diseases disclosed herein. One of ordinary skill in the art will recognize that these methods will be useful for other diseases, disorders, and conditions as well.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, and birds including commercially relevant birds such as chickens, ducks, geese, and turkeys.

One type of administration encompassed by the methods of the invention is parenteral administration, which includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, and intrasternal injection, and kidney dialytic infusion techniques Pharmaceutical compositions that are useful in the methods of the invention may be prepared, packaged, or sold in formulations suitable for oral, rectal, vaginal, parenteral, topical, pulmonary, intranasal, inhalation, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject, or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Lactulose can also be used as a freely erodible filler and is useful when the compounds of the invention are prepared in capsule form.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl para hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

In one aspect, a preparation in the form of a syrup or elixir or for administration in the form of drops may comprise active ingredients together with a sweetener, which can be calorie-free, and which may further include methylparaben or propylparaben as antiseptics, a flavoring and a suitable color.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of a dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil in water emulsion or a water-in-oil emulsion. The oily phase may be a vegetable oil such as olive or *arachis* oil, a mineral oil such as liquid paraffin, or a combination of these. Such compositions may further comprise one or more emulsifying agents including naturally occurring gums such as gum acacia or gum tragacanth, naturally occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, and intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular)

form for reconstitution with a suitable vehicle (e.g., sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil in water or water in oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Such powders can comprise particles wherein at least 98% of the particles by weight have a diameter greater than 0.5 nanometers and at least 95% of the particles by number have a diameter less than 7 nanometers. In one embodiment, at least 95% of the particles by weight have a diameter greater than 1 nanometer and at least 90% of the particles by number have a diameter less than 6 nanometers. Dry powder compositions can include include a solid fine powder diluent such as sugar and are conveniently provided in a unit dose form.

Low boiling propellants generally include liquid propellants having a boiling point of below 65° F. at atmospheric pressure. Generally, the propellant may constitute about 50% to about 99.9% (w/w) of the composition, and the active ingredient may constitute about 0.1% to about 20% (w/w) of the composition. The propellant may further comprise additional ingredients such as a liquid non-ionic or solid anionic surfactant or a solid diluent (including those having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration may have have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to about 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as about 0.1% (w/w) and as much as about 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, comprise about 0.1% to about 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or atomized formulations, when dispersed, can have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1% to 1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

A pharmaceutical composition of the invention may be prepared, packaged, or sold in a formulation suitable for intramucosal administration. The present invention provides for intramucosal administration of compounds to allow passage or absorption of the compounds across mucosa. Such type of administration is useful for absorption orally (gingival, sublingual, buccal, etc.), rectally, vaginally, pulmonary, nasally, etc.

In some aspects, sublingual administration has an advantage for active ingredients which in some cases, when given orally, are subject to a substantial first pass metabolism and enzymatic degradation through the liver, resulting in rapid metabolization and a loss of therapeutic activity related to the activity of the liver enzymes that convert the molecule into inactive metabolites, or the activity of which is decreased because of this bioconversion.

In some cases, a sublingual route of administration is capable of producing a rapid onset of action due to the considerable permeability and vascularization of the buccal mucosa. Moreover, sublingual administration can also allow the administration of active ingredients which are not normally absorbed at the level of the stomach mucosa or digestive mucosa after oral administration, or alternatively which are partially or completely degraded in acidic medium after ingestion of, for example, a tablet.

Sublingual tablet preparation techniques known from the prior art are usually prepared by direct compression of a mixture of powders comprising the active ingredient and excipients for compression, such as diluents, binders, disintegrating agents and adjuvants. In an alternative method of preparation, the active ingredient and the compression excipients can be dry- or wet-granulated beforehand. In one aspect, the active ingredient is distributed throughout the mass of the tablet. WO 00/16750 describes a tablet for sublingual use that disintegrates rapidly and comprises an ordered mixture in which the active ingredient is in the form of microparticles which adhere to the surface of water-soluble particles that are substantially greater in size, constituting a support for the active microparticles, the composition also comprising a mucoadhesive agent. WO 00/57858 describes a tablet for sublingual use, comprising an active ingredient combined with an effervescent system intended to promote absorption, and also a pH-modifier.

The compounds of the invention can be prepared in a formulation or pharmaceutical composition appropriate for administration that allows or enhances absorption across mucosa. Mucosal absorption enhancers include, but are not limited to, a bile salt, fatty acid, surfactant, or alcohol. In specific embodiments, the permeation enhancer can be sodium cholate, sodium dodecyl sulphate, sodium deoxycholate, taurodeoxycholate, sodium glycocholate, dimethylsulfoxide or ethanol. In a further embodiment, a compound of the invention can be formulated with a mucosal penetration enhancer to facilitate delivery of the compound. The formulation can also be prepared with pH optimized for solubility, drug stability, and absorption through mucosa such as nasal mucosa, oral mucosa, vaginal mucosa, respiratory, and intestinal mucosa.

To further enhance mucosal delivery of pharmaceutical agents within the invention, formulations comprising the active agent may also contain a hydrophilic low molecular weight compound as a base or excipient. Such hydrophilic low molecular weight compounds provide a passage medium through which a water-soluble active agent, such as a physiologically active peptide or protein, may diffuse through the base to the body surface where the active agent is absorbed. The hydrophilic low molecular weight compound optionally absorbs moisture from the mucosa or the administration atmosphere and dissolves the water-soluble active peptide. The molecular weight of the hydrophilic low molecular weight compound is generally not more than 10000 and in one embodiment not more than 3000. Exemplary hydrophilic low molecular weight compounds include polyol compounds, such as oligo-, di- and monosaccharides such as sucrose, mannitol, lactose, L-arabinose, D-erythrose, D-ribose, D-xylose, D-mannose, D-galactose, lactulose, cellobiose, gentibiose, glycerin, and polyethylene glycol. Other examples of hydrophilic low molecular weight compounds useful as carriers within the invention include N-methylpyrrolidone, and alcohols (e.g., oligovinyl alcohol, ethanol, ethylene glycol, propylene glycol, etc.). These hydrophilic low molecular weight compounds can be used alone or in combination with one another or with other active or inactive components of the intranasal formulation.

When a controlled-release pharmaceutical preparation of the present invention further contains a hydrophilic base, many options are available for inclusion. Hydrophilic polymers such as a polyethylene glycol and polyvinyl pyrrolidone, sugar alcohols such as D-sorbitol and xylitol, saccharides such as sucrose, maltose, lactulose, D-fructose, dextran, and glucose, surfactants such as polyoxyethylene-hydrogenated castor oil, polyoxyethylene polyoxypropylene glycol, and polyoxyethylene sorbitan higher fatty acid esters, salts such as sodium chloride and magnesium chloride, organic acids such as citric acid and tartaric acid, amino acids such as glycine, beta-alanine, and lysine hydrochloride, and aminosaccharides such as meglumine are given as examples of the hydrophilic base. In one embodiment, polyethylene glycol, sucrose, polyvinyl pyrrolidone and polyethylene glycol can be used. One or a combination of two or more hydrophilic bases can be used in the present invention.

The present invention contemplates pulmonary, nasal, or oral administration through an inhaler. In one embodiment, delivery from an inhaler can be a metered dose.

An inhaler is a device for patient self-administration of at least one compound of the invention comprising a spray inhaler (e.g., a nasal, oral, or pulmonary spray inhaler) containing an aerosol spray formulation of at least one compound of the invention and a pharmaceutically acceptable dispersant. In one aspect, the device is metered to disperse an amount of the aerosol formulation by forming a spray that contains a dose of at least one compound of the invention effective to treat a disease or disorder encompassed by the invention. The dispersant may be a surfactant, such as, but not limited to, polyoxyethylene fatty acid esters, polyoxyethylene fatty acid alcohols, and polyoxyethylene sorbitan fatty acid esters. Phospholipid-based surfactants also may be used.

In other embodiments, the aerosol formulation is provided as a dry powder aerosol formulation in which a compound of the invention is present as a finely divided powder. The dry powder formulation can further comprise a bulking agent, such as, but not limited to, lactose, sorbitol, sucrose, and mannitol.

In another specific embodiment, the aerosol formulation is a liquid aerosol formulation further comprising a pharmaceutically acceptable diluent, such as, but not limited to, sterile water, saline, buffered saline and dextrose solution.

In further embodiments, the aerosol formulation further comprises at least one additional compound of the invention in a concentration such that the metered amount of the aerosol formulation dispersed by the device contains a dose of the additional compound in a metered amount that is effective to ameliorate the symptoms of disease or disorder disclosed herein when used in combination with at least a first or second compound of the invention.

Thus, the invention provides a self administration method for outpatient treatment of an addiction related disease or disorder such as an alcohol-related disease or disorder. Such administration may be used in a hospital, in a medical office, or outside a hospital or medical office by non-medical personnel for self administration.

Compounds of the invention will be prepared in a formulation or pharmaceutical composition appropriate for nasal administration. In a further embodiment, the compounds of the invention can be formulated with a mucosal penetration enhancer to facilitate delivery of the drug. The formulation can also be prepared with pH optimized for solubility, drug stability, absorption through nasal mucosa, and other considerations.

Capsules, blisters, and cartridges for use in an inhaler or insufflator may be formulated to contain a powder mix of the pharmaceutical compositions provided herein; a suitable powder base, such as lactose or starch; and a performance modifier, such as 1-leucine, mannitol, or magnesium stearate. The lactose may be anhydrous or in the form of the monohydrate. Other suitable excipients include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

For administration by inhalation, the compounds for use according to the methods of the invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of e.g., gelatin for use in an inhaler or insufflator may be formulated containing a powder mix of the drugs and a suitable powder base such as lactose or starch.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Typically, dosages of the compounds of the invention which may be administered to an animal, including a human, range in amount from about 1.0 µg to about 100 g per kilogram of body weight of the animal. The precise dosage administered will vary depending upon any number of factors, including but not limited to, the type of animal and type of disease state being treated, the age of the animal and the route of administration. In one embodiment, the dosage of the compound will vary from about 1 mg to about 10 g per kilogram of body weight of the animal. In another embodiment, the dosage will vary from about 10 mg to about 1 g per kilogram of body weight of the animal.

The compounds may be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

The invention also includes a kit comprising the compounds of the invention and an instructional material that describes administration of the compounds. In another embodiment, this kit comprises a (e.g., sterile) solvent suitable for dissolving or suspending the composition of the invention prior to administering the compound to the mammal.

As used herein, an "instructional material" includes a publication, a recording, a diagram, or any other medium of expression that can be used to communicate the usefulness of the compounds of the invention in the kit for effecting alleviation of the various diseases or disorders recited herein. Optionally, or alternately, the instructional material may describe one or more methods of alleviating the diseases or disorders. The instructional material of the kit of the invention may, for example, be affixed to a container that contains a compound of the invention or be shipped together with a container that contains the compounds. Alternatively, the instructional material may be shipped separately from the container with the intention that the instructional material and the compound be used cooperatively by the recipient.

Other methods and techniques useful for the practice of the invention that are not described are known in the art, for example, see International application no. PCT/US2008/064232.

Without further description, it is believed that one of ordinary skill in the art can, using the preceding description and the following illustrative examples, make and utilize the compounds of the present invention and practice the claimed methods. The following working examples, therefore, point out embodiments of the present invention, and are not to be construed as limiting in any way the remainder of the disclosure.

EXAMPLES

Methamphetamine addiction poses a serious public health problem for which there is no approved medication. Topiramate a seizure medication has shown efficacy in alcohol, and cocaine addictions. The Phase II double-blind placebo-controlled trial proof of concept study, and others disclosed below, were conducted to test the safety and efficacy of topiramate for the treatment of methamphetamine addiction.

Other methods not described herein are useful for the practice of the present invention. For example, see International Patent Application Nos. PCT/US2007/088100 (B. Johnson and N. Ait-Daoud Tiouririne), PCT/US2009/035420 (B. Johnson), and PCT/US2008/064232 (Johnson et al.), all of which are incorporated by reference herein in their entirety.

Example 1

The present application provides compositions and methods useful for single drug and combination therapies utilizing ondansetron and topiramate, in combination with the use of genetic diagnostic assays to help determine which treatments will be the best for alcohol or drug dependent subjects.

In PCT/US2009/035420 it was predicted that certain allelic types would offer the best treatment outcome with ondansetron. Based on the genotype matrix below, the present predication suggests that all the cells marked with an X will be efficacious, with XA being the very best, Y may respond somewhat, and Z will not respond or worsen.

|    | TT | TG | GG |
|----|----|----|----|
| LL | XA | X  | X  |
| LS | X  | Y  | Y  |
| SS | X  | Z  | Z  |

Therefore, alcoholics who are in the XA or X cells will have an added effect of ondansetron over and above their response to topiramate. That is, the combination of ondansetron and topiramate will be more efficacious than either alone or placebo in individuals with LL/TT, LL/TG, LL/GG, LS/TT, or SS/TT genotype. To that end, the present disclosure suggests that alcoholics in the XA, X, or Y cells will have an added effect of ondansetron over and above their response to topiramate. That is, the combination of ondansetron and topiramate will be more efficacious than either alone or placebo in individuals with LL/TT, LL/TG, LL/GG, LS/TT, LS/TG, LS/GG, or SS/TT genotype.

The present disclosure further suggests that alcoholics in the ZZ cells who receive topiramate will not have an added effect of ondansetron. That is, alcoholics with SS/TG or SS/GG genotype. The present disclosure also suggests that alcoholics in the Z or Y cells who receive topiramate would not have an added effect of ondansetron. That is, alcoholics with LS/TG, LS/GG, SS, TG, or SS/GG genotype.

New data supporting these suggestions are provided in the Examples below, show an effect of LL and also LL/TT having a superior response to ondansetron compared with placebo. The methods and results of U.S. Provisional Application No. 61/263,599 (B. Johnson), filed Nov. 23, 2009, are incorporated by reference herein.

The data further suggest that some individuals with certain polymorphisms in the glutamate system might not respond to topiramate, thereby diminishing the efficacy of the combination of ondansetron and topiramate or might experience significant side-effects from topiramate which would reduce efficacy of the COMBO because they might take a lower dose, skip doses, or not take the medication(s) altogether. For example, these polymorphisms might lie in the GluR1-GluR5 system or the GABA-A or GABA-B system.

Useful dosages and combinations include those found in PCT/US2007/088100 (B. Johnson and N. Ait-Daoud Tiouririne).

Example 2—Alcohol Dependent Individuals with the TT Vs. (TG/GG) Genotype of the 3-UTR Region May Respond Differentially to Ondansetron Vs Placebo Treatment Two hundred and seventy eight male and female alcohol dependent individuals were entered into a randomized, double-blind, placebo-controlled, 12-week clinical trial. These individuals were divided into TT vs. TG/GG) groups of the rs1042173 SNP of the 3-UTR in the serotonin transporter gene as well as ondansetron (4 mcg/kg) vs. placebo groups. The polymorphisms in 3"-UTR region of a gene may affect mRNA expression levels by altering their stability. We propose that the TT genotype of rs1042173 will be associated with lower levels of mRNA expression compared with those of the TG/GG genotype. We hypothesize that due to pre-synaptic inhibition at the serotonin autoreceptor, the net effect of reduced mRNA expression would be a relative hypo-serotonergic state that would lead to upregulated post-synaptic serotonin receptors. We, therefore, propose further that ondansetron (a serotonin-3 receptor antagonist) might exert a therapeutic effect in individuals with the TT genotype by blocking these upregulated post-synaptic receptors.

Data was transformed to its natural log to correct for skewness. Mixed model analysis of Log Drinks/Drinking day (our primary endpoint to measure severity of drinking) data showed that ondansetron is more beneficial than placebo in reducing severe drinking among individuals with TT genotype (p=0.028). Furthermore, we found that the lowest drinking was found in the TT group that received ondansetron (TT ond–Log mean=1.36±0.10 Drinks/Drinking Day). In contrast, the TT group that received placebo (TT placebo) consumed a Log mean of 1.61±0.09 Drinks/Drinking Day. There was a statistically significant difference between the TTond and TG/GG ond groups (Log mean difference=–0.33 95% CI–0.53 to –0.13, p=0.002). From the diagram (FIG. 1), it is evident that the TT placebo group's drinking was lower than either the TG/GG placebo group–Log mean=1.72±0.07 Drinks/Drinking Day or the TT/GG and group–Log mean=1.68±0.07 Drinks/Drinking Day). Furthermore, among placebo, there was no significant difference in drinking severity between the TT and TG/GG groups (Log mean difference –0.10 95% CI –0.30 to 0.10 Drinks/Drinking Day; p=0.315) (FIG. 1).

In summary, these data showed that individuals with the TT genotype who received ondansetron improved their drinking outcomes significantly (i.e., show a greater reduction in severe drinking) compared with their TG/GG counterparts. Also, those with TT genotype who received ondansetron improved their drinking outcomes significantly compared with individuals of TT genotype who got placebo. These data, provide preliminary support that ondansetron might be differentially efficacious among individuals with the TT genotype.

Example 3—Effects of 5HT3a and 5HT3b SNPs on Ondansetron Treatment Outcome

Figure 2:
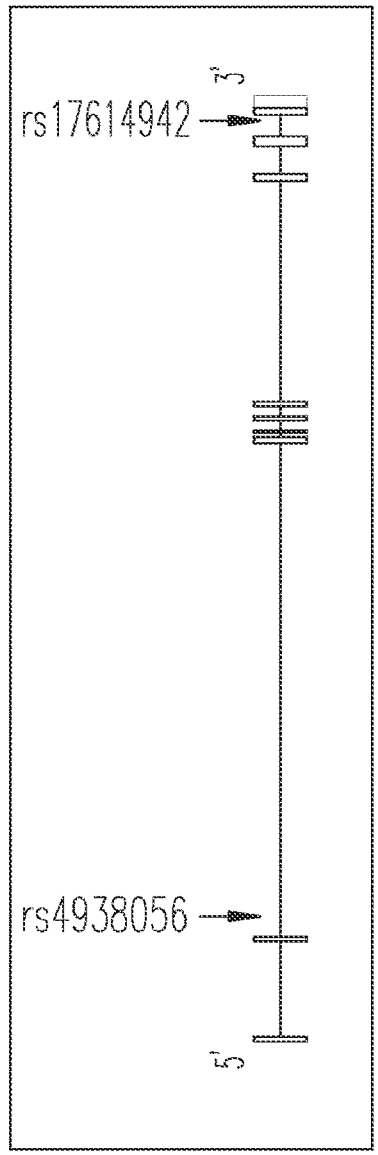
FIG. 2 shows the locations 2 SNPs in the 5HT$_3$b gene (top panel), rs4938056 and rs17614942 and 2 SNPs in the 5HT$_3$a gene (bottom panel), rs1150226 and rs1062613.
Figure 2:
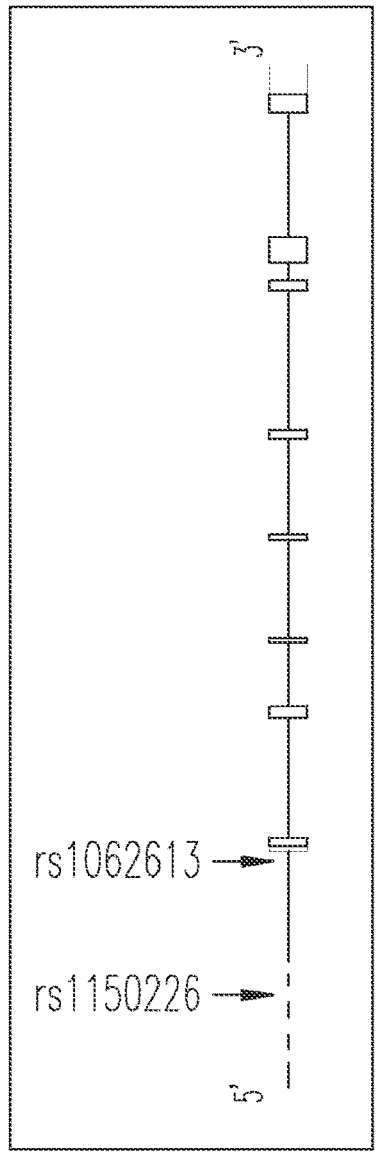

The genetic effects of SNPs within the two genes that code for the two subunits of 5HT3 receptor, on ondansetron treatment outcome were analyzed using a mixed-effect linear regression model. In total, ten SNPs in 5HT3a and nine SNPs in 5HT3b genes were analyzed in this study:
Summary of Results for 5HT3b SNP Analysis:
2 SNPs in the 5HT3b gene (rs4938056 and rs17614942) interacted significantly with ondansetron treatment:
  1. rs4938056*treatment: P=0.024; F=5.11 (Both treatment and genotype main effects were not significant in the population studied)
  2. rs17614942*treatment: P=0.01; F=6.62 (In the population studied, the main effect of treatment was significant at P=0.019; the genotype main effect was not significant).
The locations of these 2 SNPs within 5HT3b gene are shown in FIG. 2.
Ondansetron reduced DDD differentially in the 2 genotypic groups of rs4938056: T-carriers had a reduction of DDD by 1.30 sd compared with CC subjects (P=0.013; 95% CI=–2.32 to –0.27).

The reduction of DDD by ondansetron was also significantly different in subjects carrying AC/AA and CC genotypes for rs17614942: AC/AA treated with ondansetron had a 1.97 sd reduction in DDD compared to CC subjects.

Within the AC/AA group of rs17614942, ondansetron reduced DDD by 2.41 sd compared to the placebo (P=0.008; 95% CI=−4.21 to −0.62)

However, within the cohort studied for 5HT3b associations, ondansetron had a significant effect on reducing DDD, regardless of the genotypes of rs17614942 (Estimated mean DDD difference for OND vs. placebo=−1.15 (P=0.019; 95% CI=−2.11 to −0.19)).

Figure 3:
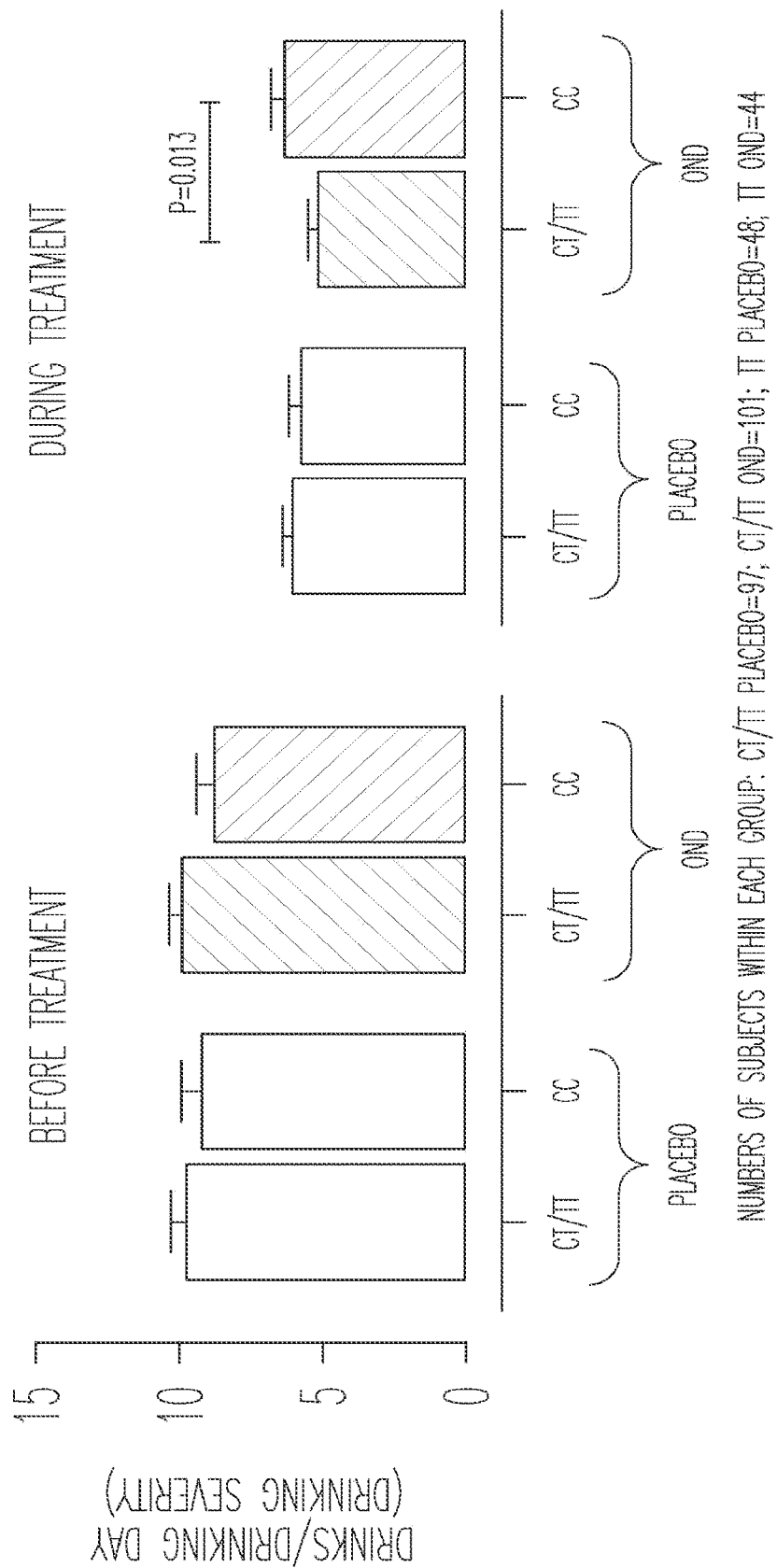
FIG. 3 shows the DDD in genotypic group rs4938056.
Figure 4:
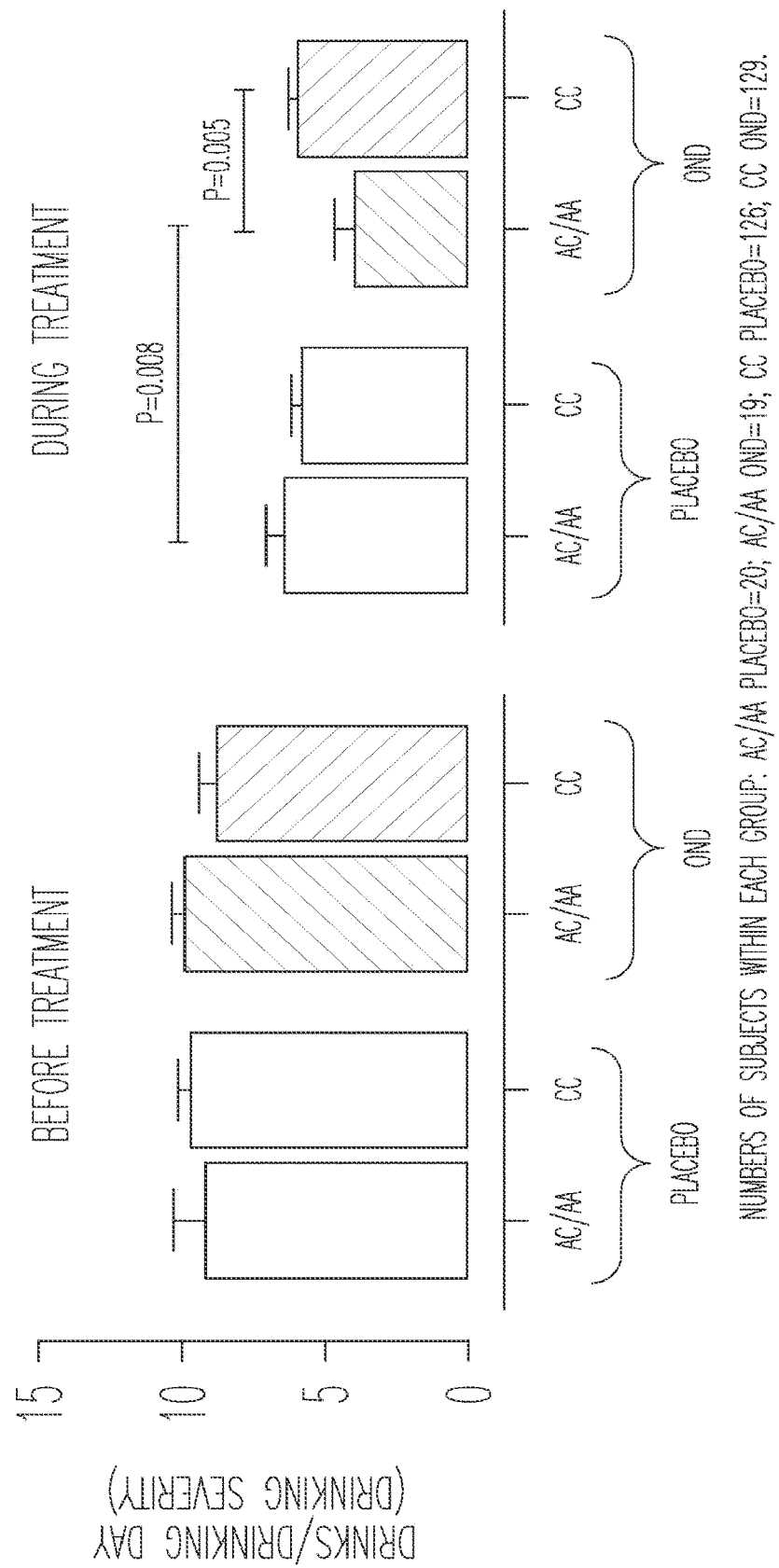
FIG. 4 shows the DDD in genotypic group rs17614942.
Figure 5:
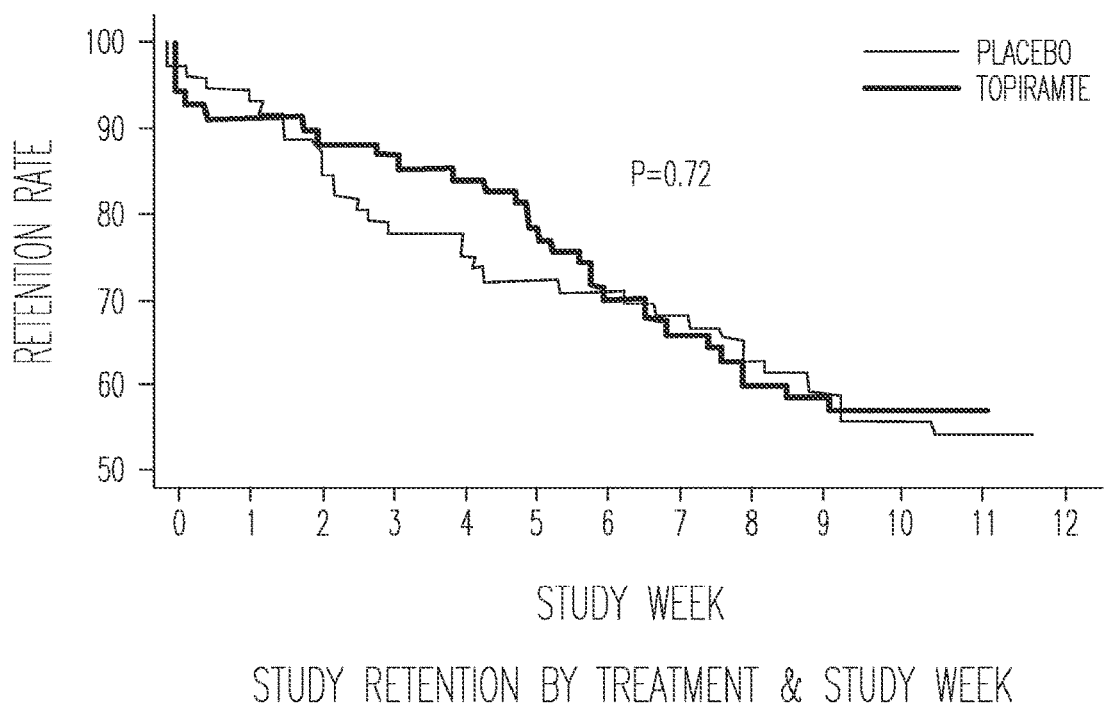
FIG. 5 shows the retention rate versus study week in VA/NIDA Study #1025-Topiramate for the Treatment of Methamphetamine Dependence.
Figure 6:
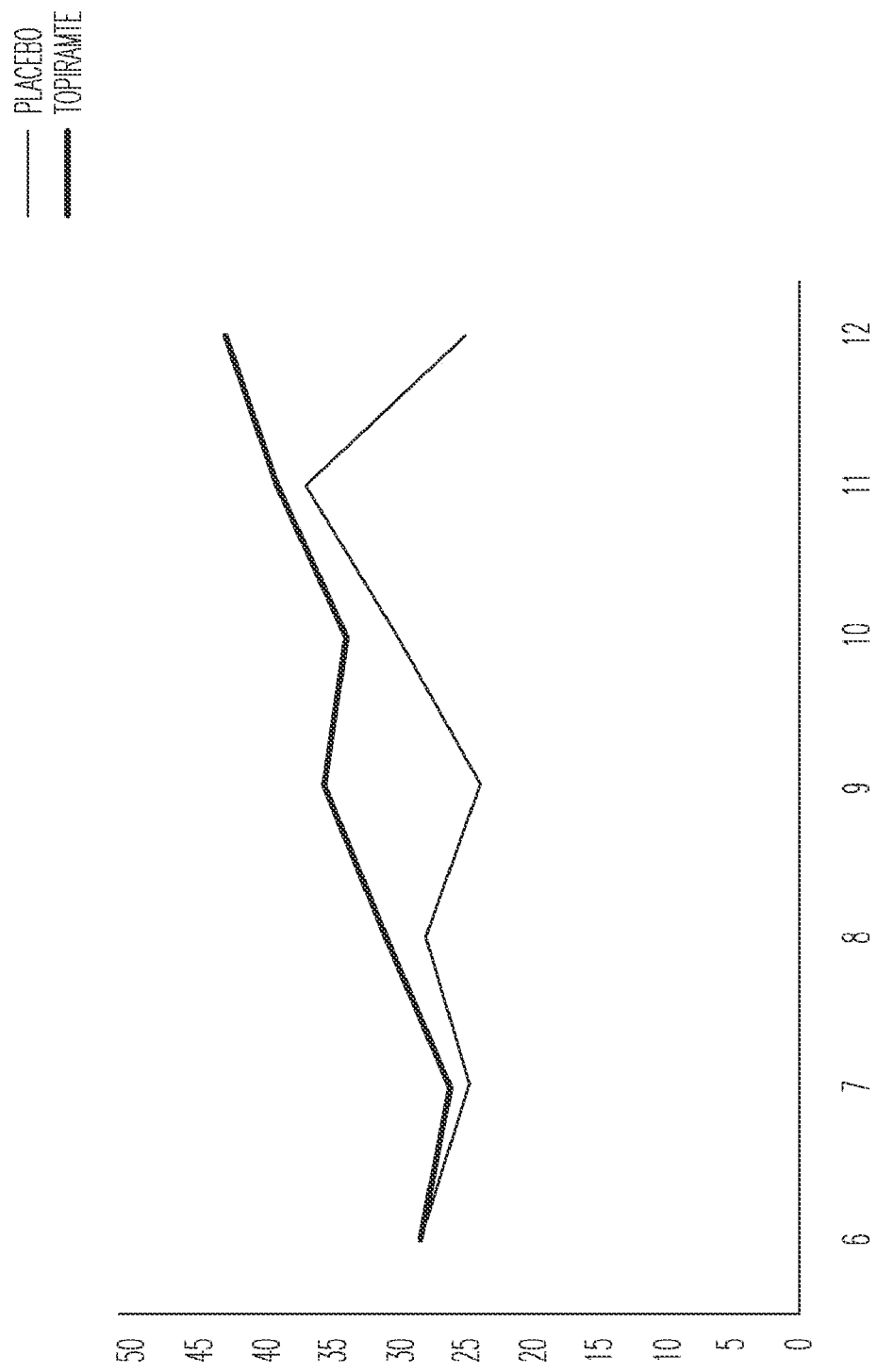
FIG. 6 shows the percentage of subjects with a negative methamphetamine use weeks in weeks 6-12 (all urine drug screens for methamphetamine are negative).
Figure 7:
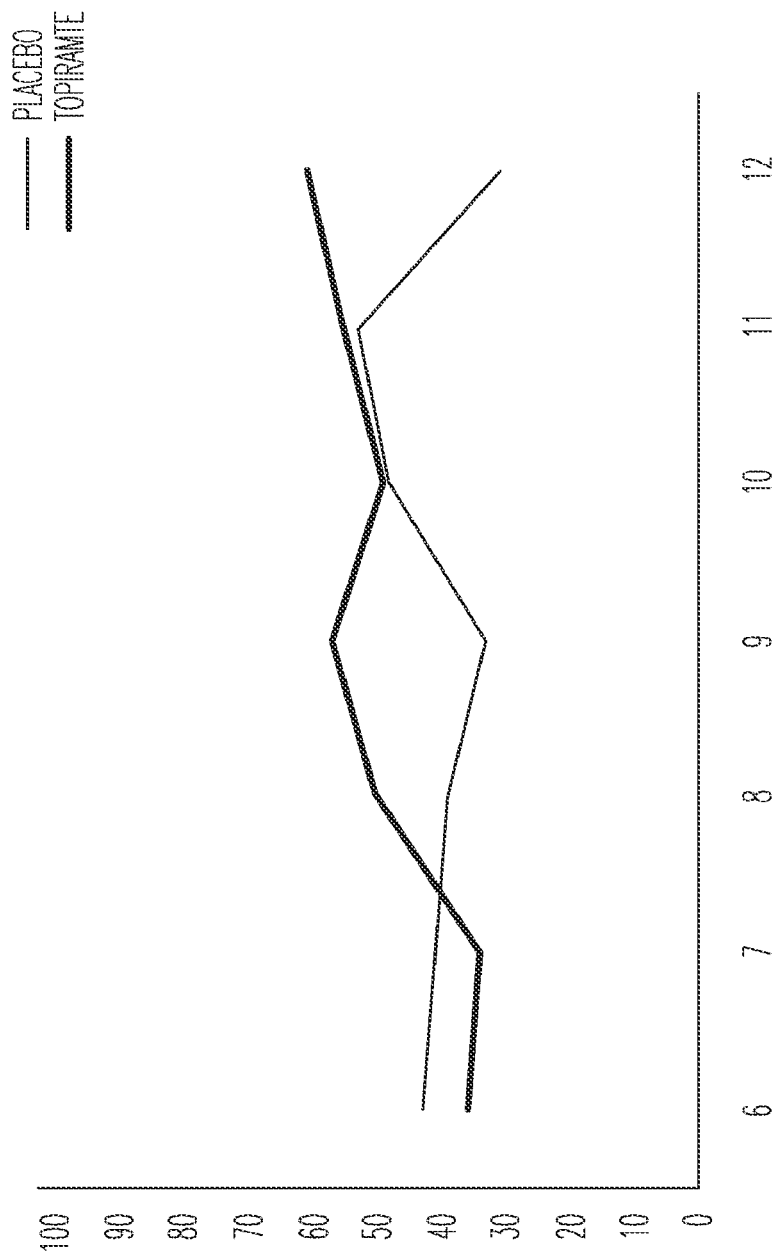
FIG. 7 shows the percentage of subjects with a negative methamphetamine use week in weeks 6-12 for light methamphetamine users only (<=18 days use) in VA/NIDA Study #1025-Topiramate for the Treatment of Methamphetamine Dependence.
Figure 8:
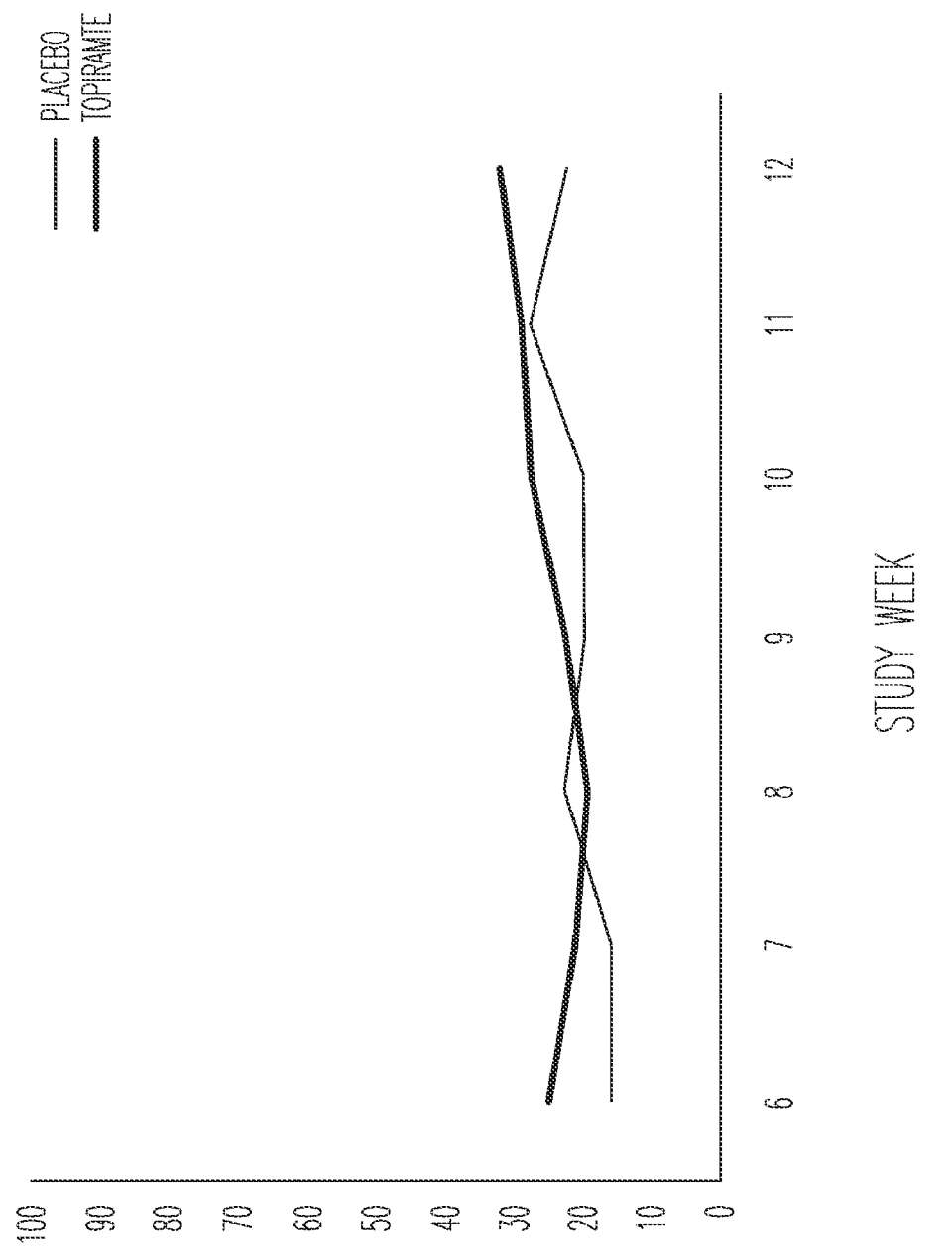
FIG. 8 shows the percentage of subjects with a negative methamphetamine use week in weeks 6-12 for heavy methamphetamine users only (>18 days use))VA/NIDA Study #1025-Topiramate for the Treatment of Methamphetamine Dependence.
Figure 9:
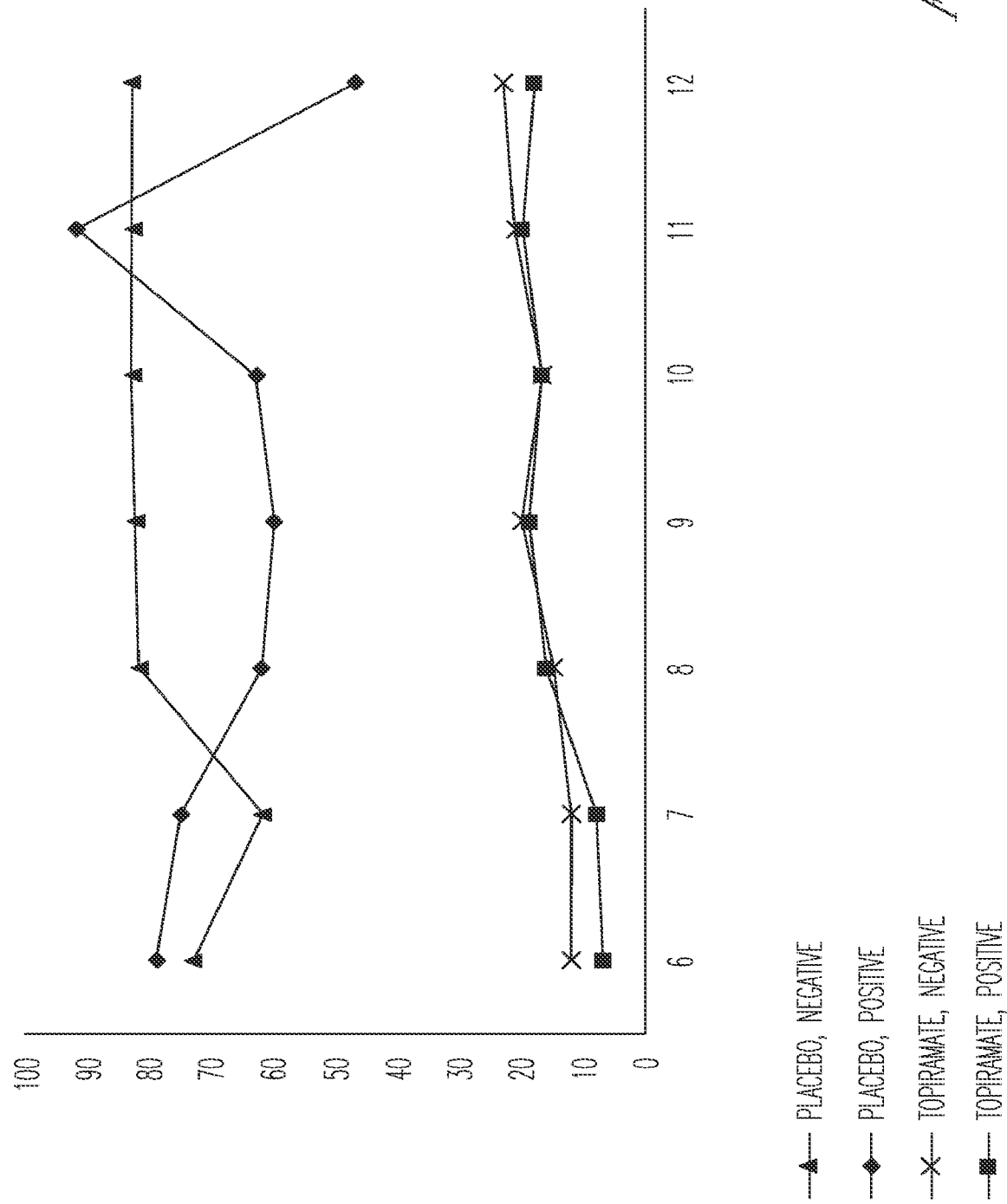
FIG. 9 shows the Study Week; Treatment group and last urine result prior to randomization breakdown for the percentage of subjects with a negative methamphetamine use week in weeks 6-12 in VA/NIDA Study #1025—Topiramate for the Treatment of Methamphetamine Dependence.

FIGS. 3 and 4 shows the DDD in different genotypic groups of rs4938056 and rs17614942, respectively.

Summary of Results for 5HT3b SNPs+5HTTLPR Analysis:

rs4938056+5HTTLPR

The combined genotypes had a slightly greater effect than the effects of rs4938056 genotypes alone.

Ondansetron reduced DDD by 1.82 sd in subjects carrying LL+CT/TT genotypes compared to subjects who do not carry this genotype combination (P=0.001; 95% CI=−2.88 to −0.77).

Within LL+CT/TT group, ondansetron reduced DDD significantly better than placebo (Least square Mean difference=1.74 sd; P=0.011; 95% CI=−3.08 to −0.04)

rs17614942+5HTTLPR

When rs17614942 genotypes were combined with 5HTTLPR genotypes of serotonin transporter gene, ondansetron showed the highest effect on reducing DDD. Ondansetron reduced DDD by 3.33 sd in subjects carrying LL+AC/AA genotypes compared to subjects who do not carry this genotype combination (P=0.001; 95% CI=−5.34 to −1.32).

Within LL+AC/AA group, ondansetron reduced DDD significantly better than placebo (Least square Mean difference=3.6 sd; P=0.013; 95% CI=−6.42 to −0.77)

Summary of Results for 5HT3a SNP Analysis:

SNP rs1062613 in 5HT3a gene showed a marginally significant interaction with treatment in reducing DDD: rs1062613*treatment: P=0.047; F=3.93 (Both treatment and genotype main effects were not significant in the population studied)

Ondansetron reduced DDD differentially in the 2 genotypic groups of rs1062613: C-carriers had a reduction of DDD by 1.17 sd compared with TT subjects (P=0.016; 95% CI=−2.12 to −0.22).

The SNP rs1150226 in 5HT3a also showed a significant association with DDD but its interaction with treatment showed only a trend (P=0.065; F=3.42).

Ondansetron reduced DDD by 1.74 sd in AG/AA subjects of rs1150226, compared to GG subjects (P=0.006; 95% CI=−2.97 to −0.5).

Within the AG/AA group of rs1150226, ondansetron reduced DDD by 1.57 sd compared to the placebo (P=0.050; 95% CI=−3.14 to −0.001)

None of the above 5HT3a SNPs were significant when combined with 5-HTTLPR genotypes.

Example 4—Topiramate for the Treatment of Methamphetamine Addiction

Methods—The study was conducted at 8 sites, 140 subjects consented, screened for study eligibility and met DSM-IV criteria for methamphetamine dependence. Subjects were randomized to topiramate or placebo at 50 mg, escalating to 200 mg topiramate daily over weeks 1-5, and 200 mg daily over weeks 6-12. The primary outcome measure was abstinence from methamphetamine during study weeks 6 through 12. Methamphetamine use was determined using qualitative urine testing at a central laboratory. The primary outcome was analyzed using a Generalized Estimating Equation (GEE) model during weeks 6 through 12. Secondary outcomes included use reduction compared to baseline, relapse rate for subjects with negative urine at randomization, and craving. Blood samples were collected for genetic markers to examine the effects of topiramate on gene expression and to correlate genetic subtypes with response to treatment. RNA samples were collected from whole blood for 50 topiramate- and 49 placebo-treated individuals at baseline and weeks 8 and 12. Genome-wide expression profiles between positive and negative responders for Weeks 8 and 12 from placebo- and topiramate-treated groups were compared.

Results-(see FIGS. 5-9) 338 adults ages 18-45 were screened in order to enroll 140 subjects at eight sites. Of these, 77 (55%) subjects completed the 12 weeks of treatment and at least one visit in week 13. For weeks 6-12 partial urinalysis data was available on 105 subjects, with 66 subjects providing samples during week 12. The mean age was 38.4 years and 37.5 years in the topiramate group and placebo group respectively, males comprised 59.4% of the sample in the topiramate group, compared to (67.6%) taking placebo. Topiramate was generally well-tolerated and safe.

For the primary outcome variable, no significant treatment effect for topiramate was seen. In general, the results were similar for other secondary outcomes derived directly from the urinalysis data. Exploratory analyses of the data, however, indicated that subjects (n=35) whose baseline use was <18 days out of the previous 30, or who had negative urine prior to randomization (n=26) had a significant treatment effect on topiramate (p=0.03 and 0.02 respectively).

At the single-gene level, 1848, 959, 675, and 741 differentially expressed genes were identified, respectively, for Week 8 topiramate, Week 8 placebo, Week 12 topiramate, and Week 12 placebo groups. Among them, some genes involved in nervous system development, metabolism or other fundamental functions were only shared by Weeks 8 and 12 topiramate groups: PRKACB, USP38, BUB3, GPR183, GNG2, PTPRN2, USP16, ZNF443, ACAA2, SLC30A6, UBE2A were all up-regulated and that CAMTA2, SLCO3A1, TIMP2, SLC19A1, ADM, TLR5, and NTNG2 were down-regulated, in the topiramate-treated groups. Pathway analysis revealed that 24 enriched pathways were shared between Weeks 8 and 12 topiramate groups. Six biological pathways were detected by at least two pathway discovery tools; four of these pathways, long-term potentiation, Fc epsilon RI signaling pathway, MAPK signaling pathway and GnRH signaling pathway, have been previously reported to play roles in drug addiction.

Conclusions—Example 4—Limitations of the study were the high attrition rate by the end of the study and underestimation of the minimum effective dose. The majority of subjects also failed to reach a daily dose of at least 150 mg of topiramate, and only six subjects reported taking 200 mg daily. Topiramate significantly modulated the expression levels of genes involved in several biological processes underlying addiction behavior, but insufficient numbers of subjects at week 12 prevent definitive correlations between treatment with topiramate and subsequent genetic modulation. Despite the failure of the per protocol outcome variables a subset of "lighter" methamphetamine users were identified as positive responders to treatment. Future investigations with topiramate should concentrate on reaching a dose of at least 150 mg/day and on identifying patients who are amenable to initiating abstinence and investigating topiramate's role as a relapse prevention medication.

Example 5

1. RS1062613 in 5-HT3A
a. RS1062613 SNP

TABLE 1

Example 5: ANOVA of Drinks per Drinking Days

| Variable | Drinks per Drinking Days | |
|---|---|---|
| | F-Value | P-Value |
| RS1062613 (TT, TC/CC) | 1.64 | 0.201 |
| Treatment | 0.67 | 0.412 |
| RS1062613*Treatment | 3.23 | 0.072 |

TABLE 2

Example 5: Least Squares Mean

| Effect | Estimated Mean | Standard Error |
|---|---|---|
| TC/CC | 5.58 | 0.29 |
| TT | 6.02 | 0.25 |
| Placebo | 5.94 | 0.27 |
| OND | 5.66 | 0.27 |
| TC/CC: Placebo | 6.03 | 0.39 |
| OND | 5.13 | 0.40 |
| TT: Placebo | 5.85 | 0.34 |
| OND | 6.19 | 0.33 |

TABLE 3

Example 5: Least Squares Mean Difference between Treatment and Placebo and Its 95% Confidence Intervals

| Effect | Estimated Mean Difference | Lower 95% C.I. | Upper 95% C.I. | P-Value |
|---|---|---|---|---|
| Among OND: | | | | |
| TC/CC vs. TT | −1.06 | −2.01 | −0.11 | 0.029 |
| Among TC/CC: | | | | |
| OND vs. Placebo | −0.90 | −1.94 | 0.14 | 0.089 |

TABLE 4

Example 5: Frequency of RS1062613

| RS1062613 | Frequency |
|---|---|
| CC | 13 (4.4%) |
| TC | 107 (36.2%) |
| TT | 176 (59.5%) | b. 5-HTTLPR and RS1062613

TABLE 1

Part b.- Example 5: ANOVA of Drinks per Drinking Days

| Variable | Drinks per Drinking Days | |
|---|---|---|
| | F-Value | P-Value |
| RS1062613 (TT, TC/CC) | 1.75 | 0.186 |
| Treatment | 2.03 | 0.154 |
| RS1062613*Treatment | 3.02 | 0.082 |
| 5-HTTLPR (LL, LS/SS) | 2.94 | 0.086 |
| 5-HTTLPR*Treatment | 4.79 | 0.029 |

TABLE 2

Part b. Example 5: Least Squares Mean

| Effect | Estimated Mean | Standard Error |
|---|---|---|
| TC/CC | 5.53 | 0.30 |
| TT | 5.98 | 0.26 |
| Placebo | 6.01 | 0.29 |
| OND | 5.50 | 0.28 |
| TC/CC: Placebo | 6.08 | 0.40 |
| OND | 4.98 | 0.40 |
| TT: Placebo | 5.94 | 0.36 |
| OND | 6.02 | 0.33 |
| LS/SS | 6.06 | 0.25 |
| LL | 5.45 | 0.31 |
| LS/SS: Placebo | 5.93 | 0.32 |
| OND | 6.19 | 0.33 |
| LL: Placebo | 6.09 | 0.45 |
| OND | 4.80 | 0.41 |

TABLE 3

Part b, Example 5: Least Squares Mean Difference between Treatment and Placebo and Its 95% Confidence Intervals

| Effect | Estimated Mean Difference | Lower 95% C.I. | Upper 95% C.I. | P-Value |
|---|---|---|---|---|
| Among OND: LL vs. LS/SS | −1.39 | −2.36 | −0.42 | 0.005 |
| Among LL: OND vs. Placebo | −1.29 | −2.43 | −0.15 | 0.027 |
| Among OND: TC/CC vs. TT | −1.05 | −1.99 | −0.10 | 0.030 |
| Among TC/CC: OND vs. Placebo | −1.10 | −2.15 | −0.06 | 0.039 |

2. RS1150226 in 5-HT3A
a. RS1150226

TABLE 1

Section 2, Part a, Example 5: ANOVA of Drinks per Drinking Days

| Variable | Drinks per Drinking Days | |
|---|---|---|
| | F-Value | P-Value |
| RS1150226 (GG, AG/AA) | 3.17 | 0.075 |
| Treatment | 1.93 | 0.165 |
| RS1150226*Treatment | 2.35 | 0.126 |

TABLE 2

Section 2, Part a, Example 5: Least Squares Mean

| Effect | Estimated Mean | Standard Error |
|---|---|---|
| AG/AA | 5.22 | 0.41 |
| GG | 6.01 | 0.23 |
| Placebo | 5.92 | 0.33 |
| OND | 5.31 | 0.33 |
| AG/AA: Placebo | 5.86 | 0.58 |
| OND | 4.58 | 0.58 |
| GG: Placebo | 5.98 | 0.30 |
| OND | 6.04 | 0.29 |

TABLE 3

Section 2, Part a: Least Squares Mean Difference between Treatment and Placebo and Its 95% Confidence Intervals

| Effect | Estimated Mean Difference | Lower 95% C.I. | Upper 95% C.I. | P-Value |
|---|---|---|---|---|
| Among OND: | | | | |
| AG/AA vs. GG | −1.47 | −2.69 | −0.24 | 0.019 |
| AG/AA vs. GG | −0.79 | −1.66 | 0.08 | 0.075 |

TABLE 4

Section 2, Part a, Example 5: Frequency of RS1150226

| RS1150226 | Frequency |
|---|---|
| AA | 5 (1.7%) |
| AG | 47 (15.9%) |
| GG | 243 (82.4%) | b. 5-HTTLPR and RS1150226

TABLE 1

Section 2, Part b, Example 5: ANOVA of Drinks per Drinking Days

| | Drinks per Drinking Days | |
|---|---|---|
| Variable | F-Value | P-Value |
| RS1150226 (GG, AG/AA) | 2.48 | 0.116 |
| Treatment | 2.79 | 0.095 |
| RS1150226*Treatment | 1.54 | 0.214 |
| 5-HTTLPR (LL, LS/SS) | 2.34 | 0.126 |
| 5-HTTLPR*Treatment | 4.02 | 0.045 |

TABLE 2

Section 2, Part b, Example 5: Least Squares Mean

| Effect | Estimated Mean | Standard Error |
|---|---|---|
| AG/AA | 5.25 | 0.41 |
| GG | 5.95 | 0.24 |
| Placebo | 5.97 | 0.34 |
| OND | 5.23 | 0.33 |
| AG/AA: Placebo | 5.90 | 0.58 |
| OND | 4.60 | 0.57 |
| GG: Placebo | 6.05 | 0.31 |
| OND | 5.85 | 0.30 |
| LS/SS | 5.87 | 0.29 |
| LL | 5.33 | 0.33 |
| LS/SS: Placebo | 5.89 | 0.37 |

TABLE 2-continued

Section 2, Part b, Example 5: Least Squares Mean

| Effect | Estimated Mean | Standard Error |
|---|---|---|
| OND | 5.86 | 0.40 |
| LL: Placebo | 6.06 | 0.48 |
| OND | 4.59 | 0.43 |

TABLE 3

Section 2, Part b, Example 5: Least Squares Mean Difference between Treatment and Placebo and Its 95% Confidence Intervals

| Effect | Estimated Mean Difference | Lower 95% C.I. | Upper 95% C.I. | P-Value |
|---|---|---|---|---|
| Among OND: LL vs. LS/SS | −1.27 | −2.25 | −0.29 | 0.011 |
| Among LL: OND vs. Placebo | −1.47 | −2.70 | −0.23 | 0.020 |
| Among OND: AG/AA vs. GG | −1.25 | −2.48 | −0.01 | 0.047 |

3. RS17614942 in 5-HT3B a. RS17614942

TABLE 1

Section 3, Part a, Example 5: ANOVA of Drinks per Drinking Days

| | Drinks per Drinking Days | |
|---|---|---|
| Variable | F-Value | P-Value |
| RS17614942 (CC, AC/AA) | 1.09 | 0.297 |
| Treatment | 3.86 | 0.049 |
| RS17614942*Treatment | 4.85 | 0.028 |

TABLE 2

Section 3, Part a, Example 5: Least Squares Mean

| Effect | Estimated Mean | Standard Error |
|---|---|---|
| AC/AA | 5.42 | 0.47 |
| CC | 5.94 | 0.22 |
| Placebo | 6.16 | 0.37 |
| OND | 5.20 | 0.37 |
| AC/AA: Placebo | 6.44 | 0.66 |
| OND | 4.40 | 0.66 |
| CC: Placebo | 5.88 | 0.29 |
| OND | 6.00 | 0.29 |

TABLE 3

Section 3, Part a, Example 5: Least Squares Mean Difference between Treatment and Placebo and Its 95% Confidence Intervals

| Effect | Estimated Mean Difference | Lower 95% C.I. | Upper 95% C.I. | P-Value |
|---|---|---|---|---|
| Among OND: AC/AA vs. CC | −1.60 | −3.00 | −0.23 | 0.022 |
| Among AC/AA: | | | | |
| OND vs. Placebo | −2.04 | −3.83 | −0.26 | 0.025 |
| OND vs. Placebo | −0.96 | −1.92 | −0.002 | 0.050 |

TABLE 4

Section 3, Part a, Example 5: Frequency of RS17614942

| RS17614942 | Frequency |
|---|---|
| AA | 2 (0.7%) |
| AC | 38 (12.9%) |
| CC | 255 (86.4%) | b. RS17614942 and 5-HTTLPR

TABLE 1

Section 3, Part b, Example 5: ANOVA of Drinks per Drinking Days

| | Drinks per Drinking Days | |
|---|---|---|
| Variable | F-Value | P-Value |
| RS17614942 (CC, AC/AA) | 0.83 | 0.362 |
| 5-HTTLPR (LL, LS/SS) | 2.77 | 0.096 |
| Treatment | 5.17 | 0.023 |
| RS17614942*Treatment | 4.23 | 0.040 |
| 5-HTTLPR*Treatment | 4.23 | 0.040 |

TABLE 2

Section 3, Part b, Example 5: Least Squares Mean

| Effect | Estimated Mean | Standard Error |
|---|---|---|
| AC/AA | 5.43 | 0.47 |
| CC | 5.88 | 0.23 |
| Placebo | 6.22 | 0.38 |
| OND | 5.09 | 0.37 |
| AC/AA: Placebo | 6.50 | 0.65 |
| OND | 4.37 | 0.65 |
| CC: Placebo | 5.94 | 0.31 |
| OND | 5.82 | 0.29 |
| LS/SS | 5.95 | 0.31 |
| LL | 5.36 | 0.35 |
| LS/SS: Placebo | 6.15 | 0.41 |
| OND | 5.76 | 0.42 |
| LL: Placebo | 6.29 | 0.50 |
| OND | 4.43 | 0.46 |

TABLE 3

Section 3, Part b, Example 5: Least Squares Mean Difference between Treatment and Placebo and Its 95% Confidence Intervals

| Effect | Estimated Mean Difference | Lower 95% C.I. | Upper 95% C.I. | P-Value |
|---|---|---|---|---|
| OND vs. Placebo Among OND: | −1.13 | −2.10 | −0.15 | 0.023 |
| LL vs. LS/SS Among LL: | −1.33 | −2.30 | −0.36 | 0.008 |
| OND vs. Placebo Among OND: | −1.86 | −3.16 | −0.56 | 0.005 |
| AC/AA vs. CC Among AC/AA: | −1.45 | −2.81 | −0.09 | 0.037 |
| OND vs. Placebo | −2.13 | −3.91 | −0.35 | 0.019 |

4. RS4938056 in 5-HT3B a. RS4938056

TABLE 1

Section 4, Part a, Example 5: ANOVA of Drinks per Drinking Days

| | Drinks per Drinking Days | |
|---|---|---|
| Variable | F-Value | P-Value |
| RS4938056 (TT/TC, CC) | 1.51 | 0.219 |
| Treatment | 0.23 | 0.628 |
| RS4938056*Treatment | 4.66 | 0.031 |

TABLE 2

Section 4, Part a, Example 5: Least Squares Mean

| Effect | Estimated Mean | Standard Error |
|---|---|---|
| CC | 6.19 | 0.33 |
| CT/TT | 5.73 | 0.24 |
| Placebo | 5.87 | 0.29 |
| OND | 6.05 | 0.29 |
| CC: Placebo | 5.71 | 0.44 |
| OND | 6.67 | 0.46 |
| CT/TT: Placebo | 6.03 | 0.32 |
| OND | 5.43 | 0.31 |

TABLE 3

Section 4, Part a, Example 5: Least Squares Mean Difference between Treatment and Placebo and Its 95% Confidence Intervals

| Effect | Estimated Mean Difference | Lower 95% C.I. | Upper 95% C.I. | P-Value |
|---|---|---|---|---|
| Among OND: | | | | |
| CT/TT vs. CC | −1.24 | −2.27 | −0.21 | 0.018 |

TABLE 4

Section 4, Part a, Example 5: Frequency of RS4938056

| RS4938056 | Frequency |
|---|---|
| TT | 68 (23.4%) |
| CT | 131 (45.0%) |
| CC | 92 (31.6%) | b. RS4938056 and 5-HTTLPR

TABLE 1

Section 4, Part b, Example 5: ANOVA of Drinks per Drinking Days

| | Drinks per Drinking Days | |
|---|---|---|
| Variable | F-Value | P-Value |
| RS4938056 (CC, CT/TT) | 1.17 | 0.279 |
| 5-HTTLPR (LL, LS/SS) | 2.80 | 0.095 |
| Treatment | 0.04 | 0.836 |
| RS4938056*Treatment | 4.10 | 0.043 |
| 5-HTTLPR*Treatment | 4.61 | 0.032 |

TABLE 2

Section 4, Part b, Example 5: Least Squares Mean

| Effect | Estimated Mean | Standard Error |
|---|---|---|
| CC | 6.10 | 0.34 |
| CT/TT | 5.70 | 0.25 |
| Placebo | 5.94 | 0.30 |
| OND | 5.86 | 0.30 |
| CC: Placebo | 5.77 | 0.45 |
| OND | 6.42 | 0.46 |
| CT/TT: Placebo | 6.10 | 0.33 |
| OND | 5.29 | 0.31 |
| LS/SS | 6.20 | 0.25 |
| LL | 5.60 | 0.33 |
| LS/SS: Placebo | 5.85 | 0.32 |
| OND | 6.54 | 0.34 |
| LL: Placebo | 6.02 | 0.46 |
| OND | 5.18 | 0.43 |

TABLE 3

Section 4, Part b, Example 5: Least Squares Mean Difference between Treatment and Placebo and Its 95% Confidence Intervals

| Effect | Estimated Mean Difference | Lower 95% C.I. | Upper 95% C.I. | P-Value |
|---|---|---|---|---|
| Among OND: | | | | |
| LL vs. LS/SS | −1.37 | −2.34 | −0.39 | 0.006 |
| Among OND: | | | | |
| CT/TT vs. CC | −1.13 | −2.15 | −0.11 | 0.031 |
| Among CT/TT | | | | |
| OND vs. Placebo | −0.81 | −1.63 | 0.01 | 0.054 |

Simplified Model

TABLE 1

Section 4, Part c, Example 5: ANOVA of Drinks per Drinking Days

| | Drinks per Drinking Days | |
|---|---|---|
| Variable | F-Value | P-Value |
| Comb. Genotype (LL + CT/TT, Others) | 2.97 | 0.085 |
| Treatment | 2.28 | 0.132 |
| Comb. Genotype*Treatment | 5.87 | 0.016 |

TABLE 2

Section 4, Part c, Example 5: Least Squares Mean

| Effect | Estimated Mean | Standard Error |
|---|---|---|
| LL + CT/TT | 5.39 | 0.36 |
| Others | 6.07 | 0.23 |
| Placebo | 6.02 | 0.31 |
| OND | 5.43 | 0.30 |
| LL + CT/TT: Placebo | 6.16 | 0.52 |
| OND | 4.61 | 0.47 |
| Others: Placebo | 5.89 | 0.30 |
| OND | 6.25 | 0.31 |

TABLE 3

Section 4, Part c, Example 5: Least Squares Mean Difference between Treatment and Placebo and Its 95% Confidence Intervals

| Effect | Estimated Mean Difference | Lower 95% C.I. | Upper 95% C.I. | P-Value |
|---|---|---|---|---|
| Among OND: | | | | |
| LL + CT/TT vs. Others | −1.64 | −2.69 | −0.58 | 0.002 |
| LL + CT/TT | | | | |
| OND vs. Placebo | −1.55 | −2.89 | −0.20 | 0.024 |

TABLE 4

Section 4, Part c, Example 5: Frequency of Combined Genotype and Treatment

| | Combined Genotype | |
|---|---|---|
| Treatment | LL and CT/TT | Others |
| OND | 38 (13.1%) | 108 (37.1%) |
| Placebo | 32 (11.0%) | 113 (38.8%) |

Example 6—Analysis of Treatment Effects on Usage with Adjustment for Differences at Baseline Due to Genotype: The Methamphetamine/Ondansetron Study Methods: Data were modeled using generalized estimating equations (GEE). The dependent variable for analysis was binary: 0=subject used methamphetamine during the week and 1=subject did not use methamphetamine during the week. Independent variables were genotype, group, weeks since randomization and the interaction between treatment group and weeks since randomization. The hypothesis of primary interest asked if treatment with genotype influences the effect of ondansetron on usage. Specifically, this hypothesis was tested by asking if the week×group×genotype interaction differed significantly from zero. The model's group and genotype terms allowed for possible differences at baseline due to ineffective randomization and genotype, respectively. Group consisted of two levels: placebo vs. all active arms combined, where all active arms were combined at the request of the study sponsor and investigators. Subjects were of three different genotypes—SS, LL and LS. At the request of the investigator, two, separate GEE analyses were run, one for each pairing of a homozygote with the heterozygote (i.e., SS-LS and LL-LS). Due to the small quantity of subjects for which genotyping was conducted (n=34), hypothesis testing used Type III generalized score statistics. Analysis was restricted to data obtained post-randomization.

Results: Data were available on 34 subjects. The attached results indicate that the proportion of subjects with a methamphetamine-free week remained roughly steady for the active group but declined over time for the placebo arm. The difference in change over time between active and placebo approached statistical significance for the LLLS-adjusted analysis (p=0.0586) but not for the SSLS-adjusted analysis (p=0.5711). Neither analysis indicates that genotype influenced the treatment effect (p=0.6125 for SSLS and p=0.7740 for LLLS).

All results presented here need to be interpreted with caution, because drop-out exceeded 50% by the end of the study (1−15/34=19/34 0.56), and GEE analysis assumed that drop-outs were not treatment-related.

| | Proportion with Clean Week SSLS | | | | | | | | | | |
|---|---|---|---|---|---|---|---|---|---|---|---|
| | No Active | | | | | | Yes Active | | | | |
| STUDY WEEK | No | | | Yes | | | No | | | Yes | |
| ELAPSED SINCE RANDOMIZATION | N | Mean | SD | N | Mean | SD | N | Mean | SD | N | Mean | SD | N |

| STUDY WEEK ELAPSED SINCE RANDOMIZATION | N | Mean | SD | N | Mean | SD | N | Mean | SD | N | Mean | SD | N |
|---|---|---|---|---|---|---|---|---|---|---|---|---|---|
| 1 | 34 | 0.67 | 0.58 | 3 | 1.00 | 0.00 | 2 | 0.67 | 0.50 | 9 | 0.50 | 0.51 | 18 |
| 2 | 30 | 0.50 | 0.71 | 2 | 0.50 | 0.71 | 2 | 0.44 | 0.53 | 9 | 0.50 | 0.52 | 14 |
| 3 | 29 | 0.50 | 0.71 | 2 | 1.00 | 0.00 | 2 | 0.43 | 0.53 | 7 | 0.59 | 0.51 | 17 |
| 4 | 28 | 0.50 | 0.71 | 2 | 0.50 | 0.71 | 2 | 0.25 | 0.46 | 8 | 0.53 | 0.52 | 15 |
| 5 | 23 | 0.50 | 0.71 | 2 | 0.50 | 0.71 | 2 | 0.33 | 0.52 | 6 | 0.42 | 0.51 | 12 |
| 6 | 21 | 0.50 | 0.71 | 2 | 0.50 | 0.71 | 2 | 0.33 | 0.52 | 6 | 0.30 | 0.48 | 10 |
| 7 | 21 | 0.00 | . | 1 | 0.50 | 0.71 | 2 | 0.20 | 0.45 | 5 | 0.45 | 0.52 | 11 |
| 8 | 15 | 0.00 | 0.00 | 2 | 0.50 | 0.71 | 2 | 0.00 | 0.00 | 4 | 0.50 | 0.55 | 6 |

| Score Statistics For Type 3 GEE Analysis | | | |
|---|---|---|---|
| Source | DF | Chi-Square | Pr > ChiSq |
| Active | 1 | 0.94 | 0.3323 |
| study_week | 1 | 4.51 | 0.0337 |
| study_week × Active | 1 | 0.32 | 0.5711 |
| study_week × Active × SSLS | 1 | 0.26 | 0.6125 |

| | Proportion with Clean Week LLLS | | | | | | | | | | | | |
|---|---|---|---|---|---|---|---|---|---|---|---|---|---|
| | No Active | | | | | | Yes Active | | | | | | |
| STUDY WEEK | No | | | Yes | | | No | | | Yes | | | |
| ELAPSED SINCE RANDOMIZATION | N | Mean | SD | N | Mean | SD | N | Mean | SD | N | Mean | SD | N |
| 1 | 34 | 0.67 | 0.58 | 3 | 0.50 | 0.53 | 8 | 0.67 | 0.50 | 9 | 0.58 | 0.51 | 12 |
| 2 | 30 | 0.33 | 0.58 | 3 | 0.33 | 0.52 | 6 | 0.50 | 0.53 | 8 | 0.60 | 0.52 | 10 |
| 3 | 29 | 0.50 | 0.71 | 2 | 0.71 | 0.49 | 7 | 0.43 | 0.53 | 7 | 0.58 | 0.51 | 12 |
| 4 | 28 | 0.00 | 0.00 | 2 | 0.50 | 0.55 | 6 | 0.38 | 0.52 | 8 | 0.55 | 0.52 | 11 |
| 5 | 23 | 0.00 | 0.00 | 2 | 0.25 | 0.50 | 4 | 0.50 | 0.55 | 6 | 0.50 | 0.53 | 10 |
| 6 | 21 | 0.00 | 0.00 | 2 | 0.50 | 0.58 | 4 | 0.50 | 0.55 | 6 | 0.25 | 0.46 | 8 |
| 7 | 21 | 0.00 | 0.00 | 2 | 0.25 | 0.50 | 4 | 0.25 | 0.50 | 4 | 0.56 | 0.53 | 9 |
| 8 | 15 | 0.00 | 0.00 | 2 | 0.00 | . | 1 | 0.00 | 0.00 | 4 | 0.57 | 0.53 | 7 |

| Score Statistics For Type 3 GEE Analysis | | | |
|---|---|---|---|
| Source | DF | Chi-Square | Pr > ChiSq |
| Active | 1 | 0.88 | 0.3482 |
| study_week | 1 | 4.52 | 0.0334 |
| study_week × Active | 1 | 3.58 | 0.0586 |
| study_week × Active × LLLS | 1 | 0.08 | 0.7740 |

Example 7—Analysis of Treatment Effects on Usage with Adjustment for Differences at Baseline Due to Genotype: The Methamphetamine/Ondansetron Study (Part II)

Methods: Data were modeled using generalized estimating equations (GEE). The dependent variable for analysis was binary: 0=subject used methamphetamine during the week and 1=subject did not use methamphetamine during the week. Independent variables were genotype, group, weeks since randomization and the interaction between treatment group and weeks since randomization. The hypothesis of primary interest asked if treatment with ondansetron influences rate of change in methamphetamine usage over time. Specifically, this hypothesis was tested by asking if the week×group interaction differed significantly from zero. The model's group and genotype terms allowed for possible differences at baseline due to ineffective randomization and genotype, respectively. Group consisted of two levels: placebo vs. all active arms combined, where all active arms were combined at the request of the study sponsor and investigators. Subjects were of three different genotypes—SS, LL and LS. At the request of the investigator, two, separate GEE analyses were run, one for each pairing of a homozygote with the heterozygote (i.e., SS-LS and LL-LS). Due to the small quantity of subjects for which genotyping was conducted (n=34), hypothesis testing used Type III generalized score statistics. Analysis was restricted to data obtained post-randomization.

Results: Data were available on 34 subjects. The attached results indicate that the proportion of subjects with a methamphetamine-free week remained roughly steady for the active group but declined over time for the placebo arm. The difference in slopes between active and placebo approached statistical significance for each analysis (p=0.0525 for SSLS-adjusted and p=0.0510 for LLLS-adjusted). These results need to be interpreted with caution, however, because drop-out exceeded 50% by the end of the study $(1 - 15/34 = 19/34 \approx 0.56)$, and GEE analysis assumed that drop-outs were not treatment-related.

| STUDY WEEK ELAPSED SINCE RANDOMIZATION | Proportion with Clean Week Active Arm | | | | | |
|---|---|---|---|---|---|---|
| | No | | | Yes | | |
| | N | Mean | SD | N | Mean | SD | N |
| 1 | 34 | 0.67 | 0.49 | 12 | 0.55 | 0.51 | 20 |
| 2 | 30 | 0.45 | 0.52 | 11 | 0.50 | 0.52 | 16 |
| 3 | 29 | 0.44 | 0.53 | 9 | 0.63 | 0.50 | 19 |
| 4 | 28 | 0.30 | 0.48 | 10 | 0.53 | 0.51 | 17 |
| 5 | 23 | 0.38 | 0.52 | 8 | 0.43 | 0.51 | 14 |
| 6 | 21 | 0.38 | 0.52 | 8 | 0.33 | 0.49 | 12 |
| 7 | 21 | 0.17 | 0.41 | 6 | 0.46 | 0.52 | 13 |
| 8 | 15 | 0.00 | 0.00 | 6 | 0.50 | 0.53 | 8 |

| Source | DF | Chi-Square | p-value |
|---|---|---|---|
| SSLS | 1 | 0.55 | 0.4587 |
| study_week | 1 | 4.55 | 0.0329 |
| study_week × Active | 1 | 3.76 | 0.0525 |
| Active | 1 | 0.68 | 0.4103 |

| STUDY WEEK ELAPSED SINCE RANDOMIZATION | Proportion with Clean Week Active Arm | | | | | |
|---|---|---|---|---|---|---|
| | No | | | Yes | | |
| | N | Mean | SD | N | Mean | SD | N |
| 1 | 34 | 0.67 | 0.49 | 12 | 0.55 | 0.51 | 20 |
| 2 | 30 | 0.45 | 0.52 | 11 | 0.50 | 0.52 | 16 |
| 3 | 29 | 0.44 | 0.53 | 9 | 0.63 | 0.50 | 19 |
| 4 | 28 | 0.30 | 0.48 | 10 | 0.53 | 0.51 | 17 |
| 5 | 23 | 0.38 | 0.52 | 8 | 0.43 | 0.51 | 14 |
| 6 | 21 | 0.38 | 0.52 | 8 | 0.33 | 0.49 | 12 |
| 7 | 21 | 0.17 | 0.41 | 6 | 0.46 | 0.52 | 13 |
| 8 | 15 | 0.00 | 0.00 | 6 | 0.50 | 0.53 | 8 |

| Source | DF | Chi-Square | p-value |
|---|---|---|---|
| LLLS | 1 | 0.34 | 0.5597 |
| study_week | 1 | 4.58 | 0.0323 |
| study_week × Active | 1 | 3.81 | 0.0510 |
| Active | 1 | 0.83 | 0.3636 |

Example 8—Association Between Genotype of the Serotonin Transporter-Linked Polymorphic Region of the Serotonin Transporter Gene and Age of Onset of Methamphetamine Use Methamphetamine is a highly addictive central nervous system stimulant, and both current and recently abstinent chronic methamphetamine-dependent individuals can develop irreversible structural and neurochemical changes in the brain with long-lasting cognitive and motor deficits (Chang et al., 2002; Seiden and Ricaurte, 1987; Thompson et al., 2004).

Methamphetamine dependence is on the rise in the United States and other parts of the world (Winslow et al., 2007). According to surveys funded by the National Institute on Drug Abuse in 2005, 10.4 million Americans aged 12 years and older and 4.5% of 12th graders had used methamphetamine at least once in their lifetime (National Institute on Drug Abuse, 2006). Increased production and spread of methamphetamine use to other parts of the country from its traditional endemic areas in the West and Midwest have raised additional concern about the increasing prevalence of methamphetamine addiction (Ehlers et al., 2007; Johnson et al., in press).

Several studies conducted in various countries, and with different ethnic populations, have reported an increased prevalence of adult methamphetamine dependence when the onset of methamphetamine use occurred in adolescence (Nordahl et al., 2003). The progression from first-time drug use to the development of dependence does, however, depend upon the interplay of both genetic and environmental factors (Goldman et al., 2005; McGue et al., 2006); therefore, not all adolescents who experiment with methamphetamine progress to methamphetamine dependence as adults (Fowler et al., 2007).

The importance of genetic factors has been highlighted by Ehlers and colleagues (2007), who showed, in a relatively homogenous population of Native Americans in Southwest California, that the liability toward the initiation of stimulant use is highly heritable at an estimated rate of 38%. Understanding the nature of the genetic factors that increase the risk of stimulant initiation can aid in appropriate screening and early intervention for those who are environmentally vulnerable to methamphetamine exposure, and can facilitate the development of targeted medications toward the treatment of those who become dependent.

The chronic administration of methamphetamine to rats damages the structure of the central nervous system by degrading the terminal ends of serotonin (5-HT) neurons (Ricaurte et al., 1980). Human brain imaging studies also have shown that chronic methamphetamine users can exhibit significantly reduced 5-HT transporter (5-HTT) densities, an indication of terminal neuronal damage, in different brain regions (Sekine et al., 2006). Because these reductions in 5-HTT density occurred in a time- and concentration-dependent manner, individuals with the earliest onset and greatest use of methamphetamine can be expected to experience the most structural brain damage.

5-HT neurons are tonic inhibitors of dopamine neurons in the central nervous system (Johnson, 2000). Therefore, the degradation of 5-HT neurons can lead to a rise in extracellular dopamine levels (Nordahl et al., 2003), which in turn increases the individual's behavioral propensity toward further methamphetamine use (Volkow and Li, 2004).

It is, therefore, reasonable to hypothesize that, once established, chronic methamphetamine use sets up a feedforward process whereby increased methamphetamine use leads to a rise in damage to 5-HT neurons, which in turn leads to an enhancement of the behavioral drive to use more methamphetamine. As a logical extension of this hypothesis, it would, therefore, be reasonable to suspect that a component of the biological or genetic vulnerability toward the initiation of methamphetamine use might reside within regulatory systems that modulate 5-HT function and density.

Of the mechanisms that control synaptic 5-HT function, perhaps the most compelling relates to the functional state of the pre-synaptic 5-HTT. The 5-HTT is responsible for removing 5-HT from the synaptic cleft (Lesch et al., 2002). Indeed, up to 60% of neuronal 5-HT function is gated by the 5-HTT. Synaptic clearance of 5-HT is determined by the number of 5-HTTs expressed at the pre-synaptic surface and the affinity of 5-HTTs to 5-HT (Beckman and Quick, 1998).

The 5-HTT gene is found at the SLC6A4 locus on chromosome 17q11.1-q12, and its 5'-regulatory promoter region contains a functional polymorphism known as the 5-HTT-linked polymorphic region (5'-HTTLPR) (Heils et al., 1996, 1997). This polymorphism is an insertion/deletion mutation in which the long (L) variant has 44 base pairs that are absent in the short (S) variant. The L-allelic variant of the 5'-HTTLPR is associated with increased transcription rates in lymphoblasts and in cell culture. In the general population, the LL genotype, compared with the SS and heterozygous (LS) genotypes, is associated with greater 5-HT uptake into human platelets (Greenberg et al., 1999) and lymphoblasts (Lesch et al., 1996) and greater [$^{123}$I]2 beta-carboxymethoxy-3 beta-(4-iodophenyl)tropane (β-CIT) binding in human raphe nuclei (Heinz et al., 2000). Hence, individuals with the LL genotype have greater uptake and, presumably, reduced intrasynaptic 5-HT levels and 5-HT neurotransmission (Heils et al., 1996; Lesch et al., 1996). Johnson (2000) has proposed that this relative hyposerotonergic state can predispose an individual to impulsive behavior, including substance-taking behavior. Since heightened levels of impulsive behavior have been associated with methamphetamine use (Semple et al., 2005), although it has been debated whether it is a cause or consequence, it is hypothesized that these individuals with the LL genotype may also be more prone than S-carriers to develop early-onset methamphetamine use.

Early-onset methamphetamine use increases the lifetime prevalence of methamphetamine dependence. An earlier onset of methamphetamine use leads to greater damage to the terminal ends of serotonin neurons, more reduction in serotonin transporter (5-HTT) density, and an increased propensity toward further methamphetamine use. Because genetic variation within the promoter region of the 5 HTT gene (the 5-HTT-linked polymorphic region; 5'-HTTLPR) leads to differential expression of the 5-HTT, we examined, for the first time, whether this could be a candidate site associated with predisposition toward early-onset methamphetamine use. We sought to determine whether there is a differential association between the long (L) and short (S) polymorphic variants of the 5'-HTTLPR and the age of first methamphetamine use.

Materials and Methods

Subjects

Thirty-six out of 150 treatment-seeking individuals who consented to this genetic evaluation, and who were enrolled in a clinical trial for the treatment of methamphetamine dependence, were included in this study. All subjects were at least 18 years of age and diagnosed as methamphetamine dependent by Diagnostic and Statistical Manual of Mental Disorders, 4th edition (DSM-IV) criteria (American Psychiatric Association, 1994). The enrolled subjects were required to have at least one methamphetamine-positive urine specimen during the 2-week baseline period. They were in good physical health as determined by physical and laboratory examinations (i.e., hematological assessment, biochemistry, and urinalysis). Exclusion criteria were current dependence on any psychoactive substance (as defined by DSM-IV criteria) besides methamphetamine, nicotine, or marijuana, or physiological dependence on alcohol or a sedative-hypnotic, e.g., a benzodiazepine requiring medical detoxification. We also excluded individuals with current diagnoses of anxiety, affective, or psychotic disorders. We did not study individuals who: were mandated by the courts to be treated for methamphetamine dependence, were pregnant or not using an acceptable form of contraception (i.e., oral contraceptive, hormonal or surgical implant, sterilization, or spermicide and barrier), were taking psychotropic medication, were using opiate substitutes within 2 months of enrollment, were asthmatic, or had AIDS.

We received ethics approval from the appropriate institutional review boards. Study subjects were recruited between August 2002 and July 2003 by newspaper, television, or radio advertisements.

After obtaining written informed consent, and prior to the subjects' enrollment in the clinical trial, we determined psychiatric diagnosis using the Structured Clinical Interview for DSM-IV (First et al., 1994) and age of onset of methamphetamine use using the Addiction Severity Index-Lite (Cacciola et al., 2007). Other structured measures were collected at enrollment and at scheduled intervals during the clinical trial, as reported elsewhere (Johnson et al., in press).

Collection of Blood Samples for Genotyping

Ten milliliters of blood was drawn from each subject at baseline to obtain white blood cells for the determination of 5'-HTTLPR genotypes.

Genotyping

DNA was extracted using a Gentra Puregene® kit (QIAGEN Inc., Valencia, Calif.). Fifty nanograms of genomic DNA was polymerase chain reaction amplified for the 5'-HTTLPR 44-base-pair promoter-region repeat polymorphism using the primers 5'-TCCTCCG CTTTGGCGCCTCTTCC-3' (forward; SEQ ID NO:1) and 5'-TGGGG GTTGCAGGGGAGATCCTG-3' (reverse; SEQ ID NO:2) in a 20-μl final volume with 2.5 U of BIOLASE™ DNA polymerase (Bioline, London, United Kingdom), 1×NH4 reaction buffer, 0.5 mM MgCl2, 0.8 mM deoxynucleotide triphosphates, dimethyl sulfoxide, and 100 nM of each primer. The thermal cycling included initial denaturation at 95° C. for 15 min, 45 cycles of 94° C. for 30 s, 65.5° C. for 90 s, and 72° C. for 1 min, a final extension of 72° C. for 10 min, and a terminal hold at 4° C. The alleles for the 5'-HTTLPR were separated by gel electrophoresis using 3% agarose (Cambrex, Rockland, Me.) and visualized by an ethidium bromide/ultraviolet detection system.

Statistical Analysis

We used the Cox proportional-hazards model to assess the relative risk of an earlier onset of methamphetamine use for the LL genotype compared with heterozygotes (LS) and S carriers of the 5'-HTTLPR of the 5-HTT gene. Furthermore, we tested additive, dominant, and recessive genetic models in the analyses. We used the Kaplan-Meier method to estimate the probabilities in time (years) for which individuals with the LL genotype vs. LS heterozygotes or S carriers first used methamphetamine, and a log-rank test to compare these probabilities. An analysis of variance was used to compare the mean ages of onset of those with the LL genotype vs. LS heterozygotes or S carriers of the 5'-HTTLPR.

RESULTS DNA samples from 36 methamphetamine-dependent subjects aged between 19 years and 55 years were genotyped in this study. Of these subjects, 78% were White and 12% were Hispanic; 32% were female and 68% male. Additionally, the genotypic distribution of the cohort was 16% LL, 53% LS, and 31% SS (Table 1).

The L homozygotes showed a significantly higher risk of an earlier onset of methamphetamine use compared with LS heterozygotes (hazard ratio=3.7; 95% confidence interval [CI]=1.3-10.0; p=0.01). Compared with S homozygotes, LL subjects also showed an earlier onset of methamphetamine use (hazard ratio=2.78, 95% CI=0.98-7.69; p=0.05), while the difference between LS and SS subjects was not statistically significant. When the combined mean ages of onset of methamphetamine use in SS and LS subjects were compared with subjects with the LL genotype, the risk of first-time use of methamphetamine in L homozygotes was 3.27 times higher (95% CI=1.26-8.50; p=0.01) than among S-carriers. This suggests a dominant effect of the L allele over the S allele.

Figure 10:
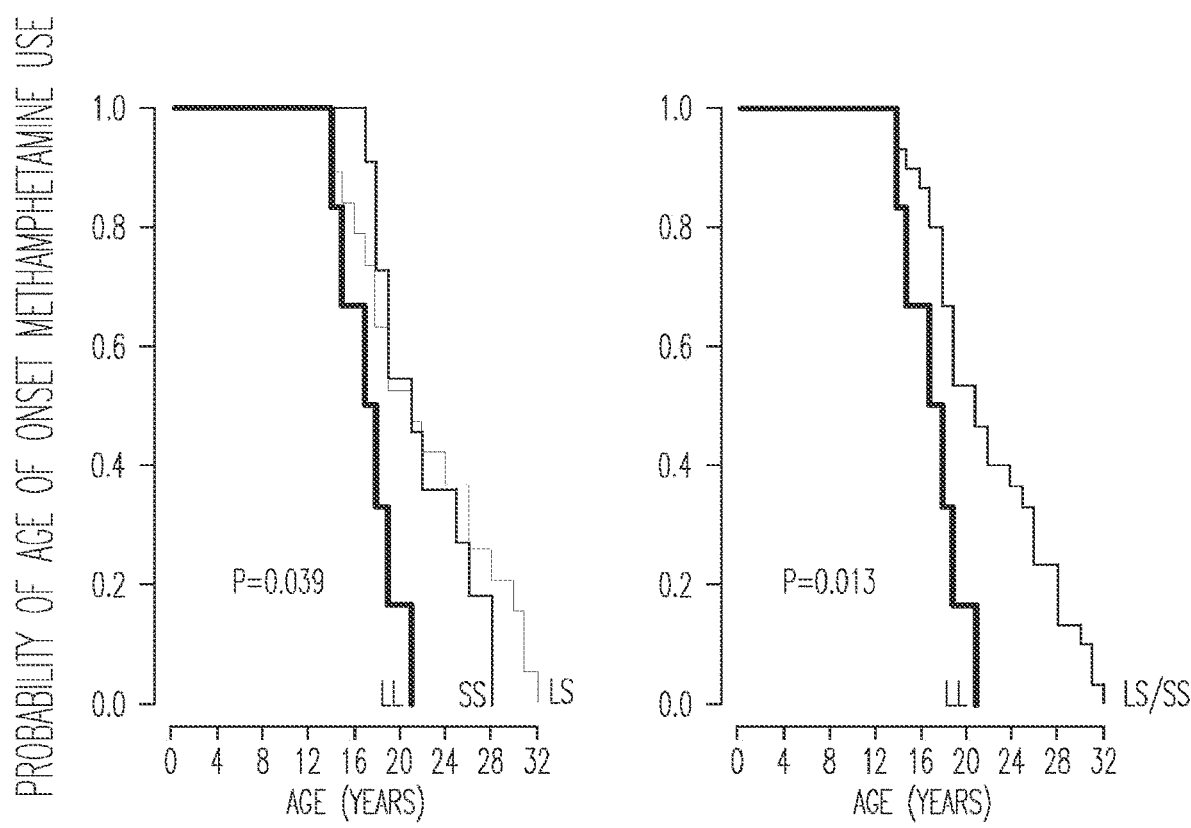
FIG. 10 shows the probability of the age of onset of methamphetamine use for each of the three 5'-HTTLPR genotypes.

Using the Kaplan-Meier method (FIG. 10), it can be seen that individuals with the LL genotype compared with their LS or SS counterparts became dependent on methamphetamine significantly earlier (log-rank, all p values<0.05). Furthermore, individuals with the LL genotype, compared with S-carriers, first used methamphetamine about 5 years earlier (p=0.04) (Table 1). Table 1 describes the ages of onset of methamphetamine use for the 5'-HTTLPR Genotypes—M=males; F=females.

TABLE 1

Example 8:

| A. | LL Genotype (n = 6) M = 2; F = 4 | LS Genotype (n = 19) M = 14; F = 5 | SS Genotype (n = 11) M = 2; F = 9 | p Value (F Value) |
|---|---|---|---|---|
| Mean (SD) age of onset | 17.3 (1.63) | 22.2 (6.35) | 21.9 (3.22) | 0.13 (2.11) |

| | LL Genotype (n = 6) M = 2; F = 4 | LS/SS Genotype (n = 30) M = 16; F = 14 | p Value (F Value) |
|---|---|---|---|
| Mean (SD) age of onset | 17.3 (1.63) | 22.1 (5.35) | 0.04 (4.31) |

| | LL/LS Genotype (n = 25) M = 16; F = 9 | SS Genotype (n = 11) M = 2; F = 9 | p Value (F Value) |
|---|---|---|---|
| Mean (SD) age of onset | 21.0 (5.93) | 21.9 (3.22) | 0.69 (0.16) |

Discussion—Example 8—

The data disclosed herein suggest that among methamphetamine-dependent individuals, possession of the LL genotype in the 5'-HTTLPR, compared with their S-carrier counterparts, was associated with more than a 3 times greater risk of having had an earlier onset of methamphetamine use.

The 5-HTT plays a role in controlling the duration and degree of serotonergic neurotransmission (Johnson, 2000). The L allele of the promoter region of the 5-HTT gene, which transcribes a higher number of 5-HTT copies compared with the S allele (Heils et al., 1996), alters transporter expression levels in different brain regions (Heinz et al., 2000). As mentioned earlier, higher expression levels of 5-HTTs are associated with increased 5-HT uptake, leading to a relative intrasynaptic hyposerotonergic state and reduced serotonergic neurotransmission (Greenberg et al., 1999). We also proposed that individuals with the LL genotype in the 5' HTTLPR who possess this relative hyposerotonergic state would have a greater propensity toward impulsive behavior and, consequently, methamphetamine use.

Further, we speculated that the acute intake of methamphetamine, by producing a sudden release of 5-HT (Winslow et al., 2007) and increased serotonergic transmission due to enhanced firing of serotonergic neurons in raphe nuclei (Johnson, 2000; Rao et al., 2007), would result in a transient amelioration of the relative hyposerotonergic state. Because individuals with this relative hyposerotonergic state might also be prone to negative affect (Young and Leyton, 2002), the relief of these symptoms by methamphetamine would be expected to heighten its reinforcing effects. Consequently, there would be increased stimulus toward further methamphetamine use. Notably, however, chronic methamphetamine use damages the terminal ends of 5-HT neurons (Nordahl et al., 2003). This decreases 5-HTT density (Sekine et al., 2006), and the resultant disinhibition of 5-HT-mediated tonic control of dopamine release would serve to enhance further the rise in extracellular dopamine levels following methamphetamine use. Hypothetically, this would create a feed-forward pharmacological process whereby increased methamphetamine taking provides an ever increasing stimulus for its further use.

Because this is the first study to examine whether methamphetamine-dependent individuals who vary in genotype in the 5' HTTLPR differ in the age of onset of methamphetamine use, there are no studies against which we can directly compare our results. Nevertheless, Johnson and colleagues (2008) showed recently that L-carriers in the 5' HTTLPR, compared with their S-carrier counterparts, have a greater history and severity of lifetime drinking. However, it remains to be determined whether individuals who develop dependence on alcohol, methamphetamine, or both share an appreciable amount of commonly inherited genetic traits.

This study has five notable limitations. First, this study was only a preliminary analysis with a small sample population that did not provide sufficient statistical power to examine for any possible ethnic or gender differences associated with genotypic variability. Indeed, a second caveat is that because of the small sample size, the genotypic groups were unbalanced in size, thereby reducing our ability to draw firm conclusions from our results. Large-scale studies are, therefore, needed to replicate and extend our findings. Third, because of the cross-sectional nature of the study, we were not able to assess how genetic variation in the 5' HTTLPR interacted with the progression of methamphetamine use over time. Fourth, our cohort was composed of methamphetamine-dependent individuals who were seeking treatment. Since treatment seekers can vary in pathophysiology from those in the community, often being more motivated and generally healthier, we do not know whether our findings can be generalized to the entire population of those who are using methamphetamine. Fifth, because the cohort for this genetic study was not drawn from the general population, but rather from a subpopulation of treatment seeking, methamphetamine-dependent individuals, the absolute risk of an early onset of methamphetamine use among those in the community who possess the LL genotype of 5' HTTLPR cannot be determined.

In summary, our findings provide preliminary evidence that genetic vulnerability may be heritable, and that possession of the LL genotype in the 5'-HTTLPR might confer increased predisposition toward early-onset methamphetamine use.

Example 8 Bibliography

American Psychiatric Association, 1994. Diagnostic and Statistical Manual of Mental Disorders, 4th edition. American Psychiatric Association, Washington, D.C.

Beckman, M. L., Quick, M. W., 1998. Neurotransmitter transporters: regulators of function and functional regulation. J. Membr. Biol. 164, 1-10.

Cacciola, J. S., Alterman, A. I., McLellan, A. T., Lin, Y.-T., Lynch, K. G., 2007. Initial evidence for the reliability and validity of a "Lite" version of the Addiction Severity Index. Drug Alcohol Depend. 87, 297-302.

Chang, L., Ernst, T., Speck, O., Patel, H., DeSilva, M., Leonido-Yee, M., Miller, E. N., 2002. Perfusion MRI and computerized cognitive test abnormalities in abstinent methamphetamine users. Psychiatry Res. 114, 65-79.

Ehlers, C. L., Wall, T. L., Corey, L., Lau, P., Gilder, D. A., Wilhelmsen, K., 2007. Heritability of illicit drug use and transition to dependence in Southwest California Indians. Psychiatr. Genet. 17, 171-176.

First, M. B., Spitzer, R. L., Gibbon, M., Williams, J. B. W., 1994. Structured Clinical Interview for DSM-IV Axis I Disorders—Patient Edition (SCID-I/P, Version 2.0). New York State Psychiatric Institute, Biometrics Research Department, New York.

Fowler, T., Lifford, K., Shelton, K., Rice, F., Thapar, A., Neale, M. C., McBride, A., van den Bree, M. B., 2007. Exploring the relationship between genetic and environmental influences on initiation and progression of substance use. Addiction 102, 413-422.

Goldman, D., Oroszi, G., Ducci, F., 2005. The genetics of addictions: uncovering the genes. Nat. Rev. Genet. 6, 521-532.

Greenberg, B. D., Tolliver, T. J., Huang, S. J., Li, Q., Bengel, D., Murphy, D. L., 1999. Genetic variation in the serotonin transporter promoter region affects serotonin uptake in human blood platelets. Am. J. Med. Genet. 88, 83-87.

Heils, A., Mossner, R., Lesch, K. P., 1997. The human serotonin transporter gene polymorphism—basic research and clinical implications. J. Neural Transm. 104, 1005-1014.

Heils, A., Teufel, A., Petri, S., Stober, G., Riederer, P., Bengel, D., Lesch, K. P., 1996. Allelic variation of human serotonin transporter gene expression. J. Neurochem. 66, 2621-2624.

Heinz, A., Jones, D. W., Mazzanti, C., Goldman, D., Ragan, P., Hommer, D., Linnoila, M., Weinberger, D. R., 2000. A relationship between serotonin transporter genotype and in vivo protein expression and alcohol neurotoxicity. Biol. Psychiatry 47, 643-649.

Johnson, B. A., 2000. Serotonergic agents and alcoholism treatment: rebirth of the subtype concept—an hypothesis. Alcohol. Clin. Exp. Res. 24, 1597-1601.

Johnson, B. A., Ait-Daoud, N., Elkashef, A. M., Smith, E. V., Kahn, R., Vocci, F., Li, S.-H., Bloch, D. A., Methamphetamine Study Group, in press. A preliminary randomized, double-blind, placebo-controlled study of the safety and efficacy of ondansetron in the treatment of methamphetamine dependence. Int. J. Neuropsychopharmacol.

Johnson, B. A., Javors, M. A., Roache, J. D., Seneviratne, C., Bergeson, S. E., Ait-Daoud, N., Dawes, M. A., Ma, J. Z., 2008. Can serotonin transporter genotype predict serotonergic function, chronicity, and severity of drinking? Prog. Neuropsychopharmacol. Biol. Psychiatry 32, 209-216.

Lesch, K. P., Bengel, D., Heils, A., Sabol, S. Z., Greenberg, B. D., Petri, S., Benjamin, J., Muller, C. R., Hamer, D. H., Murphy, D. L., 1996. Association of anxiety-related traits with a polymorphism in the serotonin transporter gene regulatory region. Science 274, 1527-1531.

Lesch, K. P., Greenberg, B. D., Higley, J. D., 2002. Serotonin transporter, personality, and behavior: toward dissection of gene-gene and gene-environment interaction. In: Benjamin, J., Ebstein, R. P., Belmaker, R. H. (Eds.), Molecular Genetics and the Human Personality. American Psychiatric Publishing, Washington, D.C., pp. 109-136.

McGue, M., Iacono, W. G., Krueger, R., 2006. The association of early adolescent problem behavior and adult psychopathology: a multivariate behavioral genetic perspective. Behav. Genet. 36, 591-602.

National Institute on Drug Abuse, 2006. NIDA InfoFacts: methamphetamine (See NIDA website). U.S. Department of Health and Human Services, Bethesda, Md.

Nordahl, T. E., Salo, R., Leamon, M., 2003. Neuropsychological effects of chronic methamphetamine use on neurotransmitters and cognition: a review. J. Neuropsychiatry Clin. Neurosci. 15, 317-325.

Rao, H., Gillihan, S. J., Wang, J., Korczykowski, M., Sankoorikal, G. M., Kaercher, K. A., Brodkin, E. S., Detre, J. A., Farah, M. J., 2007. Genetic variation in serotonin transporter alters resting brain function in healthy individuals. Biol. Psychiatry 62, 600-606.

Ricaurte, G. A., Schuster, C. R., Seiden, L. S., 1980. Long-term effects of repeated methylamphetamine administration on dopamine and serotonin neurons in the rat brain: a regional study. Brain. Res. 193, 153-163.

Seiden, L. S., Ricaurte, G., 1987. Neurotoxicity of methamphetamine and related drugs. In: Meltzer, H. Y. (Ed.), Psychopharmacology: the third generation of progress. Raven Press, New York, pp. 359-366.

Sekine, Y., Ouchi, Y., Takei, N., Yoshikawa, E., Nakamura, K., Futatsubashi, M., Okada, H., Minabe, Y., Suzuki, K., Iwata, Y., Tsuchiya, K. J., Tsukada, H., Iyo, M., Mori, N., 2006. Brain serotonin transporter density and aggression in abstinent methamphetamine abusers. Arch. Gen. Psychiatry 63, 90-100.

Semple, S. J., Zians, J., Grant, I., Patterson, T. L., 2005. Impulsivity and methamphetamine use. J. Subst. Abuse Treat. 29, 85-93.

Thompson, P. M., Hayashi, K. M., Simon, S. L., Geaga, J. A., Hong, M. S., Sui, Y., Le, J. Y., Toga, A. W., Ling, W., London, E. D., 2004. Structural abnormalities in the brains of human subjects who use methamphetamine. J. Neurosci. 24, 6028-6036.

Volkow, N. D., Li, T.-K., 2004. Drug addiction: the neurobiology of behaviour gone awry. Nat. Rev. Neurosci. 5, 963-970.

Winslow, B. T., Voorhees, K. I., Pehl, K. A., 2007. Methamphetamine abuse. Am. Fam. Physician 76, 1169-1174.

Young, S. N., Leyton, M., 2002. The role of serotonin in human mood and social interaction. Insight from altered tryptophan levels. Pharmacol. Biochem. Behav. 71, 857-865.

Example 9

The data disclosed in this example demonstrate that individuals with the TT allele have the highest craving in the human laboratory. This is a human laboratory cue study where individuals were presented with either alcohol or neutral cues. Alcoholics preferred the alcohol to the neutral cues. It can be seen below that the TT alcoholics had the highest craving and preference for the alcohol cues compared with their Gx counterparts. These data supplement previous studies indicating that the TT allele is associated with highest drinking severity, and that those with the TT allele are responsive to ondansetron treatment.

Section 1, Example 9—Difference Between Average of $4^{th}$ and $5^{th}$ Time Points and Average of $1^{st}$ and $2^{nd}$ and $3^{rd}$ Time Points in Visual Analog Scale (VAS) Craving

TABLE 1

Example 9: ANOVA table of difference between average of $4^{th}$ and $5^{th}$ time points and average of $1^{st}$ and $2^{nd}$ and $3^{rd}$ time points in VAS craving (TT, TG, GG)

|  | "Urge to Drink" | | "Crave for a Drink" | |
| --- | --- | --- | --- | --- |
| Variable | F-Value | p-Value | F-Value | p-Value |
| Treatment (Tryptophan depletion) | 2.12 | 0.151 | 0.05 | 0.818 |
| RS1042173 (TT, TG, GG) | 0.23 | 0.796 | 0.10 | 0.901 |
| Cue | 7.54 | 0.008 | 6.34 | 0.014 |
| RS1042173*Cue | 3.39 | 0.040 | 1.86 | 0.163 |
| Age of onset | 0.61 | 0.441 | 0.26 | 0.613 |

TABLE 2

Example 9: Model-based estimates of the mean difference of difference between average of $4^{th}$ and $5^{th}$ time points and average of $1^{st}$ and $2^{nd}$ and $3^{rd}$ time points in VAS craving (TT, TG, GG)

| VAS | Comparison | Estimated Difference | SE | p-Value | Lower 95% CI | Upper 95% CI |
| --- | --- | --- | --- | --- | --- | --- |
| "Urge to drink" | ALCOHOL-NEUTRAL CUE | 7.46 | 2.72 | 0.008 | 2.03 | 12.88 |
|  | Under TT ALCOHOL-NEUTRAL CUE | 17.70 | 4.98 | 0.0007 | 7.75 | 27.66 |
| "Crave for a drink" | ALCOHOL-NEUTRAL CUE | 7.12 | 2.83 | 0.014 | 1.48 | 12.76 |
|  | Under TT ALCOHOL-NEUTRAL CUE | 14.98 | 5.23 | 0.006 | 4.55 | 25.42 |

TABLE 3

Example 9: ANOVA table of difference between average of $4^{th}$ and $5^{th}$ time points and average of $1^{st}$ and $2^{nd}$ and $3^{rd}$ time points in VAS craving (TT, TG/GG)

|  | "Urge to Drink" | | "Crave for a Drink" | |
| --- | --- | --- | --- | --- |
| Variable | F-Value | p-Value | F-Value | p-Value |
| Treatment (Tryptophan depletion) | 2.25 | 0.139 | 0.06 | 0.807 |
| RS1042173 (TT, TG/GG) | 0.28 | 0.603 | 0.20 | 0.656 |
| Cue | 11.63 | 0.001 | 8.68 | 0.004 |
| RS1042173*Cue | 6.69 | 0.012 | 3.70 | 0.059 |
| Age of onset | 0.62 | 0.440 | 0.28 | 0.600 |

TABLE 4

Model-based estimates of the mean difference of difference between average of $4^{th}$ and $5^{th}$ time points and average of $1^{st}$ and $2^{nd}$ and $3^{rd}$ time points in YAS craving (TT, TG/GG)

| VAS | Comparison | Estimated Difference | SE | p-Value | Lower 95% CI | Upper 95% CI |
| --- | --- | --- | --- | --- | --- | --- |
| "Urge to drink" | ALCOHOL-NEUTRAL CUE | 10.07 | 2.95 | 0.001 | 4.17 | 15.97 |
|  | Under TT ALCOHOL-NEUTRAL CUE | 17.70 | 4.96 | 0.0007 | 7.79 | 27.61 |
| "Crave for a drink" | ALCOHOL-NEUTRAL CUE | 9.08 | 3.08 | 0.004 | 2.93 | 15.23 |
|  | Under TT ALCOHOL-NEUTRAL CUE | 15.00 | 5.19 | 0.005 | 4.63 | 25.36 |

Section II—Example 9—Difference Between $4^{th}$ and $3^{rd}$ Time Points in VAS Craving

TABLE 1

Section II- Example 9: ANOVA table of difference between $4^{th}$ and $3^{rd}$ time points in VAS craving (TT, TG, GG)

|  | "Urge to Drink" | | "Crave for a Drink" | |
| --- | --- | --- | --- | --- |
| Variable | F-Value | p-Value | F-Value | p-Value |
| Treatment (Tryptophan depletion) | 1.51 | 0.222 | 0.15 | 0.697 |
| RS1042173 (TT, TG, GG) | 0.06 | 0.942 | 0.14 | 0.866 |
| Cue | 5.71 | 0.019 | 3.30 | 0.073 |
| RS1042173*Cue | 2.56 | 0.083 | 2.45 | 0.093 |
| Age of onset | 0.45 | 0.508 | 0.14 | 0.708 |

TABLE 2

Section II-Example 9: Model-based estimates of the mean difference between $4^{th}$ and $3^{rd}$ time points in VAS craving

| VAS | Comparison | Estimated Difference | SE | p-Value | Lower 95% CI | Upper 95% CI |
| --- | --- | --- | --- | --- | --- | --- |
| "Urge to drink" | ALCOHOL-NEUTRAL CUE | 8.56 | 3.58 | 0.019 | 1.44 | 15.69 |
|  | Under TT ALCOHOL-NEUTRAL CUE | 20.33 | 6.61 | 0.003 | 7.18 | 33.49 |
| "Crave for a drink" | ALCOHOL-NEUTRAL CUE | 7.23 | 3.98 | 0.073 | -0.70 | 15.16 |
|  | Under TT ALCOHOL-NEUTRAL CUE | 19.00 | 7.39 | 0.012 | 4.27 | 33.73 |

TABLE 3

Section II- Example 9: ANOVA table of difference between $4^{th}$ and $3^{rd}$ time points in VAS craving (TT, TG/GG)

| Variable | "Urge to Drink" | | "Crave for a Drink" | |
|---|---|---|---|---|
| | F-Value | p-Value | F-Value | p-Value |
| Treatment (Tryptophan depletion) | 1.58 | 0.212 | 0.12 | 0.726 |
| RS1042173 (TT, TG/GG) | 0.08 | 0.783 | 0.01 | 0.905 |
| Cue | 8.83 | 0.004 | 5.50 | 0.022 |
| RS1042173*Cue | 5.11 | 0.026 | 4.02 | 0.049 |
| Age of onset | 0.45 | 0.506 | 0.13 | 0.721 |

TABLE 4

Section II-Example 9: Model-based estimates of the mean difference between $4^{th}$ and $3^{rd}$ time points in VAS craving (TT, TG/GG)

| VAS | Comparison | Estimated Difference | SE | p-Value | Lower 95% CI | Upper 95% CI |
|---|---|---|---|---|---|---|
| "Urge to drink" | ALCOHOL-NEUTRAL CUE | 11.59 | 3.90 | 0.004 | 3.84 | 19.35 |
| | Under TT ALCOHOL-NEUTRAL CUE | 20.40 | 6.57 | 0.003 | 7.33 | 33.46 |
| "Crave for a drink" | ALCOHOL-NEUTRAL CUE | 10.25 | 4.37 | 0.022 | 1.54 | 18.95 |
| | Under TT ALCOHOL-NEUTRAL CUE | 18.99 | 7.38 | 0.012 | 4.29 | 33.69 |

Example 10—Genes Associated with Topiramate Effects

Genes Associated with Efficacy of Topiramate:
1. DISC1 (Disrupted in schizophrenia gene 1)
2. interactors in DISC1 pathway:
   a. NDE1
   b. PDE4D
   c. NDEL1
   d. PDE4B
3. Drug target receptor genes:
   a. Kinate receptor genes: GRIK1
   b. AMPA receptor genes: GluR1
   c. GABA genes: GABRA1
   d. Sodium channel proteins: SCN1A (sodium channel, voltage-gated, type I, alpha subunit)
4. Genes associated with Topiramate metabolism and availability:
   a. CYP2C19
   b. CYP3A4
   c. UGT2B7 (UDP glucuronosyltransferase 2 family, polypeptide B7)
   d. FABP2 (fatty acid binding protein 2, intestinal)
5. Genes associated with drug resistance:
   a. ABCB1 (ATP-BINDING CASSETTE, SUBFAMILY B, MEMBER 1)
   b. SCN2A (voltage-gated, type II, alpha)
   c. SCN2A2 (sodium channel, voltage-gated, type II, alpha 2 polypeptide)

Genes associated with adverse effects of Topiramate:
In addition to the genes listed above, following genes have also been studied in association with Topiramate adverse effects:

1. Genes coding for carbonic anhydrase (CA) enzyme:
   a. CA Class 11: CA2
   b. CA Class 1V: CA4
2. Weight loss/Anorexia: ADIPOQ (adiponectin, C1Q and collagen domain containing), HTR2C

Example 11-Analysis of Gene Patterns Related to Response to Ondansetron Treatment Genotype data was collected from 281 patients participating in a clinical trial wherein ondansetron was administered. Table 1 presents the coding of the raw data used for analysis: eight different genotypes were associated with each person, for a total of N=281 subjects.

TABLE 1

Coding of Genotypes for eight genetic variants

| ID | A | B | C | D | E | F | G | H |
|---|---|---|---|---|---|---|---|---|
| 100 | LS | TG | AG | AA | GG | CC | CT | AG |
| 104 | LL | TG | GG | GG | AA | CC | CT | AA |
| 106 | LS | GG | GG | AA | GG | CC | CT | AG |
| 110 | LS | TT | GG | AA | GG | CC | TT | AA |
| 113 | LL | TG | GG | AG | GG | CC | CT | GG |
| 114 | SS | GG | GG | AA | GG | CC | CT | AG |
| 117 | LS | TT | GG | AA | GG | CC | CC | GG |
| 119 | LL | TT | GG | GG | AA | CC | CT | AG |
| 120 | LL | TT | GG | AA | AG | CC | TT | AA |
| 122 | LS | TG | GG | AA | AA | CC | TT | AA |

Genotypes:
A = 5'-HTTLPR (sert)
B = rs1042173
C = rs1150226
D = rs1176713
E = rs1176719
F = rs17614942
G = rs4938056
H = rs1672717

Table 2 provides an outcome matrix wherein each person (identified by ID number) was assigned a responder status in several ways, ranging from reduction of average drinks per day by 2 or more drinks (Resp.1 in Table 2) to no heavy drinking days in the past 2 months (Resp.2), no more than 1 heavy drinking day (Resp.3), . . . , no more than 5 heavy drinking days (Resp. 6).

TABLE 2

Outcome Metrics

| ID | Resp.1 | Resp.2 | Resp.3 | Resp.4 | Resp.5 | Resp.5 | Resp.6 |
|---|---|---|---|---|---|---|---|
| 100 | 0 | 0 | 0 | 0 | 0 | 0 | 0 |
| 104 | 1 | 0 | 0 | 0 | 0 | 0 | 0 |
| 106 | 1 | 0 | 0 | 0 | 0 | 0 | 0 |
| 110 | 1 | 1 | 1 | 1 | 1 | 1 | 1 |
| 113 | 0 | 0 | 0 | 0 | 0 | 0 | 0 |
| 114 | 0 | 0 | 0 | 0 | 0 | 0 | 0 |
| 117 | 1 | 0 | 0 | 0 | 0 | 0 | 0 |
| 119 | 1 | 0 | 0 | 0 | 1 | 1 | 1 |
| 120 | 1 | 0 | 1 | 1 | 1 | 1 | 1 |
| 122 | 0 | 0 | 0 | 0 | 0 | 0 | 0 |

Because Resp.2 to Resp.6 are conceptually similar, the two outcome measures Resp.1 and Resp.6 were used for further analysis.

Initially, frequency tables of the data from Table 1 and other frequency-based on ANOVA-based analyses were performed, leading to no significant discrimination between responders/non-responders to treatment for any of the possible response variables. This negative result prompted further investigation involving:

a. Recoding of the data into binary format, which resulted in each person being described by a binary vector of length 24;
b. Defining measures of association between these vectors and the outcome from the study, e.g. a distance between the binary vectors and the outcome measures;
c. Development of a search algorithm which maximized the distances between responders and non-responders to treatment.

Certain patterns achieve good results with outcome measures Resp.1 and Resp.6 and could therefore be candidates for further examination. Below are results that illustrate this analytical concept and the construct of possible associations:

TABLE 3

Recoding of Gene Identifiers

| Identifier | Expression | Coded as |
|---|---|---|
| sert | LL | g1LL |
|  | LS | g1LS |
|  | SS | g1SS |
| rs1042173 | TT | g2TT |
|  | TG | g2TG |
|  | GG | g2GG |

TABLE 3-continued

Recoding of Gene Identifiers

| Identifier | Expression | Coded as |
|---|---|---|
| rs1150226 | AA | g3AA |
|  | AG | g3AG |
|  | GG | g3GG |
| rs1176713 | AA | g4AA |
|  | AG | g4AG |
|  | GG | g4GG |
| rs1176719 | AA | g5AA |
|  | AG | g5AG |
|  | GG | g5GG |
| rs17614942 | AA | g6AA |
|  | AC | g6AC |
|  | CC | g6CC |
| rs4938056 | CC | g7CC |
|  | CT | g7CT |
|  | TT | g7TT |
| rs1672717 | AA | g8AA |
|  | AG | g8AG |
|  | GG | g8GG |

Each of the new variables g1LL, g1LS, . . . , g8GG can be zero or one depending on the genotypes in the original data. For example, for subject 100, sert is in position "LS." This will therefore be coded as g1LL=0, g1LS=1, and g1SS=0. As a result, each subject will be represented by a vector with length 24 and binary elements, zero indicating "no expression" and 1 indicating "expression" of each gene position. This way, the generally qualitative information in Table 1 is translated in quantitative information that is suitable for further analyses based on distance and association measures. To illustrate this translation, Table 4 presents the recoded data for the first 10 subjects.

TABLE 4

Recoded Gene Expression Data:

| ID | g1LL | g1LS | g1SS | g2TT | g2TG | g2GG | g3AA | G3AG | g3GG | g4AA | g4AG | g4GG |
|---|---|---|---|---|---|---|---|---|---|---|---|---|
| 100 | 0 | 1 | 0 | 0 | 1 | 0 | 0 | 1 | 0 | 1 | 0 | 0 |
| 104 | 1 | 0 | 0 | 0 | 1 | 0 | 0 | 0 | 1 | 0 | 0 | 1 |
| 106 | 0 | 1 | 0 | 0 | 0 | 1 | 0 | 0 | 1 | 1 | 0 | 0 |
| 110 | 0 | 1 | 0 | 1 | 0 | 0 | 0 | 0 | 1 | 1 | 0 | 0 |
| 113 | 1 | 0 | 0 | 0 | 1 | 0 | 0 | 0 | 1 | 0 | 1 | 0 |
| 114 | 0 | 0 | 1 | 0 | 0 | 1 | 0 | 0 | 1 | 1 | 0 | 0 |
| 117 | 0 | 1 | 0 | 1 | 0 | 0 | 0 | 0 | 1 | 1 | 0 | 0 |
| 119 | 1 | 0 | 0 | 1 | 0 | 0 | 0 | 0 | 1 | 0 | 0 | 1 |
| 120 | 1 | 0 | 0 | 1 | 0 | 0 | 0 | 0 | 1 | 1 | 0 | 0 |
| 122 | 0 | 1 | 0 | 0 | 1 | 0 | 0 | 0 | 1 | 1 | 0 | 0 |
| . | . | . | . | . | . | . | . | . | . | . | . | . |

| ID | g5AA | g5AG | g5GG | g6AA | g6AC | g6CC | g7CC | G7CT | g7TT | g8AA | g8AG | g8GG |
|---|---|---|---|---|---|---|---|---|---|---|---|---|
| 100 | 0 | 0 | 1 | 0 | 0 | 1 | 0 | 1 | 0 | 0 | 1 | 0 |
| 104 | 1 | 0 | 0 | 0 | 0 | 1 | 0 | 1 | 0 | 1 | 0 | 0 |
| 106 | 0 | 0 | 1 | 0 | 0 | 1 | 0 | 1 | 0 | 0 | 1 | 0 |
| 110 | 0 | 0 | 1 | 0 | 0 | 1 | 0 | 0 | 1 | 1 | 0 | 0 |
| 113 | 0 | 0 | 1 | 0 | 0 | 1 | 0 | 1 | 0 | 0 | 0 | 1 |
| 114 | 0 | 0 | 1 | 0 | 0 | 1 | 0 | 1 | 0 | 0 | 1 | 0 |
| 117 | 0 | 0 | 1 | 0 | 0 | 1 | 1 | 0 | 0 | 0 | 0 | 1 |
| 119 | 1 | 0 | 0 | 0 | 0 | 1 | 0 | 1 | 0 | 0 | 1 | 0 |
| 120 | 0 | 1 | 0 | 0 | 0 | 1 | 0 | 0 | 1 | 1 | 0 | 0 |
| 122 | 1 | 0 | 0 | 0 | 0 | 1 | 0 | 0 | 1 | 1 | 0 | 0 |

Association (Distance) Between Gene Expression Combinations and Outcome:

Each combination of gene expressions in Table 4 can be assigned a score related to a gene pattern, depending on the number of genes from the pattern that are present in that combination. For example, if we are looking at the pattern (g1LL, g2GG, g3AG, g7CT), which has length 4, then Subject 100 would have a score of 0+0+1+1=2 because g1LL and g2GG are in position "0" for that subject and the other two gene expressions are in position "1".

It follows that along this pattern (g1LL, g2GG, g3AG, g7CT) each person can have a score ranging from 0 (no matches) to 4 (perfect match). Such a Score can be then associated with non-responder-responder coded as 0 or 1 using one of several methods for association. Here we illustrate this concept using correlations and Chi-square measures of association and the outcome metric Resp. 1. It becomes intuitively clear that a statistically significant association between a gene pattern and the outcome would imply ability to separate treatment responders from non-responders using their genotype.

Search Algorithm and Initial Results:

First, for all patterns with length of up to 4 elements, we compute a score for each subject as described above. For example, when looking at the pattern (g1LL, g2GG, g3AG, g7CT), the score will be computed by the following sequence of commands:

Score=0;
If (g1LL=1) Score=Score+1;
If (g2GG=1) Score=Score+1;
If (g3AG=1) Score=Score+1;
If (g7CT=1) Score=Score+1.

Further, the algorithm runs through all possible patterns and computes the association of each score with the outcome using appropriate measure of association. For example, if we use correlation as a measure of association and the outcome metric Resp. 1, we will find a number of statistically significant associations between the Scores and the outcome.

The best pattern is represented by: g2TT=1; g3AA=1 or g3AG=1; g4AG=1, g8AG=1

The score computed from this pattern using the equations:
Score=0.
if (g2TT eq 1) score=score+1.
if (g3AA eq 1 or g3AG eq 1) score=score+1.
if (g4AG eq 1) score=score+1.
if (g8AG eq 1) score=score+1.
is significantly correlated with the outcome Resp. 1 (r=0.23, p<0.0001) and yields the following association with responders/non responders.

This means that with a person with Score of 0 has a 43% chance of responding to treatment, while a person with Score 3 or 4 (composite result) has over 80% chance responding to treatment (in terms of Resp. 1, which is reduction of drinks/day by two or more). This association is significant, p=0.003. It is, however, evident that if the outcome metric is changed, the strength of these associations will change as well, meaning that different gene patterns would be identified if the outcome metric is changed.

Additional Results:

The outcome measure, i.e., the definition of "responder", was changed to Resp. 6, meaning that a person is a responder to treatment if s/he had 5 or less heavy drinking days in the two months following treatment. This resulted in 33% of the study participants identified as responders (as opposed to 66% of the participants identified as responders by metric Resp. 1). Nevertheless, a number of gene expression patterns were identified that favor response to treatment.

Looking at the overall results, we found that the gene expressions most frequently associated with non-response to treatment are: g1LL=0 (e.g., sert in position LS or SS); g2TT=0 (e.g., rs1042173 in position TG or GG); g3GG=1 (e.g., rs1176713 in position GG); g5AA=1 (e.g., rs1176719 in position AA), and g8GG=1 (e.g., rs1672717 in position GG). This observation yields a score that is significantly associated with either definition of responder (Resp.1 or Resp.6) comprised by these genes and computed as follows:

score=0.
if (g1LS eq 1 or g1SS eq 1) score=score+1.
if (g2TG eq 1 or G2GG eq 1) score=score+1.
if (g3GG eq 1) score=score+1.
if (g5AA eq 1) score=score+1.
if (g8GG eq 1) score=score+1.

The correlations of this Score with Resp.1 and Resp. 6 are r=−0.17 (p=0.004) and r=−0.19 (p=0.001), respectively, i.e. a higher Score favors non-responders. This is also evident from these cross-tables:

TABLE 5

| The best gene pattern associated with Resp.1 | | | | | | |
|---|---|---|---|---|---|---|
| RESPOND | Count Col Pct 0.00 | 1.00 | 2.00 | 3.00 | 4.00 | Row Total |
| SCORE 0 | 29 | 43 | 19 | 5 | | 96 |
| | 52.7 | 36.1 | 24.1 | 18.6 | | 34.2 |
| 1 | 26 | 76 | 60 | 22 | 1 | 185 |
| | 47.3 | 63.9 | 75.9 | 81.5 | 100.0 | 65.8 |
| Column Total | 55 | 119 | 79 | 27 | 1 | 281 |
| | 19.6 | 42.3 | 28.1 | 9.6 | 0.4 | 100.0 |

| | Value | DF | Significance |
|---|---|---|---|
| Chi-Square | 15.68157 | 4 | 0.00348 |

TABLE 6

Association of Score with Resp. 1

| RESP1 | | Count Col Pct 0.00 | 1.00 | 2.00 | 3.00 | 4.00 | Row Total |
|---|---|---|---|---|---|---|---|
| SCORE | 0 | 2 | 11 | 23 | 49 | 11 | 96 |
| | | 16.7 | 24.4 | 29.1 | 39.8 | 50.0 | 34.2 |
| | 1 | 10 | 34 | 56 | 74 | 11 | 185 |
| | | 83.3 | 75.6 | 70.9 | 60.2 | 50.0 | 65.8 |
| Column Total | | 12 | 45 | 79 | 123 | 22 | 281 |
| | | 4.3 | 16.0 | 28.1 | 43.8 | 7.4 | 100.0 |

| | Value | DF | Significance |
|---|---|---|---|
| Chi-Square Pearson | 8.63234 | 4 | 0.07098 |

TABLE 7

Association of Score with Resp. 6:

| RESP6 | | Count Col Pct 0.00 | 1.00 | 2.00 | 3.00 | 4.00 | Row Total |
|---|---|---|---|---|---|---|---|
| SCORE | 0 | 4 | 26 | 50 | 92 | 16 | 188 |
| | | 33.3 | 57.8 | 63.3 | 74.8 | 72.7 | 66.9 |
| | 1 | 8 | 19 | 29 | 31 | 6 | 93 |
| | | 66.7 | 42.2 | 36.7 | 25.2 | 27.3 | 33.1 |
| Column Total | | 12 | 45 | 79 | 123 | 22 | 281 |
| | | 4.3 | 16.0 | 28.1 | 43.8 | 7.4 | 100.0 |

| | Value | DF | Significance |
|---|---|---|---|
| Chi-Square Pearson | 12.06335 | 4 | 0.01689 |

According to Table 6, a person with a Score of 0 (composite result) has over 80% chance to be a responder with respect to measure Resp.1 (i.e. to reduce his/her drinking by 2 or more drinks/day). This chance goes down to 50% with a score of 4 (composite score/result). According to Table 7, a person with a Score of 0 has a 67% chance to be a responder with respect to measure Resp.6 (i.e., to reduce his/her drinking to below 5 heavy drinking days in two months). This chance goes down to 27% with a score of 4.

A simple final recoding of Score (0 1=2) (2=1) (3 4=0) yields orderly cross tables showing significant associations between the increasing levels of this variable and the likelihood for responding to treatment. For example, Table 8 presents the likelihood for Resp. 6=1 increasing from 25 to nearly 50% across the three categories defined by score.

TABLE 8

Final Association between Genotype and Response to treatment (defined by Resp. 6):

| RESP6 | | Count Col Pct 0.00 | 1.00 | 2.00 | Row Total |
|---|---|---|---|---|---|
| SCORE | 0 | 108 | 50 | 30 | 188 |
| | | 74.5 | 63.3 | 52.6 | 66.9 |
| | 1 | 37 | 29 | 27 | 93 |
| | | 25.5 | 36.7 | 47.4 | 33.1 |
| Column Total | | 145 | 79 | 57 | 281 |
| | | 51.6 | 28.1 | 20.3 | 100.0 |

| | Value | DF | Significance |
|---|---|---|---|
| Chi-Square | 9.47073 | 2 | 0.00878 |

Example 12-Additional Analysis of Gene Patterns Related to Response to Ondansetron Treatment Using the same data as was used in Example 11, further epistatic analysis among SNPs from serotonin (SERT), 5HT-3A, and 5HT-3B reveal that significant epistatic effect exists among the three genes in affecting response to ondesetron treatment as measured by drinks/drinking day. Of these significant SNP combinations, the SNP combinations of 5HTTLPR-rs1176719-rs1672717-rs2276307 and 5HTTLPR-rs1042173-rs10160548-rs1176746-rs12270070 appear to be the best to predict treatment response (see Table 1 for details).

TABLE 1

Comparison of Best Multigene Models, Prediction Accuracies, Cross-Validation Consistencies, and P Values Identified by GMDR for the association with drinks/drinking day

| No. of Loci | Best SNP combination under Additive Genetic models | Prediction Accuracy | Cross Validation Consistency (p value from sign test) | P[a] |
|---|---|---|---|---|
| 1 | rs1672717[4](HTR3B) | 0.6053 | 7 (0.172) | 0.029 |
| 2 | rs1176719[2] (HTR3A)-rs1672717[4] | 0.699 | 10 (0.001) | <0.0001 |
| 3 | rs1176719[2]- rs1672717[4]-rs4938056(HTR3B) and | 0.6974 | 10 (0.001) | <0.0001 |
| | 5HTTLPR[1](SERT)-rs1176719[2]-rs4938056 | 0.6867 | 9 (0.011) | 0.002 |

TABLE 1-continued

Comparison of Best Multigene Models, Prediction Accuracies, Cross-Validation Consistencies, and P Values Identified by GMDR for the association with drinks/drinking day

| No. of Loci | Best SNP combination under Additive Genetic models | Prediction Accuracy | Cross Validation Consistency (p value from sign test) | $P^a$ |
|---|---|---|---|---|
| 4 | 5HTTLPR[1]- rs1176719[2]-rs1672717[4] (HTR3B)-rs2276307[5](HTR3B) | 0.702 | 10 (0.001) | <0.0001 |
| 5 | 5HTTLPR[1]-rs1042173[5](SERT)-rs10160548[6](HTR3A)-rs1176746[7](HTR3B)-rs12270070[8](HTR3B) | 0.6671 | 9 (0.011) | 0.002 |

$P^a$ values from permutation test
[1] LL genotype.
[2] AG/GG genotypes.
[3] AA genotype.
[4] GG/AG genotypes.
[5] TT genotype.
[6] GT/GG genotypes.
[7] GA/GG genotypes.
[8] GG genotypes.

Example 13—Ondansetron Response by Genotype: Alcohol Dependent Individuals that are T+ Carriers, in Particular Those that have the TG Genotype, of the 3'-UTR Respond Differentially to Ondansetron Versus Placebo Treatment Studies on 283 subjects that were randomized and evaluated according to the 5'-HTTLPR (LL/LS/SS) and 3'-UTR (TT/TG/SS) combination were undertaken in combination with an analysis of the pattern of response to treatment with ondansetron, in particular, whether ondansetron was more efficacious than placebo according to genotype.

The polymorphism in the untranslated region of the serotonin transporter gene (i.e., 3'UTR of SLC6A4) has been identified and determined to modulate mRNA expression level of the serotonin transporter and is associated with excessive drinking (Seneviratne C. et al. Alcohol Clinical and Experimental Research 33(2); 332-339, 2009). Specifically, allelic differences at the rs1042173 SNP showed a significant difference in the intensity of drinking. In expression studies, the T-allele was associated with lower mRNA expression whilst the G-allele was associated with higher levels of mRNA expression. Possession of the T-allele also was associated with greater drinking intensity. Furthermore, it would appear from unpublished data that the TT genotype compared with the Gx (TG/GG) genotype was associated with the highest drinking levels. In an unpublished analysis of data from 32 non-treatment seeking alcoholics, it was observed that the TT allele compared with the Gx is associated with increased subjective ("Urge to drink"— F=5.58, p=0.021; "Crave for a drink"— F=5.01, p=0.028) and physiological craving for alcohol.

The 5'HTTLR and 3'-UTR regions of SLC6A4 are not linked. Therefore, it would be surprising and unexpected for there to be any interaction between their polymorphisms. And certainly, even more so for there to be an interaction between these interactions that affect the consumption of alcohol or for these alleles to predict the effect of any putative treatment medication (including 5-HT3 antagonists) in the treatment of alcoholism.

It is, therefore, also unexpected that from unpublished data collected from a phase II study in alcohol dependent patients that there is a pharmacological interaction between the T-allele and 5'-HTTLPR genotypes. In particular, there appears to be an unexpected large therapeutic effect to improve drinking outcomes when ondansetron is provided to those with LL genotype who also have the TT genotype. Furthermore, and also unexpected, possession of the TG genotype adds to the therapeutic effect of ondansetron on all 5'HTTLPR genotypes (i.e., LL/LS/GG) (responders to treatment can be defined, for example, as those for whom the direction of effect is better for ondansetron compared with placebo on one, two, three or four measures of response: 1) percentage of heavy drinking days (PHDD); 2) Drinks/Drinking Day (DDD); 3) Percentage of Days Abstinent (PDA); and/or 4 Percentage of patients with no heavy drinking). From the data, it was determined that LL/TT, LL/TG, LL/GG, LS/TG, and SS/TG genotypes respond to ondansetron treatment.

The TT and TG genotype groups can be summarized as T carriers. FIGS. 11A-11C provide data demonstrating that LL/T+ carriers have an effect on percent heavy drinking days, drinks/drinking days and percent days abstinent, while FIG. 12 depicts data regarding patients with less than 3 (1/month) heavy drinking days ("safe drinking") during 12 weeks. In conclusion, LL/T+ carriers (e.g., LL/TT and LL/TG) are responsive to treatment.

Example 14-Additional Analysis of Gene Patterns Related to Response to Ondansetron Treatment Using the same data as was used in Example 11, further epistatic analysis among SNPs from serotonin (SERT), 5HT-3A, and 5HT-3B reveal that significant epistatic effect exists among the three genes in affecting response to ondesetron treatment as measured by drinks/drinking day (DDD), drinks/day (DD), percentage heavy drinking days (PHDD), and percentage of days abstinent (PDA).

Part I:

TABLE 1

Any one or two or three or four of 5-HTTLPR (LL) or RS1042173 (TT) or RS1150226 (AG) or RS17614942 (AC)

| | Estimate | StdErr | P-value |
|---|---|---|---|
| 1. One or Two or Three or Four | | | |
| 5-HTTLPR (LL): OND (n = 49) vs. Placebo (n = 44) | −1.41 | 0.59 | 0.017 |
| RS1042173 (TT): OND (n = 42) vs. Placebo (n = 48) | −0.86 | 0.61 | 0.156 |
| RS1150226 (AG): OND (n = 20) vs. Placebo (n = 24) | −1.81 | 0.87 | 0.036 |
| RS17614942 (AC): OND (n = 17) vs. Placebo (n = 19) | −2.73 | 0.95 | 0.004 |
| LL + TT: OND (n = 22) vs. Placebo (n = 23) | −2.08 | 0.85 | 0.014 |
| LL + AG: OND (n = 8) vs. Placebo (n = 9) | −3.06 | 1.42 | 0.031 |
| LL + AC: OND (n = 7) vs. Placebo (n = 8) | −4.24 | 1.48 | 0.004 |
| TT + AG: OND (n = 9) vs. Placebo (n = 6) | −2.00 | 1.53 | 0.191 |
| TT + AC: OND (n = 9) vs. Placebo (n = 7) | −3.37 | 1.44 | 0.019 |
| AG + AC: OND (n = 14) vs. Placebo (n = 16) | −2.42 | 1.05 | 0.021 |
| LL + TT + AG: OND (n = 5) vs. Placebo (n = 3) | −3.92 | 2.13 | 0.066 |

TABLE 1-continued

Any one or two or three or four of 5-HTTLPR (LL) or
RS1042173 (TT) or RS1150226 (AG) or RS17614942 (AC)

| | Estimate | StdErr | P-value |
|---|---|---|---|
| LL + TT + AC:<br>OND (n = 6) vs. Placebo (n = 4) | −4.25 | 1.85 | 0.021 |
| LL + AG + AC:<br>OND (n = 5) vs. Placebo (n = 7) | −4.09 | 1.69 | 0.016 |
| TT + AG + AC:<br>OND (n = 7) vs. Placebo (n = 5) | −2.24 | 1.71 | 0.190 |
| LL + TT + AG +AC:<br>OND (n = 4) vs. Placebo (n = 3) | −4.05 | 2.22 | 0.068 |
| 2. Any of One or Two | | | |
| LL or TT:<br>OND (n = 67) vs. Placebo (n = 68) | −0.87 | 0.49 | 0.078 |
| LL or AG:<br>OND (n = 59) vs. Placebo (n = 58) | −1.37 | 0.52 | 0.009 |
| LL or AC:<br>OND (n = 57) vs. Placebo (n = 54) | −1.53 | 0.54 | 0.005 |
| TT or AG:<br>OND (n = 53) vs. Placebo (n = 66) | −1.02 | 0.53 | 0.054 |
| TT or AC:<br>OND (n = 50) vs. Placebo (n = 60) | −1.07 | 0.55 | 0.052 |
| AG or AC:<br>OND (n = 23) vs. Placebo (n = 27) | −2.12 | 0.81 | 0.009 |
| 3. Any of One, Two, or Three | | | |
| LL or TT or AG:<br>OND (n = 75) vs. Placebo (n = 80) | −0.94 | 0.46 | 0.041 |
| LL or TT or AC:<br>OND (n = 74) vs. Placebo (n = 76) | −0.97 | 0.47 | 0.038 |
| LL or AG or AC:<br>OND (n = 60) vs. Placebo (60) | −1.43 | 0.52 | 0.006 |
| TT or AG or AC:<br>OND (n = 54) vs. Placebo (n = 67) | −0.99 | 0.53 | 0.059 |
| 4. Any of One, Two, Three, or Four<br>(N = 157) | | | |
| LL or TT or AG or AC:<br>OND (n = 76) vs. Placebo (n = 81) | −0.93 | 0.46 | 0.042 |

Table 1 Summary:

1): Except RS1042173, if patients had either 5-HTTLPR (LL) or RS1150226 (AG) or RS17614942 (AC), patients who received OND had at least 1.4 drinks per drinking days (DDD) reductions compared to those who received placebo. If patients had either two of the four gene variants, there were at least 2 DDD reductions with OND. If patients had either three of the four gene variants, there were more than 2 DDD reductions with OND. If patients had all four gene variants, there were more than 4 DDD reductions with OND. The DDD reductions seemed to increase while number of 'positive' gene variants increase.

2): If patients had either one or two of the four gene variants, there were about 0.9 to 2.1 DDD reductions with OND.

3): If patients had either one or two or three of the four gene variants, there were about 0.9 to 1.4 DDD reductions with OND.

4): If patients had either one or two or three or four of the four gene variants, there were at least 0.9 DDD reductions with OND.

Therefore, there were 157 out of 273 (56%) subjects in this study sample who had either one or two or three or four of the four gene variants seemed to respond to OND treatment.

TABLE 2

Any one or two or three or four of 5-HTTLPR (LL) or
RS1042173 (TT) or RS1176719 (AA) or RS17614942 (AC)

| | Estimate | StdErr | P-value |
|---|---|---|---|
| 1. One or Two or Three or Four | | | |
| 5-HTTLPR (LL):<br>OND (n = 49) vs. Placebo (n = 44) | −1.41 | 0.59 | 0.017 |
| RS1042173 (TT):<br>OND (n = 42) vs. Placebo (n = 48) | −0.86 | 0.61 | 0.156 |
| RS1176719 (AA):<br>OND (n = 11) vs. Placebo (n = 11) | −3.27 | 1.26 | 0.010 |
| RS17614942 (AC):<br>OND (n = 17) vs. Placebo (n = 19) | −2.73 | 0.95 | 0.004 |
| LL + TT:<br>OND (n = 22) vs. Placebo (n = 23) | −2.08 | 0.85 | 0.014 |
| LL + AA:<br>OND (n = 7) vs. Placebo (n = 8) | −5.22 | 1.82 | 0.004 |
| LL + AC:<br>OND (n = 7) vs. Placebo (n = 8) | −4.24 | 1.48 | 0.004 |
| TT + AA:<br>OND (n = 4) vs. Placebo (n = 5) | −7.12 | 2.10 | 0.0007 |
| TT + AC:<br>OND (n = 9) vs. Placebo (n = 7) | −3.37 | 1.44 | 0.019 |
| AA + AC:<br>OND (n = 0) vs. Placebo (n = 2) | NA | NA | NA |
| LL + TT + AA:<br>OND (n = 4) vs. Placebo (n = 3) | −8.50 | 2.32 | 0.0002 |
| LL + TT + AC:<br>OND (n = 6) vs. Placebo (n = 4) | −4.25 | 1.85 | 0.021 |
| LL + AA + AC:<br>OND (n = 7) vs. Placebo (n = 3) | −5.96 | 2.01 | 0.003 |
| TT + AA + AC:<br>OND (n = 0) vs. Placebo (n = 1) | NA | NA | NA |
| LL + TT + AA + AC:<br>OND (n = 0) vs. Placebo (n = 1) | NA | NA | NA |
| 2. Any of One or Two | | | |
| LL or TT:<br>OND (n = 67) vs. Placebo (n = 68) | −0.87 | 0.49 | 0.078 |
| LL or AA:<br>OND (n = 0) vs. Placebo (n = 0) | NA | NA | NA |
| LL or AC:<br>OND (n = 57) vs. Placebo (n = 54) | −1.53 | 0.54 | 0.005 |
| TT or AA:<br>OND (n = 0) vs. Placebo (n = 0) | NA | NA | NA |
| TT or AC:<br>OND (n = 50) vs. Placebo (n = 60) | −1.07 | 0.55 | 0.052 |
| AA or AC:<br>OND (n = 28) vs. Placebo (n = 28) | −2.83 | 0.76 | 0.0002 |
| 3. Any of One, Two, or Three | | | |
| LL or TT or AA:<br>OND (n = 70) vs. Placebo (n = 73) | −0.99 | 0.48 | 0.039 |
| LL or TT or AC:<br>OND (n = 74) vs. Placebo (n = 76) | −0.97 | 0.47 | 0.038 |
| LL or AA or AC:<br>OND (n = 60) vs. Placebo (n = 60) | −1.55 | 0.52 | 0.003 |
| TT or AA or AC:<br>OND (n = 56) vs. Placebo (n = 66) | −1.08 | 0.52 | 0.039 |
| 4. Any of One, Two, Three, or Four<br>(N = 166) | | | |
| LL or TT or AA or AC:<br>OND (n = 57) vs. Placebo (n = 59) | −1.02 | 0.46 | 0.026 |

Table 2 Summary: If patients had either one or two or three or four of 5-HTTLPR (LL) or RS1042173 (TT) or RS1176719 (AA) or RS17614942 (AC), they are likely to respond to OND treatment.

Part II:

TABLE 3

Any one or two or three of 5-HTTLPR (LL) or RS1042173 (TT) or RS1150226 (AG)

| | Estimate | StdErr | P-value |
|---|---|---|---|
| 1. One or Two or Three | | | |
| 5-HTTLPR (LL): | −1.41 | 0.59 | 0.017 |
| OND (n = 49) vs. Placebo (n = 44) | | | |
| RS1042173 (TT): | −0.86 | 0.61 | 0.156 |
| OND (n = 42) vs. Placebo (n = 48) | | | |
| RS1150226 (AG): | −1.81 | 0.87 | 0.036 |
| OND (n = 20) vs. Placebo (n = 24) | | | |
| LL + TT: | −2.08 | 0.85 | 0.014 |
| OND (n = C2) vs. Placebo (n = 23) | | | |
| LL + AG: | −3.06 | 1.42 | 0.031 |
| OND (n = 8) vs. Placebo (n = 9) | | | |
| TT + AG: | −2.00 | 1.53 | 0.191 |
| OND (n = 9) vs. Placebo (n = 6) | | | |
| LL + TT + AG: | −3.92 | 2.13 | 0.066 |
| OND (n = 5) vs. Placebo (n = 3) | | | |
| 2. Any of One or Two | | | |
| LL or TT: | −0.87 | 0.49 | 0.078 |
| OND (n = 67) vs. Placebo (n = 68) | | | |
| LL or AG: | −1.37 | 0.52 | 0.009 |
| OND (n = 59) vs. Placebo (n = 58) | | | |
| TT or AG: | −1.02 | 0.53 | 0.054 |
| OND (n = 53) vs. Placebo (n = 66) | | | |
| 3. Any of One, Two, or Three (N = 155) | | | |
| LL or TT or AG: | −0.94 | 0.46 | 0.041 |
| OND (n = 75) vs. Placebo (n = 80) | | | |

TABLE 4

Any one or two or three of 5-HTTLPR (LL) or RS1042173 (TT) or RS17614942 (AC)

| | Estimate | StdErr | P-value |
|---|---|---|---|
| 1. One or Two or Three | | | |
| 5-HTTLPR (LL): | −1.41 | 0.59 | 0.017 |
| OND (n = 49) vs. Placebo (n = 44) | | | |
| RS1042173 (TT): | −0.86 | 0.61 | 0.156 |
| OND (n = 42) vs. Placebo (n = 48) | | | |
| RS17614942 (AC): | −2.73 | 0.95 | 0.004 |
| OND (n = 17) vs. Placebo (n = 19) | | | |
| LL + TT: | −2.08 | 0.85 | 0.014 |
| OND (n = 22) vs. Placebo (n = 23) | | | |
| LL + AC: | −4.24 | 1.48 | 0.004 |
| OND (n = 7) vs. Placebo (n = 8) | | | |
| TT + AC: | −3.37 | 1.44 | 0.019 |
| OND (n = 9) vs. Placebo (n = 7) | | | |
| LL + TT + AC: | −4.25 | 1.85 | 0.021 |
| OND (n = 6) vs. Placebo (n = 4) | | | |
| 2. Any of One or Two | | | |
| LL or TT: | −0.87 | 0.49 | 0.078 |
| OND (n = 67) vs. Placebo (n = 68) | | | |
| LL or AC: | −1.53 | 0.54 | 0.005 |
| OND (n = 57) vs. Placebo (n = 54) | | | |
| TT or AC: | −1.07 | 0.55 | 0.052 |
| OND (n = 50) vs. Placebo (n = 60) | | | |
| 3. Any of One, Two, or Three (N = 150) | | | |
| LL or TT or AC: | −0.97 | 0.47 | 0.038 |
| OND (n = 74) vs. Placebo (n = 76) | | | |

TABLE 5

Any one or two or three of RS1042173 (TT) or RS1150226 (AG) or RS17614942 (AC)

| | Estimate | StdErr | P-value |
|---|---|---|---|
| 1. One or Two or Three | | | |
| RS1042173 (TT): | −0.86 | 0.61 | 0.156 |
| OND (n = 42) vs. Placebo (n = 48) | | | |
| RS1150226 (AG): | −1.81 | 0.87 | 0.036 |
| OND (n = 20) vs. Placebo (n = 24) | | | |
| RS17614942 (AC): | −2.73 | 0.95 | 0.004 |
| OND (n = 17) vs. Placebo (n = 19) | | | |
| TT + AG: | −2.00 | 1.53 | 0.191 |
| OND (n = 9) vs. Placebo (n = 6) | | | |
| TT + AC: | −3.37 | 1.44 | 0.019 |
| OND (n = 9) vs. Placebo (n = 7) | | | |
| AG + AC: | −2.42 | 1.05 | 0.021 |
| OND (n = 14) vs. Placebo (n = 16) | | | |
| TT + AG + AC: | −2.24 | 1.71 | 0.190 |
| OND (n = 7) vs. Placebo (n = 5) | | | |
| 2. Any of One or Two | | | |
| TT or AG: | −1.02 | 0.53 | 0.054 |
| OND (n = 53) vs. Placebo (n = 66) | | | |
| TT or AC: | −1.07 | 0.55 | 0.052 |
| OND (n = 50) vs. Placebo (n = 60) | | | |
| AG or AC: | −2.12 | 0.81 | 0.009 |
| OND (n = 23) vs. Placebo (n = 27) | | | |
| 3. Any of One, Two, or Three (N = 121) | | | |
| TT or AG or AC: | −0.99 | 0.53 | 0.059 |
| OND (n = 54) vs. Placebo (n = 67) | | | |

TABLE 6

Any one or two or three of 5-HTTLPR (LL) or RS1150226 (AG) or RS17614942 (AC)

| | Estimate | StdErr | P-value |
|---|---|---|---|
| 1. One or Two or Three | | | |
| 5-HTTLPR (LL): | −1.41 | 0.59 | 0.017 |
| OND (n = 49) vs. Placebo (n = 44) | | | |
| RS1150226 (AG): | −1.81 | 0.87 | 0.036 |
| OND (n = 20) vs. Placebo (n = 24) | | | |
| RS17614942 (AC): | −2.73 | 0.95 | 0.004 |
| OND (n = 17) vs. Placebo (n = 19) | | | |
| LL + AG: | −3.06 | 1.42 | 0.031 |
| OND (n = 8) vs. Placebo (n = 9) | | | |
| LL + AC: | −4.24 | 1.48 | 0.004 |
| OND (n = 7) vs. Placebo (n = 8) | | | |
| AG + AC: | −2.42 | 1.05 | 0.021 |
| OND (n = 14) vs. Placebo (n = 16) | | | |
| LL + AG + AC: | −4.09 | 1.69 | 0.016 |
| OND (n = 5) vs. Placebo (n = 7) | | | |
| 2. Any of One or Two | | | |
| LL or AG: | −1.37 | 0.52 | 0.009 |
| OND (n = 59) vs. Placebo (58) | | | |
| LL or AC: | −1.53 | 0.54 | 0.005 |
| OND (n = 57) vs. Placebo (54) | | | |
| AG or AC: | −2.12 | 0.81 | 0.009 |
| OND (n = 23) vs. Placebo (27) | | | |
| 3. Any of One, Two, or Three (N = 120) | | | |
| LL or AG or AC: | −1.43 | 0.52 | 0.006 |
| OND (n = 60) vs. Placebo (60) | | | |

SUMMARY

1) If patients had any one of the three gene variants (5-HTTLPR [LL], RS1150226[AG], or RS17614942 [AC]), patients who received OND had at least 1.4 DDD reduction compared to those patients who received placebo. If patients had any two of the three gene variants, patients who received OND had at least 2.4 DDD reduction compared to those who received placebo. If patients had the three gene variants, patients who received OND had at least 4 DDD reduction compared to those who received placebo. The DDD reductions seemed to increase while the number of 'positive' gene variants increases.

2) If patients had one or two of the three gene variants, patients who received OND had about 1.4 DDD reductions compared to those who received placebo. 3): If patients had one or two or three of the three gene variants, patients who received OND had at least 1.4 DDD reductions compared to those who received placebo.

This sub-sample, with 120 patients, had the strongest among three gene variants combinations (All p-values<0.05).

Patients who had either one or two or three of these three gene variants seemed to respond to Ondansetron treatment.

TABLE 7

Any one or two or three of 5-HTTLPR (LL) or RS1042173 (TT) or RS1176713 (GG)

|  | Estimate | StdErr | P-value |
|---|---|---|---|
| 1. One or Two or Three |  |  |  |
| 5-HTTLPR (LL): | −1.41 | 0.59 | 0.017 |
| OND (n = 49) vs. Placebo (n-44) |  |  |  |
| RS1042173 (TT): | −0.86 | 0.61 | 0.156 |
| OND (n = 42) vs. Placebo (n = 48) |  |  |  |
| RS1176713 (GG): | −3.92 | 1.57 | 0.013 |
| OND (n = 6) vs. Placebo (n = 9) |  |  |  |
| LL + TT: | −2.08 | 0.85 | 0.014 |
| OND (n = 22) vs. Placebo (n = 23) |  |  |  |
| LL + GG: | −4.48 | 1.98 | 0.024 |
| OND (n = 5) vs. Placebo (n = 4) |  |  |  |
| TT + GG: | −6.42 | 2.41 | 0.008 |
| OND (n = 3) vs. Placebo (n = 4) |  |  |  |
| LL + TT + GG: | −7.65 | 2.55 | 0.003 |
| OND (n = 3) vs. Placebo (n = 3) |  |  |  |
| 2. Any of One or Two |  |  |  |
| LL or TT: | −0.87 | 0.49 | 0.078 |
| OND (n = 67) vs. Placebo (n = 68) |  |  |  |
| LL or GG: | −1.60 | 0.58 | 0.006 |
| OND (n = 47) vs. Placebo (n = 48) |  |  |  |
| IT or GG: | −1.02 | 0.59 | 0.082 |
| OND (n = 45) vs. Placebo (n = 53) |  |  |  |
| 3. Any of One. Two, or Three (N = 139) |  |  |  |
| LL or TT or GG: | −0.94 | 0.46 | 0.041 |
| OND (n = 67) vs. Placebo (n = 72) |  |  |  |

Summary: In this section II the first four tables were really sub-sample of the four gene variants described in the section I (5-HTTLPR (LL) or RS1042173 (TT) or RS1150226 (AG) or RS17614942 (AC)).

In table 7, except RS1042173 (TT), if patients had either 5-HTTLPR (LL) or RS1176713 (GG), they had at least 1.4 DDD reductions with OND. If patients had any two of the three gene variants, they had at least 2 DDD reductions with OND. If patients had the three gene variants, they had at least 7 DDD reductions with OND. If patients had one or two of the three gene variants, they had about 0.9 to 1.6 DDD reductions with OND. If patients had one, or two or three of the three gene variants, they had at least 0.9 DDD reductions with OND. The sample size was 139.

Part III:

TABLE 8

Any one or two or three of 5-HTTLPR (LL) or RS1042173 (TT) or RS1176719 (AA)

|  | Estimate | StdErr | P-value |
|---|---|---|---|
| 1. One or Two or Three |  |  |  |
| 5-HTTLPR (LL): | −1.41 | 0.59 | 0.017 |
| OND (n = 49) vs. Placebo (n = 44) |  |  |  |
| RS1042173 (TT): | −0.86 | 0.61 | 0.156 |
| OND (n = 42) vs. Placebo (n = 48) |  |  |  |
| RS1176719 (AA): | −3.27 | 1.26 | 0.010 |
| OND (n = 11) vs. Placebo (n = 11) |  |  |  |
| LL + TT: | −2.08 | 0.85 | 0.014 |
| OND (n = 22) vs. Placebo (n = 23) |  |  |  |
| LL + AA: | −5.22 | 1.82 | 0.004 |
| OND (n = 7) vs. Placebo (n = 8) |  |  |  |
| TT + AA: | −7.12 | 2.10 | 0.0007 |
| OND (n = 4) vs. Placebo (n = 5) |  |  |  |
| LL + TT + AA: | −8.50 | 2.32 | 0.0002 |
| OND (n = 4) vs. Placebo (n = 3) |  |  |  |
| 2. Any of One or Two |  |  |  |
| LL or TT: | −0.87 | 0.49 | 0.078 |
| OND (n = 67) vs. Placebo (n = 68) |  |  |  |
| LL or AA: | NA | NA | NA |
| OND (n = 0) vs. Placebo (n = 0) |  |  |  |
| TT or AA: | NA | NA | NA |
| OND (n = 0) vs. Placebo (n = 0) |  |  |  |
| 3. Any of One,Two, or Three (N = 143) |  |  |  |
| LL or TT or AA: | −0.99 | 0.48 | 0.039 |
| OND (n = 70) vs. Placebo (n = 73) |  |  |  |

TABLE 9

Any one or two or three of 5-HTTLPR (LL) or RS1176719 (AA) or RS17614942 (AC)

|  | Estimate | StdErr | P-value |
|---|---|---|---|
| 1. One or Two or Three |  |  |  |
| 5-HTTLPR (LL): | −1.41 | 0.59 | 0.017 |
| OND (n = 49) vs. Placebo (n = 44) |  |  |  |
| RS1176719 (AA): | −3.27 | 1.26 | 0.001 |
| OND (n = 11) vs. Placebo (n = 11) |  |  |  |
| RS17614942 (AC): | −2.73 | 0.95 | 0.004 |
| OND (n = 17) vs. Placebo (n = 19) |  |  |  |
| LL + AA: | −5.22 | 1.82 | 0.004 |
| OND (n = 7) vs. Placebo (n = 4) |  |  |  |
| LL + AC: | −4.24 | 1.48 | 0.004 |
| OND (n = 7) vs. Placebo (n = 8) |  |  |  |
| AA + AC: | NA | NA | NA |
| OND (n = 0) vs. Placebo (n = 2) |  |  |  |
| LL + AA + AC: | −5.96 | 2.01 | 0.003 |
| OND (n = 7) vs. Placebo (n = 3) |  |  |  |
| 2. Any of One or Two |  |  |  |
| LL or AA: | NA | NA | NA |
| OND (n = 0) vs. Placebo (n = 0) |  |  |  |
| LL or AC: | −1.53 | 0.54 | 0.005 |
| OND (n = 57) vs. Placebo (n = 54) |  |  |  |
| AA or AC: | −2.83 | 0.76 | 0.0002 |
| OND (n = 28) vs. Placebo (n = 28) |  |  |  |
| 3. Any of One, Two, or Three (N = 120) |  |  |  |
| LL or AA or AC: | −1.55 | 0.52 | 0.003 |
| OND (n = 60) vs. Placebo (n = 60) |  |  |  |

TABLE 10

Any one or two or three of RS1042173 (TT)
or RS1176719 (AA) or RS17614942 (AC)

| | Estimate | StdErr | P-value |
|---|---|---|---|
| 1. One or Two or Three | | | |
| RS1042173 (TT): | −0.86 | 0.61 | 0.156 |
| OND (n = 42) vs. Placebo (n = 48) | | | |
| RS1176719 (AA): | −3.27 | 1.26 | 0.010 |
| OND (n = 11) vs. Placebo (n = 11) | | | |
| RS17614942 (AC): | −2.73 | 0.95 | 0.004 |
| OND (n = 17) vs. Placebo (n = 19) | | | |
| TT + AA: | −7.12 | 2.10 | 0.0007 |
| OND (n = 4) vs. Placebo (n = 5) | | | |
| TT + AC: | −3.37 | 1.44 | 0.019 |
| OND (n = 9) vs. Placebo (n = 7) | | | |
| AA + AC: | NA | NA | NA |
| OND (n = 0) vs. Placebo (n = 2) | | | |
| TT + AA + AC: | NA | NA | NA |
| OND (n = 0) vs. Placebo (n = 1) | | | |
| 2. Any of One or Two | | | |
| TT or AA: | NA | NA | NA |
| OND (n = 0) vs. Placebo (n = 0) | | | |
| TT or AC: | −1.07 | 0.55 | 0.052 |
| OND (n = 50) vs. Placebo (n = 60) | | | |
| AA or AC: | −2.83 | 0.76 | 0.0002 |
| OND (n = 28) vs. Placebo (n = 28) | | | |
| 3. Any of One, Two, or Three (N = 122) | | | |
| TT or AA or AC: | −1.08 | 0.52 | 0.039 |
| OND (n = 56) vs. Placebo (n = 66) | | | |

TABLE 11

Any one or two or three of 5-HTTLPR (LL)
or RS1176713 (GG) or RS17614942 (AC)

| | Estimate | StdErr | P-value |
|---|---|---|---|
| 1. One or Two or Three | | | |
| 5-HTTLPR (LL): | −1.41 | 0.59 | 0.017 |
| OND (n = 49) vs. Placebo (n = 44) | | | |
| RS1176713 (GG): | −3.92 | 1.57 | 0.013 |
| OND (n = 6) vs. Placebo (n = 9) | | | |
| RS17614942 (AC): | −2.73 | 0.95 | 0.004 |
| OND (n = 17) vs. Placebo (n = 19) | | | |
| LL + GG: | −4.48 | 1.98 | 0.024 |
| OND (n = 5) vs. Placebo (n = 4) | | | |
| LL + AC: | −4.24 | 1.48 | 0.004 |
| OND (n = 7) vs. Placebo (n = 8) | | | |
| GG + AC: | NA | NA | NA |
| OND (n = 0) vs. Placebo (n = 2) | | | |
| LL + GG + AC: | NA | NA | NA |
| OND (n = 0) vs. Placebo (n = 1) | | | |
| 2. Any of One or Two | | | |
| LL or GG: | −1.60 | 0.58 | 0.006 |
| OND (n = 47) vs. Placebo (48) | | | |
| LL or AC: | −1.53 | 0.54 | 0.005 |
| OND (n = 57) vs. Placebo (54) | | | |
| GG or AC: | −3.08 | 0.82 | 0.0002 |
| OND (n = 23) vs. Placebo (26) | | | |
| 3. Any of One, Two, or Three (N = 115) | | | |
| LL or GG or AC: | −1.57 | 0.53 | 0.003 |
| OND (n = 57) vs. Placebo (58) | | | |

TABLE 12

Any one or two or three of RS1042173 (TT)
or RS1150226 (AG) or RS1176713 (GG)

| | Estimate | StdErr | P-value |
|---|---|---|---|
| 1. One or Two or Three | | | |
| RS1042173 (TT): | −0.86 | 0.61 | 0.156 |
| OND (n = 42) vs. Placebo (n = 48) | | | |
| RS1150226 (AG): | −1.81 | 0.87 | 0.036 |
| OND (n = 20) vs. Placebo (n = 24) | | | |
| RS1176713 (GG): | −3.92 | 1.57 | 0.013 |
| OND (n = 6) vs. Placebo (n = 9) | | | |
| TT + AG: | −2.00 | 1.53 | 0.191 |
| OND (n = 9) vs. Placebo (n = 6) | | | |
| TT + GG: | −6.42 | 2.41 | 0.008 |
| OND (n = 3) vs. Placebo (n = 4) | | | |
| AG + GG: | NA | NA | NA |
| OND (n = 0) vs. Placebo (n = 0) | | | |
| TT + AG + GG: | NA | NA | NA |
| OND (n = 0) vs. Placebo (n = 0) | | | |
| 2. Any of One or Two | | | |
| TT or AG: | −1.02 | 0.53 | 0.054 |
| OND (n = 53) vs. Placebo (n = 66) | | | |
| TT or GG: | −1.02 | 0.59 | 0.082 |
| OND (n = 45) vs. Placebo (n = 53) | | | |
| AG or GG: | −2.43 | 0.75 | 0.001 |
| OND (n = 26) vs. Placebo (n = 33) | | | |
| 3. Any of One, Two or Three (N = 127) | | | |
| TT or AG or GG: | −1.12 | 0.51 | 0.030 |
| OND (n = 56) vs. Placebo (n = 71) | | | |

TABLE 13

Any one or two or three of RS1042173 (TT)
or RS1176713 (GG) or RS17614942 (AC)

| | Estimate | StdErr | P-value |
|---|---|---|---|
| 1. One or Two or Three | | | |
| RS1042173 (TT): | −0.86 | 0.61 | 0.156 |
| OND (n = 42) vs. Placebo (n = 48) | | | |
| RS1176713 (GG): | −3.92 | 1.57 | 0.013 |
| OND (n = 6) vs. Placebo (n = 9) | | | |
| RS17614942 (AC): | −2.73 | 0.95 | 0.004 |
| OND (n = 17) vs. Placebo (n = 19) | | | |
| TT + GG: | −6.42 | 2.41 | 0.008 |
| OND (n = 3) vs. Placebo (n = 4) | | | |
| TT + AC: | −3.37 | 1.44 | 0.019 |
| OND (n = 9) vs. Placebo (n = 7) | | | |
| GG + AC: | NA | NA | NA |
| OND (n = 0) vs. Placebo (n = 2) | | | |
| TT + GG + AC: | NA | NA | NA |
| OND (n = 0) vs. Placebo (n = 1) | | | |
| 2. Any of One or Two | | | |
| TT or GG: | −1.02 | 0.59 | 0.082 |
| OND (n = 45) vs. Placebo (n = 53) | | | |
| TT or AC: | −1.07 | 0.55 | 0.052 |
| OND (n = 50) vs. Placebo (n = 60) | | | |

TABLE 13-continued

Any one or two or three of RS1042173 (TT) or RS1176713 (GG) or RS17614942 (AC)

| | Estimate | StdErr | P-value |
|---|---|---|---|
| GG or AC: OND (n = 23) vs. Placebo (n = 26) | −3.08 | 0.82 | 0.076 |
| 3. Any of One, Two, or Three (N = 117) | | | |
| TT or GG or AC: OND (n = 53) vs. Placebo (n = 64) | −1.12 | 0.54 | 0.037 |

Additional Analysis of Gene Patterns Related to Response to Ondansetron Treatment Using the same data as was used in Example 11, further epistatic analysis among SNPs from serotonin (SERT), 5HT-3A, and 5HT-3B reveal that significant epistatic effect exists among the three genes in affecting response to ondesetron treatment as measured by DDD, DD, PHDD, and PDA.

TABLE 1A

ANOVA of Drinks per Drinking Days

| | Drinks per Drinking Days | |
|---|---|---|
| Variable | F-Value | P-Value |
| Comb | 9.91 | 0.002 |
| Treatment | 3.81 | 0.051 |
| Comb*Treatment | 7.59 | 0.006 |

Comb: (LL + TT or AC or AG), and Others

TABLE 1B

Least Squares Mean

| Effect | Estimated Mean | Standard Error |
|---|---|---|
| Others | 6.27 | 0.24 |
| Comb | 5.09 | 0.32 |

TABLE 1

Multigene SNP combinations associated with AD and ondansetron treatment outcome

| | Alcohol Dependence (AD) | | | | OND treatment response | | | | |
|---|---|---|---|---|---|---|---|---|---|
| SNP and Genotype combination | AD N | Controls N | $\chi^2$ value* | $\chi^2$ P value | OND-responders N | OND-non-responders N | $\chi^2$ value | $\chi^2$ P value** | Response variable |
| rs3758987 + 5HTTLPR(5) | | | | | | | | | |
| TT/CT + LL | 125 | 51 | 1.1613 | 0.2812 | 23 | 16 | 3.1065 | 0.078 | More than 3 standard drinks |
| all other genotype combinations | 288 | 167 | | | 34 | 52 | | | |
| rs3758987 + rs1042173(7) | | | | | | | | | |
| TT/CT + TT | 128 | 61 | 2.6371 | 0.1044 | 22 | 14 | 4.5637 | 0.0327 | improvement from the baseline in |
| all other genotype combinations | 285 | 157 | | | 35 | 54 | | | |
| 5-HTTLPR + rs1042173(6) | | | | | | | | | |
| LL + TT | 64 | 34 | 1.1505 | 0.2835 | 16 | 4 | 4.9122 | 0.0267 | the last 2 months |
| all other genotype combinations | 349 | 184 | | | 41 | 64 | | | |
| rs3758987 + rs2276307 + 5-HTTLPR(2) | | | | | | | | | |
| TT/CT + AA + LL | 73 | 33 | 0.004 | 0.9493 | 20 | 12 | 4.1519 | 0.0416 | |
| all other genotype combinations | 340 | 185 | | | 37 | 56 | | | |
| rs3758987 + 5-HTTLPR + rs1042173(4) | | | | | | | | | |
| TT/CT + LL + TT | 59 | 29 | 4.2689 | 0.0388 | 15 | 4 | 4.4385 | 0.0351 | |
| all other genotype combinations | 354 | 189 | | | 42 | 64 | | | |
| rs3758987 + rs2276307 + 5-HTTLPR + rs1042173(3) | | | | | | | | | |
| TT/CT + AA + LL + TT | 35 | 17 | 1.6332 | 0.2013 | 13 | 2 | 7.3047 | 0.0069 | |
| all other genotype combinations | 378 | 201 | | | 44 | 66 | | | |

Example 16-Additional Analysis of Gene Patterns Related to Response to Ondansetron Treatment Using the same data as was used in Example 11, further epistatic analysis among SNPs from serotonin (SERT), 5HT-3A, and 5HT-3B reveal that significant epistatic effect exists among the three genes in affecting response to ondesetron treatment as measured by DDD, DD, and PDA.

LL+TT or RS17614942 (AC) or RS1150226 (AG)

TABLE 1B-continued

Least Squares Mean

| Effect | Estimated Mean | Standard Error |
|---|---|---|
| Placebo | 6.04 | 0.27 |
| OND | 5.32 | 0.29 |
| Others: Placebo (n = 92) | 6.12 | 0.31 |
| OND (n = 97) | 6.42 | 0.31 |
| Comb: Placebo (n = 46) | 5.97 | 0.42 |
| OND (n = 38) | 4.21 | 0.47 |

TABLE 1C

Least Squares Mean Difference between Treatment and Placebo and Its 95% Confidence Intervals

| Effect | Estimated Mean Difference | Lower 95% C.I. | Upper 95% C.I. | P-Value |
|---|---|---|---|---|
| Among Comb: | | | | |
| OND vs. Placebo | −1.75 | −2.98 | −0.53 | 0.005 |
| Among OND: | | | | |
| Comb vs. Others | −2.21 | −3.29 | −1.13 | <0.0001 |

Note: 84 out of 273 patients in this study (31%). Among the patients who had LL+TT or AC or AG had at least 1.75 DDD reduction compared OND with placebo groups.

TABLE 2A

ANOVA of Drinks per Days

| Variable | Drinks per Days | |
|---|---|---|
| | F-Value | P-Value |
| Comb | 3.88 | 0.049 |
| Treatment | 3.93 | 0.048 |
| Comb*Treatment | 7.77 | 0.005 |

Comb: (LL + TT or AC or AG), and Others

TABLE 2B

Least Squares Mean

| Effect | Estimated Mean | Standard Error |
|---|---|---|
| Others | 4.41 | 0.22 |
| Comb | 3.72 | 0.30 |
| Placebo | 4.41 | 0.25 |
| OND | 3.72 | 0.27 |
| Others: Placebo (n = 92) | 4.27 | 0.29 |
| OND (n = 97) | 4.55 | 0.29 |
| Comb: Placebo (n = 46) | 4.55 | 0.39 |
| OND (n = 38) | 2.90 | 0.44 |

TABLE 2C

Least Squares Mean Difference between Treatment and Placebo and Its 95% Confidence Intervals

| Effect | Estimated Mean Difference | Lower 95% C.I. | Upper 95% C.I. | P-Value |
|---|---|---|---|---|
| Among Comb: | | | | |
| OND vs. Placebo | −1.65 | −2.78 | −0.52 | 0.004 |
| Among OND: | | | | |
| Comb vs. Others | −1.65 | −2.64 | −0.65 | 0.001 |

TABLE 3A

ANOVA of Percentage Days of Abstinent

| Variable | PDA | |
|---|---|---|
| | F-Value | P-Value |
| Comb | 3.00 | 0.083 |
| Treatment | 3.33 | 0.068 |
| Comb*Treatment | 4.30 | 0.038 |

Comb: (LL + TT or AC or AG), and Others

TABLE 3B

Least Squares Mean

| Effect | Estimated Mean | Standard Error |
|---|---|---|
| Others | 36.01 | 2.27 |
| Comb | 42.00 | 3.01 |
| Placebo | 35.89 | 2.58 |
| OND | 42.13 | 2.73 |
| Others: Placebo (n = 92) | 36.45 | 2.95 |
| OND (n = 97) | 35.58 | 2.95 |
| Comb: Placebo (n = 46) | 35.32 | 3.94 |
| OND (n = 38) | 48.68 | 4.36 |

TABLE 3C

Least Squares Mean Difference between Treatment and Placebo and Its 95% Confidence Intervals

| Effect | Estimated Mean Difference | Lower 95% C.I. | Upper 95% C.I. | P-Value |
|---|---|---|---|---|
| Among Comb: | | | | |
| OND vs. Placebo | 13.36 | 2.14 | 24.58 | 0.020 |
| Among OND: | | | | |
| Comb vs. Others | 13.11 | 3.18 | 23.03 | 0.010 |

RS17614942 is Located in HTR3B Intron 8

TABLE 2A

Frequency of RS17614942

| RS17614942 | Frequency (%) | True Frequency |
|---|---|---|
| AA | 2 (0.7%) | Very rare |
| AC | 36 (13.1%) | 13% |
| CC | 236 (86.1%) | 86% | a. Combined AC with AA

TABLE 2B

ANOVA of Drinks per Drinking Days

| Variable | Drinks per Drinking Days | |
|---|---|---|
| | F-Value | P-Value |
| RS17614942 (CC, AC/AA) | 2.62 | 0.101 |
| Treatment | 5.79 | 0.016 |
| RS17614942*Treatment | 6.92 | 0.009 |

TABLE 2C

Least Squares Mean

| Effect | Estimated Mean | Standard Error |
|---|---|---|
| AC/AA | 5.15 | 0.48 |
| CC | 5.97 | 0.23 |
| Placebo | 6.16 | 0.37 |
| OND | 4.96 | 0.39 |
| AC/AA: Placebo (n = 20) | 6.40 | 0.65 |
| OND (n = 18) | 3.90 | 0.69 |
| CC: Placebo (n = 119) | 5.92 | 0.29 |
| OND (n = 117) | 6.03 | 0.30 |

TABLE 2D

Least Squares Mean Difference between Treatment and Placebo and Its 95% Confidence Intervals

| Effect | Estimated Mean Difference | Lower 95% C.I. | Upper 95% C.I. | P-Value |
|---|---|---|---|---|
| Among AC/AA: | | | | |
| OND vs. Placebo | −2.51 | −4.32 | −0.70 | 0.007 |
| Among OND: | | | | |
| AC/AA vs. CC | −2.13 | −3.55 | −0.71 | 0.003 |
| OND vs. Placebo | −1.20 | −2.11 | −0.19 | 0.016 | b. Combined AA with CC

TABLE 2E

ANOVA of Drinks per Drinking Days

| Variable | Drinks per Drinking Days | |
|---|---|---|
| | F-Value | P-Value |
| RS17614942 (CC/AA, AC) | 2.43 | 0.120 |
| Treatment | 6.55 | 0.011 |
| RS17614942*Treatment | 7.84 | 0.005 |

TABLE 2F

Least Squares Mean

| Effect | Estimated Mean | Standard Error |
|---|---|---|
| AC | 5.23 | 0.48 |
| CC/AA | 6.03 | 0.22 |
| Placebo | 6.28 | 0.36 |
| OND | 4.98 | 0.38 |
| AC: Placebo (n = 19) | 6.59 | 0.65 |
| OND (n = 17) | 3.87 | 0.69 |
| CC/AA: Placebo (n = 120) | 5.97 | 0.28 |
| OND (n = 118) | 6.09 | 0.29 |

TABLE 2G

Least Squares Mean Difference between Treatment and Placebo and Its 95% Confidence Intervals

| Effect | Estimated Mean Difference | Lower 95% C.I. | Upper 95% C.I. | P-Value |
|---|---|---|---|---|
| Among AC: | | | | |
| OND vs. Placebo | −2.73 | −4.59 | −0.87 | 0.004 |
| Among OND: | | | | |
| AC/AA vs. CC | −2.22 | −3.68 | −0.77 | 0.003 |
| OND vs. Placebo | −1.30 | −2.30 | −0.30 | 0.011 |

RS1150226 is Located on ~500 bp Upstream of HTR3A Gene, Possibly within HTR3A Promoter

TABLE 3A

Frequency of RS1150226

| RS17614942 | Frequency (%) | True Frequency |
|---|---|---|
| AA | 2 (0.7%) | Very rare |
| AG | 44 (16.1%) | 13% |
| GG | 228 (83.2%) | 86% | a. Combined AG with AA

TABLE 3B

ANOVA of Drinks per Drinking Days

| Variable | Drinks per Drinking Days | |
|---|---|---|
| | F-Value | P-Value |
| RS1150226 (GG, AG/AA) | 4.53 | 0.033 |
| Treatment | 3.56 | 0.059 |
| RS1150226*Treatment | 4.06 | 0.044 |

TABLE 3C

Least Squares Mean

| Effect | Estimated Mean | Standard Error |
|---|---|---|
| AG/AA | 5.10 | 0.43 |
| GG | 6.08 | 0.22 |
| Placebo | 6.02 | 0.33 |
| OND | 5.15 | 0.35 |
| AG/AA: Placebo (n = 24) | 6.00 | 0.59 |
| OND (n = 22) | 4.20 | 0.61 |
| GG: Placebo (n = 115) | 6.05 | 0.28 |
| OND (n = 13) | 6.11 | 0.29 |

TABLE 3D

Least Squares Mean Difference between Treatment and Placebo and Its 95% Confidence Intervals

| Effect | Estimated Mean Difference | Lower 95% C.I. | Upper 95% C.I. | P-Value |
|---|---|---|---|---|
| Among AG/AA: | | | | |
| OND vs. Placebo | −1.80 | −3.46 | −0.15 | 0.033 |
| Among OND: | | | | |
| AG/AA vs. GG | −1.91 | −3.22 | −0.61 | 0.004 |
| AG/AA vs. GG | −0.98 | −1.89 | −0.08 | 0.033 | b. Combined GG with AA

TABLE 3E

ANOVA of Drinks per Drinking Days

| | Drinks per Drinking Days | |
|---|---|---|
| Variable | F-Value | P-Value |
| RS1150226 (GG/AA, AG) | 4.28 | 0.039 |
| Treatment | 3.58 | 0.059 |
| RS1150226*Treatment | 3.80 | 0.051 |

TABLE 3F

Least Squares Mean

| Effect | Estimated Mean | Standard Error |
|---|---|---|
| AG | 6.07 | 0.22 |
| GG/AA | 5.09 | 0.44 |
| Placebo | 6.03 | 0.33 |
| OND | 5.13 | 0.36 |
| AG: Placebo (n = 24) | 6.05 | 0.28 |
| OND (n = 20) | 6.08 | 0.29 |
| GG/AA: Placebo (n = 115) | 6.00 | 0.59 |
| OND (n = 115) | 4.19 | 0.64 |

TABLE 3G

Least Squares Mean Difference between Treatment and Placebo and Its 95% Confidence Intervals

| Effect | Estimated Mean Difference | Lower 95% C.I. | Upper 95% C.I. | P-Value |
|---|---|---|---|---|
| Among AG: | | | | |
| OND vs. Placebo | −1.81 | −3.51 | −0.12 | 0.036 |
| Among OND: | | | | |
| AG vs. GG/AA | −1.90 | −3.26 | −0.54 | 0.006 |
| AG vs. GG/AA | −0.98 | −1.90 | −0.05 | 0.039 |

RS1150226 (AG) or RS17614942 (AC)

TABLE 4A

ANOVA of Drinks per Drinking Days

| | Drinks per Drinking Days | |
|---|---|---|
| Variable | F-Value | P-Value |
| AG or AC | 3.25 | 0.072 |
| Treatment | 4.89 | 0.027 |
| (AG or AC)*Treatment | 6.32 | 0.012 |

TABLE 4B

Least Squares Mean

| Effect | Estimated Mean | Standard Error |
|---|---|---|
| Others | 6.05 | 0.22 |
| AG or AC | 5.25 | 0.41 |
| Placebo | 6.14 | 0.32 |
| OND | 5.16 | 0.34 |
| Others: | | |
| Placebo (n = 111) | 5.99 | 0.29 |
| OND (n = 112) | 6.12 | 0.30 |

TABLE 4B-continued

Least Squares Mean

| Effect | Estimated Mean | Standard Error |
|---|---|---|
| AG or AC: | | |
| Placebo (n = 27) | 6.30 | 0.55 |
| OND (n = 23) | 4.19 | 0.60 |

Others: AA/GG and AA/CC

TABLE 4C

Least Squares Mean Difference between Treatment and Placebo and Its 95% Confidence Intervals

| Effect | Estimated Mean Difference | Lower 95% C.I. | Upper 95% C.I. | P-Value |
|---|---|---|---|---|
| Among AG or/and AC: | | | | |
| OND vs. Placebo | −2.12 | −3.70 | −0.53 | 0.009 |
| Among OND: | | | | |
| (AG or AC) vs. Others | −1.91 | −3.22 | −0.61 | 0.004 |
| OND vs. Placebo | −0.99 | −1.87 | −0.11 | 0.027 |

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Chen, et al., "Effects of Topiramate and Other Anti-Glutamatergic Drugs on the Acute Intoxicating Actions of Ethanol in Mice: Modulation by Genetic Strain and Stress", Neuropsychopharmacology (2009), 34, 1454-1466.
2. Ray, et al., "A Preliminary Pharmacogenetic Investigation of Adverse Events From Topiramate in Heavy Drinkers", Experimental and Clinical Psychopharmacology, 2009, Vol. 17, No. 2, 122-129.
3. Nallani, et al., "Dose-Dependent Induction of Cytochrome P450 (CYP) 3A4 and Activation of Pregnane X Receptor by Topiramate", Epilepsia, 44 (12): 1521-1528. 2003.
4. Johnson, et al., "Topiramate for Treating Alcohol Dependence: A Randomized Controlled Trial", JAMA, 2007; 298 (14): 1641-1651.
5. Johnson, et al., "Oral Topiramate for Treatment of Alcohol Dependence: A Randomised Controlled Trial", The Lancet, Vol 361, 1677-85, 2003.

What is claimed is:

1. A method of testing the genotypes of a patient having an addictive disease or disorder comprising:
   obtaining a biological sample from the patient;
   testing the biological sample from the patient to detect the presence of genotypes (a)-(b):
   (a) the AC genotype of rs17614942 of gene HTR3B; and,
   (b) the AG genotype of rs1150226 of gene HTR3A;
   wherein the addictive disease or disorder is an alcohol-related disease or disorder or an opioid-related disorder.

2. The method of claim 1, wherein the genotypes, comprise:
   (a) the AC genotype of rs17614942 of gene HTR3B;
   (b) the AG genotype of rs1150226 of gene HTR3A; and,
   (c) the LL genotype of the functional polymorphism serotonin transporter-linked polymorphic region 5-HTTLPR of gene SLC6A4.

3. The method of claim 1, wherein the genotypes, comprise:
   (a) the AC genotype of rs17614942 of gene HTR3B;
   (b) the AG genotype of rs1150226 of gene HTR3A; and,
   (c) the TT genotype of rs1042173 of gene SLC6A4.

4. The method of claim 1, wherein the genotypes, comprise:
   (a) the AC genotype of rs17614942 of gene HTR3B;
   (b) the AG genotype of rs1150226 of gene HTR3A;
   (c) the LL genotype of the functional polymorphism serotonin transporter-linked polymorphic region 5-HTTLPR of gene SLC6A4; and,
   (d) the TT genotype of rs1042173 of gene SLC6A4.

5. The method of claim 1, further comprising:
   administering to the patient a therapeutically effective amount of ondansetron, if one of the genotypes assayed is detected.

6. The method of claim 5, wherein ondansetron is administered at a dosage ranging from 0.1 µg/kg to 1000 µg/kg per application.

7. The method of claim 5, wherein ondansetron is administered at a dosage of 1 µg/kg to 30 µg/kg per application.

8. The method of claim 5, wherein ondansetron is administered at a dosage of 1 µg/kg per application.

9. The method of claim 5, wherein ondansetron is administered at a dosage of 2 µg/kg per application.

10. The method of claim 5, wherein ondansetron is administered at a dosage of 3 µg/kg per application.

11. The method of claim 5, wherein ondansetron is administered at a dosage of 4 µg/kg per application.

12. The method of claim 5, wherein ondansetron is administered at a dosage of 5 µg/kg per application.

13. The method of claim 5, wherein ondansetron is administered at a dosage of 6 µg/kg per application.

14. The method of claim 5, wherein ondansetron is administered at a dosage of 7 µg/kg per application.

15. The method of claim 5, wherein ondansetron is administered at a dosage of 8 µg/kg per application.

16. The method of claim 5, wherein ondansetron is administered at a dosage of 9 µg/kg per application.

17. The method of claim 5, wherein ondansetron is administered at a dosage of 10 µg/kg per application.

18. The method of claim 5, wherein the addictive disease or disorder is an alcohol-related disease or disorder.

19. The method of claim 18, wherein the alcohol-related disease or disorder is selected from the group consisting of: early onset alcoholism, late onset alcoholism, alcohol-induced psychotic disorder with delusions, alcohol abuse, heavy drinking, excessive drinking, alcohol intoxication, alcohol withdrawal, alcohol intoxication delirium, alcohol withdrawal delirium, alcohol-induced persisting dementia, alcohol-induced persisting amnestic disorder, alcohol dependence, alcohol-induced psychotic disorder with hallucinations, alcohol-induced mood disorder, alcohol-induced or associated bipolar disorder, alcohol-induced or associated post-traumatic stress disorder, alcohol-induced anxiety disorder, alcohol-induced sexual dysfunction, alcohol-induced sleep disorder, alcohol-induced or associated gambling disorder, alcohol-induced or associated sexual disorder, alcohol-related disorder not otherwise specified, alcohol intoxication, and alcohol withdrawal.

20. The method of claim 5, wherein the addictive disease or disorder is an opioid-related disorder.

21. The method of claim 20, wherein the opioid-related disorder is selected from the group consisting of: opioid dependence, opioid abuse, opioid intoxication, opioid intoxication delirium, opioid-induced psychotic disorder, with delusions, opioid-induced psychotic disorder with hallucinations, opioid-induced anxiety disorder, opioid-related disorder not otherwise specified (nos), opioid intoxication, and opioid withdrawal.

* * * * *